(12) United States Patent
Shibuya et al.

(10) Patent No.: US 9,872,872 B2
(45) Date of Patent: *Jan. 23, 2018

(54) PROCESS FOR PRODUCING A PARTICULATE COMPOSITION COMPRISING AN HYDROUS CRYSTALLINE 2-O-α-D-GLUCOSYL-L-ASCORBIC ACID

(71) Applicant: Hayashibara Co., Ltd., Okayama (JP)

(72) Inventors: Takashi Shibuya, Okayama (JP);
Seisuke Izawa, Okayama (JP);
Tomoyuki Nishimoto, Okayama (JP);
Shigeharu Fukuda, Okayama (JP);
Toshio Miyake, Okayama (JP)

(73) Assignee: HAYASHIBARA CO., LTD., Okayama (JP)

( * ) Notice: Subject to any disclaimer, the term of this patent is extended or adjusted under 35 U.S.C. 154(b) by 12 days.

This patent is subject to a terminal disclaimer.

(21) Appl. No.: 14/879,280

(22) Filed: Oct. 9, 2015

(65) Prior Publication Data

US 2016/0024131 A1  Jan. 28, 2016
US 2017/0360819 A9  Dec. 21, 2017

Related U.S. Application Data

(60) Continuation of application No. 14/295,546, filed on Jun. 4, 2014, now Pat. No. 9,186,368, which is a division of application No. 13/980,223, filed as application No. PCT/JP2012/055849 on Mar. 7, 2012, now Pat. No. 9,265,781, and a continuation-in-part of application No. 12/875,786, filed on Sep. 3, 2010, now Pat. No. 8,765,416.

(30) Foreign Application Priority Data

Sep. 3, 2009 (JP) ................. 2009-204142
Dec. 28, 2009 (JP) ................. 2009-298857
May 21, 2010 (JP) ................. 2010-117835
Aug. 26, 2010 (JP) ................. 2010-190139
Mar. 7, 2011 (JP) ................. 2011-049571
Mar. 8, 2011 (JP) ................. 2011-050807

(51) Int. Cl.
C07H 17/04 (2006.01)
A61K 31/7048 (2006.01)
C12P 19/18 (2006.01)
C12P 19/60 (2006.01)
A61K 9/16 (2006.01)

(52) U.S. Cl.
CPC ............ *A61K 31/7048* (2013.01); *A61K 9/16* (2013.01); *C07H 17/04* (2013.01); *C12P 19/18* (2013.01); *C12P 19/60* (2013.01); *C12Y 204/01019* (2013.01)

(58) Field of Classification Search
None
See application file for complete search history.

(56) References Cited

U.S. PATENT DOCUMENTS

| | | |
|---|---|---|
| 3,988,206 A | 10/1976 | Shiosaka |
| 5,137,723 A | 8/1992 | Yamamoto et al. |
| 5,407,812 A | 4/1995 | Sakai et al. |
| 5,468,850 A | 11/1995 | Mandai et al. |
| 5,550,226 A | 8/1996 | Yoneyama |
| 5,630,923 A | 5/1997 | Aga et al. |
| 5,843,907 A | 12/1998 | Sakai et al. |
| 5,916,371 A | 6/1999 | Chaen et al. |
| 6,777,215 B2 | 8/2004 | Andersen et al. |
| 7,033,800 B2 | 4/2006 | Okada et al. |
| 9,186,368 B2* | 11/2015 | Shibuya ............ C07H 17/04 |
| 9,265,781 B2* | 2/2016 | Shibuya ............ C07H 17/04 |

(Continued)

FOREIGN PATENT DOCUMENTS

CA  2 714 377 A1  3/2011
EP  0425066 A1  5/1991

(Continued)

OTHER PUBLICATIONS

Sanyo•Gijyutsu•Zasshi, "Development of Stable Vitamin C and its Applications its Application" pp. 63-69, vol. 1 (1997).
Takahiko Mandai et al. "The crystal structure and physicochemical properties of L-ascorbic acid 2~glucoside" Carbohydrate Research, pp. 197-205, vol. 232 (1992).
Yutaka Inoue et al. "Application of ascorbic acid 2-glucoside as a solubilizing agent for clarithromycin: Solubilization and nanoparticie formation", International Journal of Pharmaceutics, pp. 38-45, vol. 331 (2007).
A.A.Markosyan et al., Transglycosylation of L~Ascorbic Acid, Applied Biochemistry and Microbiology, pp. 36-40, vol. 143, No. 1 (2007).

(Continued)

*Primary Examiner* — Eric Olson
(74) *Attorney, Agent, or Firm* — Browdy and Neimark, PLLC

(57) ABSTRACT

The invention provides a process for enabling the production of a particulate composition containing anhydrous crystalline ascorbic acid 2-glucoside that does not significantly cake even when the production yield of ascorbic acid 2-glucoside does not reach 35% by weight. The process for producing a particulate composition containing anhydrous crystalline ascorbic acid 2-glucoside, which comprises allowing a CGTase to act on a solution containing either liquefied starch or dextrin and L-ascorbic acid and then allowing a glucoamylase to act on the resulting solution to obtain a solution with an ascorbic acid 2-glucoside production yield of at least 27%, purifying the obtained solution to increase the ascorbic acid 2-glucoside content to a level of over 86% by weight, precipitating anhydrous crystalline ascorbic acid 2-glucoside by a controlled cooling method or pseudo-controlled cooling method, collecting the precipitated anhydrous crystalline ascorbic acid 2-glucoside, and ageing and drying the collected anhydrous crystalline ascorbic acid 2-glucoside.

1 Claim, 5 Drawing Sheets

(56) References Cited

U.S. PATENT DOCUMENTS

| | | |
|---|---|---|
| 2004/0231662 A1 | 11/2004 | De Mendonca Ferreira et al. |
| 2007/0142652 A1 | 6/2007 | Arumughan et al. |
| 2007/0148287 A1 | 6/2007 | Svendsen et al. |
| 2010/0105562 A1 | 4/2010 | Schmidt et al. |
| 2012/0107380 A1 | 5/2012 | Tuinstra et al. |

FOREIGN PATENT DOCUMENTS

| | | |
|---|---|---|
| EP | 1553186 A1 | 7/2005 |
| JP | 39597/88 A | 2/1988 |
| JP | 139288/91 A | 6/1991 |
| JP | 183492/91 A | 8/1991 |
| JP | 135992/91 A | 10/1991 |
| JP | 046112/92 A | 2/1992 |
| JP | 182412/92 A | 6/1992 |
| JP | 182413/92 A | 6/1992 |
| JP | 182414/92 A | 6/1992 |
| JP | 182415/92 A | 6/1992 |
| JP | 333260/92 A | 11/1992 |
| JP | 4-360663 A | 12/1992 |
| JP | 117290/93 A | 5/1993 |
| JP | 208991/93 A | 8/1993 |
| JP | 244945/93 A | 9/1993 |
| JP | 10-168093 A | 6/1998 |
| JP | 2000-026375 A | 1/2000 |
| JP | 2000-072417 A | 3/2000 |
| JP | 2002/088095 A | 3/2002 |
| JP | 2002-326924 A | 11/2002 |
| JP | 2003-171290 A | 6/2003 |
| JP | 2004-065098 A | 3/2004 |
| JP | 2004-217597 A | 8/2004 |
| JP | 2004-537326 A | 12/2004 |
| JP | 2005-239653 A | 9/2005 |
| JP | 2006-225327 A | 8/2006 |
| JP | 2007-63177 A | 3/2007 |
| WO | 9633267 A1 | 10/1996 |
| WO | 9915633 A1 | 4/1999 |
| WO | 0190338 A1 | 11/2001 |
| WO | 0210361 A1 | 2/2002 |
| WO | 2005-034938 A1 | 4/2005 |
| WO | 2005-087182 A | 9/2005 |
| WO | 2006/033412 A1 | 3/2006 |
| WO | 2006022174 A1 | 3/2006 |
| WO | 2006132310 A1 | 12/2006 |
| WO | 2006137129 A1 | 12/2006 |
| WO | 2007086327 A1 | 8/2007 |
| WO | 2009049391 A1 | 4/2009 |
| WO | 2011027790 A1 | 3/2011 |

OTHER PUBLICATIONS

Hajime AgA et al, "Synthesis of 2-0-or-n-Glucopyraoosyl L-Ascorbic Acid by Cyclomaltodextrin Glucanotransferase from Bacillus stearothermophilus", Agricultural Biological Chemistry, pp. 1751-1756, vol. 7, (1991).

Hayashibara Biochemical Laboratories, Inc. "Hayashibara's saccharide-related products", Wake Analytical Circle, No. 29, p. 6, (2003).

"Kogyo-yo-Toshitsu-Koso-Handbook", edited by Kodansha Scientific Ltd., p. 51; pp. 56-63, (1999).

P. H. Hermans et al., "Quantitative X-Ray Investigations on the Crystallinity of Cellulose Fibers. A Background Analysis", Journal of Applied Physics, pp. 491-506, (1948).

P. H. Hermans et al., X-Ray Studies on the Crystallinity of Cellulose*, Journal of Polymer Science, pp. 135,144, vol. 4, (1949).

Koriaki Kubota et al., "Study by Mullin and Kyvit" Wakariyasui Batch Shoseki, The Society of Separation Process Engineers, pp. 32-41, (2010).

Search Report dated Dec. 22, 2010 from the European Patent Office issued in Appl No. EP 10175307.7.

Office Action dated Feb. 1, 2011 in connection with corresponding Japanese Patent Application No. 2010-218960 (5 pages).

Kelly et al. "The evolution of cyclodextrin glucanotransferase product specificity" (2009) Applied Microbiology Biotechnology, vol. 84:119-133.

Tanaka et al., "Characterization of Bacillus stearothermophilus cyclodextrin glucanotransferase in ascorbic acid 2-0-a-glucoside formation." (1991), Biochemica et Biophysica Acta, 1078: 127-132.

Rendleman, Jr., "The Production of Cyclodextrins using CGTase from Bacillus macerans." (1997), Methods in Biotechnology,vol. 10: Carbohydrate Biotechnology Protocols, 89-101.

Juza et al., Simulated moving-bed chromatography and its application to chirotechnology, TIBTECH 18:108-118 (2000).

* cited by examiner

PROCESS FOR PRODUCING A PARTICULATE COMPOSITION COMPRISING AN HYDROUS CRYSTALLINE 2-O-α-D-GLUCOSYL-L-ASCORBIC ACID

TECHNICAL FIELD

The present invention relates to a process for producing a particulate composition containing anhydrous crystalline 2-O-α-D-glucosyl-L-ascorbic acid, more particularly, to a process for producing a particulate composition, containing anhydrous crystalline 2-O-α-D-glucosyl-L-ascorbic acid that significantly, more hardly cakes compared to conventional ones.

BACKGROUND ART

Due to its advantageous physiological activities and antioxidant action, L-ascorbic acid has been used for various purposes, including those for food products and cosmetics. L-Ascorbic acid, however, has a serious disadvantageous in that it is unstable because of its reducibility and susceptible to oxidative degradation to easily lose its physiological activities. To overcome the disadvantage, the same applicant as the present invention, as one of the co-applicants of Patent Literature 1, disclosed 2-O-α-D-glucosyl-L-ascorbic acid that is composed of one molecule of D-glucose bound to the hydroxyl group at the C-2 position of L-ascorbic acid (hereinafter, abbreviated as "ascorbic acid 2-glucoside", throughout the specification). As outstanding characteristics, ascorbic acid 2-glucoside does not exhibit reducibility, has a satisfactory stability, and exerts the physiological activities inherent to L-ascorbic acid after being hydrolyzed in living bodies into L-ascorbic acid and D-glucose by an in vivo enzyme inherently existing in the living bodies. According to the process disclosed in Patent Literature 1, ascorbic acid 2-glucoside is formed by allowing a saccharide-transferring enzyme such as cyclomaltodextrin glucanotransferase (abbreviated as "CGTase", hereinafter) or α-glucosidase to act on a solution containing L-ascorbic acid and an α-glucosyl saccharide compound.

In Patent Literature 2, the same applicant as the present invention succeeded in crystallizing ascorbic acid 2-glucoside from a supersaturated solution of ascorbic acid 2-glucoside and disclosed crystalline ascorbic acid 2-glucoside and a particulate composition containing the same. In Non-Patent Literature 1, the same applicant as the present invention disclosed a process for producing a high ascorbic acid 2-glucoside content product on a large scale. Until now, crystalline ascorbic acid 2-glucoside has been known to exist in an anhydrous crystalline form only. For reference, Non-Patent Literatures 2 and 3 report the results on X-ray structure analysis for crystalline ascorbic acid 2-glucoside.

In Patent Literatures 3 and 4, the same applicant as the present invention further disclosed a process for producing a high ascorbic acid 2-glucoside content product, which comprises the steps of subjecting a solution with ascorbic acid 2-glucoside formed by enzymatic reactions to a column chromatography with a strong-acid cation exchange resin, and collecting a fraction rich in ascorbic acid 2-glucoside. In Patent Literature 5, the same applicant as the present invention disclosed a process for producing a high ascorbic acid 2-glucoside content product, comprising subjecting a solution containing ascorbic acid 2-glucoside formed by enzymatic reactions to electrodialysis with an anion-exchange membrane to remove impurities such as L-ascorbic acid and saccharides from the solution; and in Patent Literature 6, the same applicant as the present invention disclosed a process for producing a high ascorbic acid 2-glucoside content product, which comprises the steps of subjecting a solution with ascorbic acid 2-glucoside to an anion-exchange resin, and selectively desorbing the ingredients adsorbed on the resin to obtain a fraction rich in ascorbic acid 2-glucoside.

In addition, Patent Literatures 7 to 11 disclose a CGTase derived from a microorganism of the species *Bacillus stearothermophilus*, which is now classified into a microorganism of the species *Geobacillus stearothermophilus*; a nucleotide sequence of a gene encoding such CGTase protein; an amino acid sequence determined from the nucleotide sequence; a mutant CGTase prepared by artificially introducing a mutation into the amino acid sequence; and a process for producing saccharides using the same. Non-Patent Literatures 4 and 5 disclose the formation of ascorbic acid 2-glucoside by allowing a CGTase derived from a microorganism of the species *Bacillus stearothermophilus* to act on a solution containing amylaceous substance and L-ascorbic acid, and then allowing glucoamylase to act on the resulting solution to form ascorbic acid 2-glucoside.

In Patent Literature 12, the same applicant as the present invention disclosed a process for producing ascorbic acid 2-glucoside comprising allowing either an α-isomaltosyl-glucosaccharide-forming enzyme or an α-isomaltosyl-glucosaccharide-forming enzyme and CGTase to act on a solution containing L-ascorbic acid and α-glucosyl saccharide compound to form ascorbic acid 2-glucoside. Patent Literatures 13 and 14 by the same applicant as the present invention respectively disclose that an α-isomaltosyl-glucosaccharide-forming enzyme and an α-isomaltosyl-transferring enzyme form ascorbic acid 2-glucoside by catalyzing the transfer of saccharides to L-ascorbic acid.

As for the use of ascorbic acid 2-glucoside, many proposals have been made as shown in Patent Literatures 15 to 34. Due to its advantageous properties, ascorbic acid 2-glucoside has been extensively used as a food material, food additive material, cosmetic material, quasi-drug material, or pharmaceutical material for use as in conventional L-ascorbic acid and for other uses where L-ascorbic acid could not have been used because of its unstableness.

As described above, at present, ascorbic acid 2-glucoside has been known to be produced by using various saccharide-transferring enzymes from L-ascorbic acid and an amylaceous substance as materials. Among them, to the extent of the knowledge to date of the present applicant, the method comprising allowing CGTase as a saccharide-transferring enzyme to act on a solution containing either liquefied starch or dextrin and L-ascorbic acid is an industrially advantageous method because the production yield of ascorbic acid 2-glucoside is the highest. Based on the finding, the present applicant has produced a particulate composition containing anhydrous crystalline ascorbic acid 2-glucoside by a process comprising allowing CGTase to act on a solution containing either liquefied starch or dextrin and L-ascorbic acid, and has commercialized it as a material for cosmetics/quasi-drugs and for food products and food additives under the respective product names of "AA2G" (commercialized by Hayashibara Biochemical Laboratories, Inc., Okayama, Japan) and "ASCOFRESH" (commercialized by Hayashibara Shoji, Co., Ltd., Okayama, Japan), where the all of these conventional particulate compositions containing anhydrous crystalline ascorbic acid 2-glucoside, which have been commercialized as such a material for cosmetics/quasi drugs and for food products and food additives, are abbreviated as "quasi-drug-grade powders", hereinafter.

Although quasi-drug-grade powders have a relatively high ascorbic acid 2-glucoside purity of 98.0% by weight or higher product specifications and have a satisfactory flowability as powders just after their productions, they have a disadvantage in that they induce caking due to their own weights and moisture absorptions when allowed to stand under relatively high temperature and humid conditions. In view of such a disadvantage, quasi-drug-grade powders have been commercialized in a product form, enclosed in a steel can with a lid after packed in a polyethylene bag by 10-kg weight each along with a desiccant, however, the present inventors' later finding revealed that quasi-drug-grade powders even in such a product form have the disadvantage that they may often cause caking and lose their useful properties as powders when stored for a relatively long period of time. When a particulate composition containing anhydrous crystalline ascorbic acid 2-glucoside for use as a cosmetic material or quasi-drug material or as a food material or food additive material is once caked, it may cause any troubles in the steps of transporting, sieving, mixing raw materials, etc., if production plants are designed under the premise that raw materials are powders retaining flowability.

A particulate composition containing anhydrous crystalline ascorbic acid 2-glucoside (product name "Ascorbic acid 2-Glucoside 999", Code No.: AG124, commercialized by Hayashibara Biochemical Laboratories, Inc., Okayama, Japan) (hereinafter abbreviated as "a reagent-grade powder") (see, for example, Non-Patent Literature 6), which has been commercialized as an analytical standard reagent by the same applicant as the present invention, does not cake even under the conditions that allow a quasi-drug-grade powder to cake, and still retains its properties as a powder. Similarly as in a quasi-drug-grade powder, such a reagent-grade powder is a powder prepared by allowing CGTase to act on a solution containing L-ascorbic acid and an amylaceous substance, purifying and concentrating the obtained solution containing ascorbic acid 2-glucoside to precipitate anhydrous crystalline ascorbic acid 2-glucoside, and collecting the precipitated crystals. Such a reagent-grade powder is different from a quasi-drug-grade powder in that, in addition to conventional steps, the former needs additional steps such as a recrystallization step of dissolving the once obtained crystals and then recrystallizing the crystals, and a washing step of repeatedly washing the crystals, obtained through a recrystallization step, with refined water, etc., to increase the purity of ascorbic acid 2-glucoside to a distinctly high purity of 99.9% or higher by weight. Accordingly, even in a quasi-drug-grade powder, it can be speculated to be made into a particulate composition containing anhydrous crystalline ascorbic acid 2-glucoside that substantially, more hardly cakes, by increasing the purity of ascorbic acid 2-glucoside to a level of at least 99.9% by weight.

However, as described above, to increase the purity of ascorbic acid 2-glucoside to a level of at least 99.9% by weight, a recrystallization step and a repeating washing step with refined water, etc., should be added in addition to the usual production step, resulting in disadvantages of not only an increment of times and labors required for its production but a loss of ascorbic acid 2-glucoside in the recrystallization and washing steps, as well as a reduction of the production yield and an increment of the production cost by a large margin. Because of this, it is not a realistic option to simply increase the purity of ascorbic acid 2-glucoside to a level of at least 99.9% by weight for the purpose of obtaining a particulate composition containing anhydrous crystalline ascorbic acid 2-glucoside that substantially, more hardly cakes compared to a quasi-drug-grade powder. In addition, according to the present inventors' knowledge, a reagent-grade powder has a disadvantage that it is inferior in solubility when mixed with a hydrophilic solvent, such as an aqueous 1,3-butylene glycol solution, which is frequently used in cosmetics and quasi-drugs.

Under these circumstances, the present applicant has made trial and error efforts, revealing that, in a production method of allowing CGTase to act on a solution containing either liquefied starch or dextrin and L-ascorbic acid and then allowing glucoamylase to act on the resulting solution, in the case of increasing the production yield of ascorbic acid 2-glucoside in the solution obtained by the enzymatic reactions to a level of at least 35% by weight, a powder that significantly, more hardly cakes compared to a conventional quasi-drug-grade powder can be produced through substantially the same steps as the process for producing such a conventional quasi-drug-grade powder, without dissolving and recrystallizing the once obtained anhydrous crystalline ascorbic acid 2-glucoside; and disclosed the above finding in Patent Literature 35. In the above process, however, there exists an inconvenience in that a limited, specific CGTase should be used alone or in combination with a starch-debranching enzyme such as isoamylase to increase the production yield of ascorbic acid 2-glucoside to a level of at least 35% by weight in the reaction mixture obtained by the enzymatic reactions, and such process lacks general versatility as a production method.

PRIOR ART LITERATURES

Patent Literatures

[Patent Literature 1] Japanese Patent Kokai No. 139288/91
[Patent Literature 2] Japanese Patent Kokai No. 135992/91
[Patent Literature 3] Japanese Patent Kokai No. 183492/91
[Patent Literature 4] Japanese Patent Kokai No. 117290/93
[Patent Literature 5] Japanese Patent Kokai No. 208991/93
[Patent Literature 6] Japanese Patent Kokai No. 2002-088095
[Patent Literature 7] Japanese Patent Kokai No. 63189/75
[Patent Literature 8] Japanese Patent Kokai No. 39597/88
[Patent Literature 9] Japanese Patent Kokai No. 244945/93
[Patent Literature 10] International Patent Publication No. WO 96033267
[Patent Literature 11] International Patent Publication No. WO 99015633
[Patent Literature 12] Japanese Patent Kokai No. 2004-065098
[Patent Literature 13] International Patent Publication No. WO 02010361
[Patent Literature 14] International Patent Publication No. WO 01090338
[Patent Literature 15] International Patent Publication No. WO 05087182
[Patent Literature 16] Japanese Patent Kokai No. 046112/92
[Patent Literature 17] Japanese Patent Kokai No. 182412/92
[Patent Literature 18] Japanese Patent Kokai No. 182413/92

[Patent Literature 19] Japanese Patent Kokai No. 182419/92
[Patent Literature 20] Japanese Patent Kokai No. 182415/92
[Patent Literature 21] Japanese Patent Kokai No. 182414/92
[Patent Literature 22] Japanese Patent Kokai No. 333260/96
[Patent Literature 23] Japanese Patent Kokai No. 2005-239653
[Patent Literature 24] International Patent Publication No. WO 06033412
[Patent Literature 25] Japanese Patent Kokai No. 2002-326924
[Patent Literature 26] Japanese Patent Kokai No. 2003-171290
[Patent Literature 27] Japanese Patent Kokai No. 2004-217597
[Patent Literature 28] International Patent Publication No. WO 05034938
[Patent Literature 29] Japanese Patent Kokai No. 2006-225327
[Patent Literature 30] International Patent Publication No. WO 06137129
[Patent Literature 31] International Patent Publication No. WO 06022174
[Patent Literature 32] Japanese Patent Kokai No. 2007-063177
[Patent Literature 33] International Patent Publication No. WO 06132310
[Patent Literature 34] International Patent Publication No. WO 07086327
[Patent Literature 35] International Patent Publication No. WO 2011/027790

Non-Patent Literatures

[Non-Patent Literature 1] *Sanyo-Gijyutsu-Zasshi*, Vol. 45, No. 1, pp. 63-69, 1997
[Non-Patent Literature 2] *Carbohydrate Research*, Takahiko MANDAI et al., Vol. 232, pp. 197-205, 1992
[Non-Patent Literature 3] *International Journal of Pharmaceutics*, Yutaka INOUE et al., Vol. 331, pp. 38-45, 2007
[Non-Patent Literature 4] *Applied Biochemistry and Microbiology*, Vol. 143, No. 1, pp. 36-40, 2007
[Non-Patent Literature 5] *Agricultural Biological Chemistry*, Vol. 7, pp. 1751-1756, 1991
[Non-Patent Literature 6] *Wako Analytical Circle*, No. 29, pp. 6, 2003

DISCLOSURE OF INVENTION

Object of the Invention

The present invention, which was made to solve the above disadvantage, aims to provide a process for producing a particulate composition containing anhydrous crystalline ascorbic acid 2-glucoside that enables the production of a particulate composition containing anhydrous crystalline ascorbic acid 2-glucoside that significantly, more hardly cakes compared to a quasi-drug-grade powder, even in the case that the production yield of ascorbic acid 2-glucoside in a reaction solution, obtained by enzymatic reactions, is below 35% by weight.

Means to Attain the Object

In order to overcome the above object, the present inventors further continued studying and repeated trial and error efforts on a process for producing a particulate composition containing anhydrous crystalline ascorbic acid 2-glucoside, and found that, by applying the later-described controlled cooling method or pseudo-controlled cooling method when in precipitating anhydrous crystalline ascorbic acid 2-glucoside from a solution containing ascorbic acid 2-glucoside, an anhydrous crystalline ascorbic acid 2-glucoside that significantly, more hardly cakes compared to a conventional quasi-drug-grade powder can be produced through substantially the same steps as those of a conventional process for producing such a quasi-drug-grade powder, even when the production yield of ascorbic acid 2-glucoside in a reaction solution obtained by enzymatic reactions is below 35% by weight.

In other words, the present invention solves the above object by providing a process for producing anhydrous crystalline ascorbic acid 2-glucoside, which contains the following steps (a) to (e);

(a) a step of allowing CGTase to act on a solution containing either liquefied starch or dextrin and L-ascorbic acid as materials, and then allowing glucoamylase to act on the resulting solution to obtain a solution containing ascorbic acid 2-glucoside with an ascorbic acid 2-glucoside production yield of at least 27% by weight;

(b) a step of purifying the resulting solution containing ascorbic acid 2-glucoside to give an ascorbic acid 2-glucoside content of over 86% by weight, on a dry solid basis (may be abbreviated as "d.s.b.", hereinafter);

(c) a step of precipitating anhydrous crystalline ascorbic acid 2-glucoside from the purified solution with an ascorbic acid 2-glucoside content of over 86% by weight, d.s.b., by a controlled cooling method or pseudo-controlled cooling method;

(d) a step of collecting the precipitated anhydrous crystalline ascorbic acid 2-glucoside; and (e) a step of ageing, drying, and optionally pulverizing the collected anhydrous crystalline ascorbic acid 2-glucoside without dissolving and recrystallizing it to obtain a particulate composition containing anhydrous crystalline ascorbic acid 2-glucoside, which contains an ascorbic acid 2-glucoside in a level of, on a dry solid basis, over 98.0% by weight but below 99.9% by weight, and has a degree of crystallinity for anhydrous crystalline ascorbic acid 2-glucoside of at least 90%, when calculated based on the powder X-ray diffraction profile of the particulate composition.

According to the process of the present invention, a particulate composition containing anhydrous crystalline ascorbic acid 2-glucoside, which has an ascorbic acid 2-glucoside content of, on a dry solid basis, over 98.0% by weight but below 99.9% by weight and has a degree of crystallinity for anhydrous crystalline ascorbic acid 2-glucoside of at least 90% when calculated based on the powder X-ray diffraction profile of the particulate composition, can be obtained by precipitating anhydrous crystalline ascorbic acid 2-glucoside from an ascorbic acid 2-glucoside solution, which is obtained by enzymatic reactions and appropriately purifying the resulting reaction solution, by the later-described controlled cooling method or pseudo-controlled cooling method, as long as the production yield of ascorbic acid 2-glucoside is at least 27% by weight in the reaction solution, even when the level of production yield of ascorbic acid 2-glucoside does not reach 35% by weight.

The particulate composition containing anhydrous crystalline ascorbic acid 2-glucoside obtained by the above process has an ascorbic acid 2-glucoside purity of over 98.0% by weight but below 99.9% by weight, wherein the purity level is nearly equal to or lesser than that of a conventional quasi-drug-grade powder; has a degree of crystallinity for anhydrous crystalline ascorbic acid 2-glucoside (throughout the specification, simply abbreviated as "degree of crystallinity", hereinafter) of as high as at least 90%; is a powder that significantly, more hardly cakes compared to a quasi-drug-grade powder; and has an advantageous solubility in hydrophilic solvents used widely in cosmetics and quasi-drugs compared to a reagent-grade powder due to its ascorbic acid 2-glucoside purity of less than 99.9% by weight. Such particulate composition can be easily handleable and suitably used as a food material, food additive material, cosmetic material, quasi-drug material, and pharmaceutical material.

In the process according to the present invention, the production yield of ascorbic acid 2-glucoside in a reaction solution obtained by enzymatic reactions should preferably be at least 27% by weight, and, in some cases, it can be at least 35% by weight. The process is particularly advantageous in that it provides a particulate composition, which is a powder that significantly, more hardly cakes compared to a quasi-drug-grade powder, by almost the same step as in a conventional quasi-drug-grade powder except for applying a controlled cooling method or pseudo-controlled cooling method, even when the level of the above-identified production yield is less than 35% by weight, i.e., at least 27% by weight but less than 35% by weight. When the above production yield is at least 35% by weight, the process according to the present invention has the merit that it can produce a particulate composition, which is a powder that significantly, more hardly cakes compared to a quasi-drug-grade powder, by using almost the same step as of a conventionally employed process for producing a quasi-drug-grade powder, except for applying a controlled cooling method or pseudo-controlled cooling method. In the process according to the present invention, wherein in the step (a) of obtaining a solution containing ascorbic acid 2-glucoside with its production yield of at least 27% by weight, a starch-debranching enzyme such as isoamylase and pullulanase can be used in combination with CGTase to more increase the production yield of ascorbic acid 2-glucoside in the reaction solution.

Moreover, in the process according to the present invention, wherein in the step (b) of purifying the resulting solution containing ascorbic acid 2-glucoside to give an ascorbic acid 2-glucoside content of over 86% by weight, d.s.b., a column chromatography using an anion-exchange resin as a column packing material and a simulated-moving-bed column chromatography using a strong-acid cation exchange resin as a column packing material can be also employed. In the step (b), when the column chromatography using the above anion-exchange resin as a column packing material and the simulated-moving-bed column chromatography using the above strong-acid cation exchange resin as a column packing material are employed in combination, a solution containing ascorbic acid 2-glucoside with an ascorbic acid 2-glucoside content of over 86% by weight, d.s.b., can be more efficiently obtained as a merit.

Further, the present inventors' continued studying revealed that CGTases, capable of producing at least 27% by weight of ascorbic acid 2-glucoside in reaction solutions obtained by the enzymatic reactions in the step (a), have a common characteristic feature at amino acid level.

More specifically, the present invention also solves the above object by providing a process for producing anhydrous crystalline ascorbic acid 2-glucoside using, as the above CGTases, any CGTases having the following partial amino acid sequences of (a) to (d):

(a) Asn-Glu-Val-Asp-$X_1$-Asn-Asn;
(b) Met-Ile-Gln-$X_2$-Thr-Ala;
(c) Pro-Gly-Lys-Tyr-Asn-Ile; and
(d) Val-$X_3$-Ser-Asn-Gly-Ser-Val.
(Wherein $X_1$ means Pro or Ala, $X_2$ means Ser or Asp, and $X_3$ means Ser or Gly, respectively.)

Examples of the CGTases having the above partial amino acid sequences of (a) to (d) include natural and recombinant enzymes derived from microorganisms of the species *Geobacillus stearothermophilus* or *Thermoanaerobacter thermosulfurigenes*, more specifically, CGTases having any of the amino acid sequences of SEQ ID NOs: 1, 3, 4 and 5, which can be preferably used in the present invention.

The particulate composition containing anhydrous crystalline ascorbic acid 2-glucoside, obtained by the process of the present invention, preferably contains ascorbic acid 2-glucoside in a content of, on a dry solid basis, over 98.0% by weight but below 99.9% by weight; has a degree of crystallinity for anhydrous crystalline ascorbic acid 2-glucoside of at least 90%, when calculated based on the powder X-ray diffraction profile of the particulate composition; contains L-ascorbic acid and/or D-glucose derived from the materials; contains L-ascorbic acid in a content of not higher than 0.1% by weight, d.s.b.; and has a reducing power of the whole particulate composition of less than one percent by weight.

Effect of the Invention

Since the process of the present invention enables to produce a particulate composition containing anhydrous crystalline ascorbic acid 2-glucoside, which significantly, more hardly cakes compared to a quasi-drug-grade powder, even in the case that the production yield of ascorbic acid 2-glucoside in a reaction solution obtained by enzymatic reactions is below 35% by weight, it provides a great benefit that the range of selecting enzymes, particularly, CGTases, used for enzymatic reactions, is expanded widely. The process of the present invention provides an information on partial amino acid sequences common in CGTases that realize the production yield of ascorbic acid 2-glucoside at a level of at least 27% by weight in the enzymatic reactions, and therefore it provides a merit that the screening of CGTases feasible for the process of the present invention becomes possible based on the partial amino acid sequences. Further, according to the process of the present invention, a particulate composition containing anhydrous crystalline ascorbic acid 2-glucoside, which significantly, more hardly cakes compared to a conventional quasi-drug-grade powder, can be produced by a process which, in terms of steps, is not different from the process for producing a conventional quasi-drug-grade powder that uses either liquefied starch or dextrin and L-ascorbic acid as materials, except for using a controlled cooling method or pseudo-controlled cooling method in the crystallization step for precipitating anhydrous crystalline ascorbic acid 2-glucoside from a reaction solution obtained by enzymatic reactions; and therefore a particulate composition containing anhydrous crystalline ascorbic acid 2-glucoside, which significantly, more hardly cakes compared to a quasi-drug-grade powder, can be produced with a time, labor, production facility, and cost that are close enough to those conventionally required for producing such a quasi-drug-grade powder as a merit.

For reference, when used as a powdered food material, food additive material, cosmetic material, quasi-drug material, and pharmaceutical material, the particulate composition containing anhydrous crystalline ascorbic acid 2-glucoside produced by the process of the present invention exerts the merit that it can be easily preserved, stored, and handled, as well as being substantially free of causing troublesome in processes such as transporting, sieving, and mixing materials, even when used in a production plant constructed on the premise that the materials used therein should have flowability, because the particulate composition, as a constituent of the powdered materials, significantly, more hardly cakes.

Since the particulate composition containing anhydrous crystalline ascorbic acid 2-glucoside produced by the process of the present invention can be easily controlled its particle size distribution to that required for food materials, etc., i.e., it can be controlled to those with a particle size of less than 150 μm in a content of at least 70% by weight to the whole particulate composition and those with a particle size of at least 53 μm but less than 150 μm in a content of 40 to 60% by weight to the whole particulate composition, the particulate composition has the merit that it can be used as before without altering prior production steps and material standards, even when used as a food material, food additive material, cosmetic material, quasi-drug material, or pharmaceutical material. Since the particulate composition containing anhydrous crystalline ascorbic acid 2-glucoside, produced by the process according to the present invention, contains L-ascorbic acid and/or D-glucose and has a reducing power of the whole powder of over 0% by weight but less than 1% by weight and, in spite of the fact that it is a particulate composition produced from either liquefied starch or dextrin and L-ascorbic acid as materials, it has the merit that it has no fear of causing quality deterioration such as color change even when mixed with other substances having amino groups intramolecularly such as amino acids and proteins. Further, since the particulate composition containing anhydrous crystalline ascorbic acid 2-glucoside produced by the process of the present invention contains L-ascorbic acid in a content of over 0% by weight but below 0.1% by weight, it in itself has no fear of turning color into pale brown even when stored alone for a relatively long period of time and it can be used as a food material, food additive material, cosmetic material, quasi-drug material, and pharmaceutical material as a substantially uncolored white powder.

BEST MODE FOR CARRYING OUT THE INVENTION

1. Definition of Terms

Figure 1:
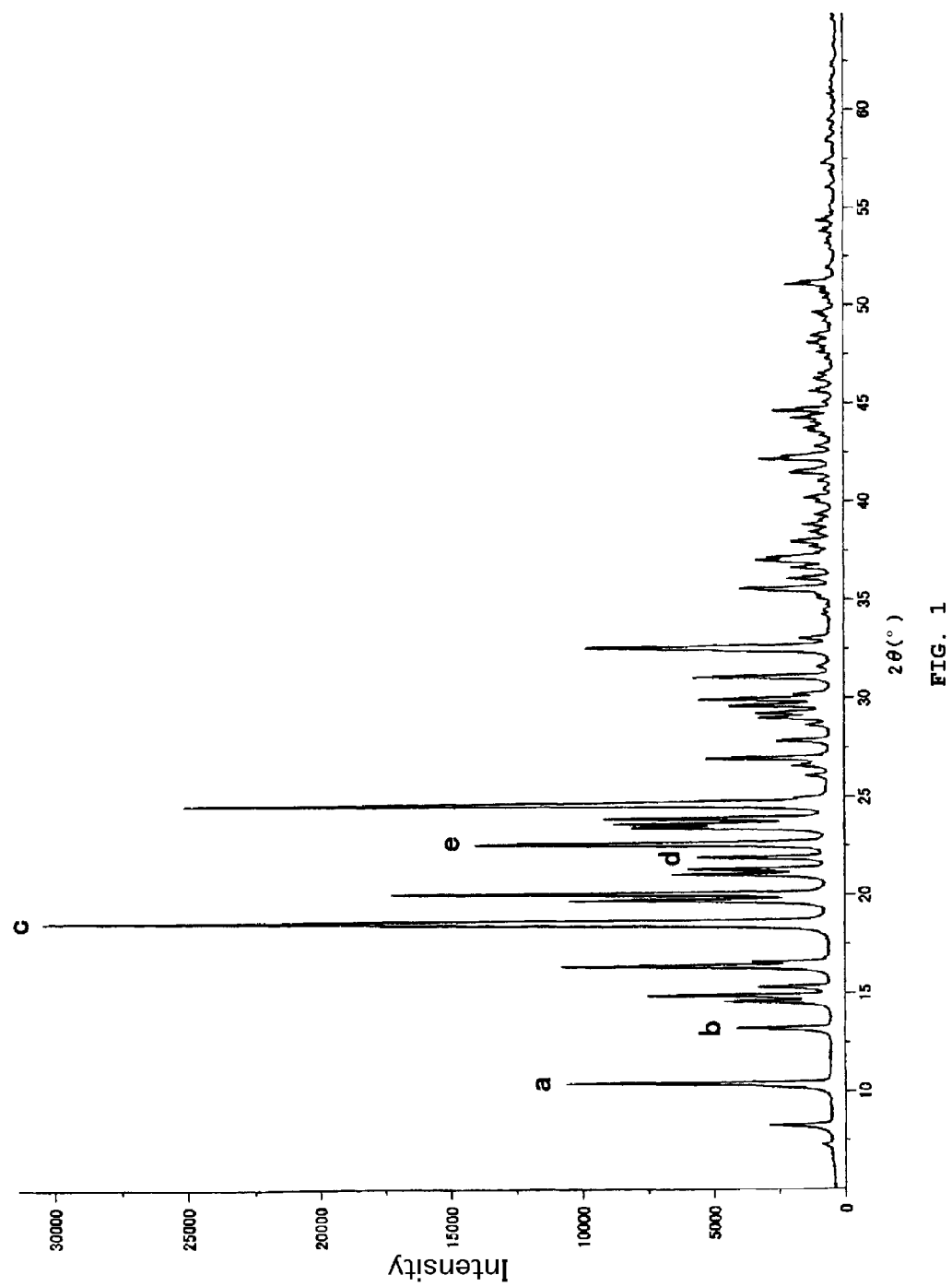
FIG. 1 is an example of powder X-ray diffraction pattern with a characteristic X-ray for a particulate composition containing anhydrous crystalline ascorbic acid 2-glucoside, which substantially consists of anhydrous crystalline ascorbic acid 2-glucoside.

Throughout the specification, the following terms mean as follows:

<Degree of Crystallinity>

The term "a degree of crystallinity for anhydrous crystalline ascorbic acid 2-glucoside" as referred to as in the specification means a value defined by the following Formula [1].

$$\text{Degree of crystallinity}(\%) = \frac{Hs - H_0}{H_{100} - H_0} \times 100 \quad \text{Formula [1]}$$

$H_{100}$: An analytical value for a degree of crystallinity, determined based on the powder X-ray diffraction profile for a powdered standard sample containing anhydrous crystalline ascorbic acid 2-glucoside, where the powdered standard sample consists substantially of anhydrous crystalline ascorbic acid 2-glucoside.

$H_0$: An analytical value for a degree of crystallinity, determined based on the powder X-ray diffraction profile for a powdered standard sample containing ascorbic acid 2-glucoside, where the powdered standard sample consists substantially of an amorphous form of ascorbic acid 2-glucoside.

Hs: An analytical value for a degree of crystallinity, determined based on the powder X-ray diffraction profile for, as a test sample, a powder containing ascorbic acid 2-glucoside.

In Formula [1], the powder X-ray diffraction profiles for the basis of determining analytical values $H_{100}$, $H_0$, and Hs can be usually determined by a powder X-ray diffractometer equipped with a reflective or transmissive optical system. The powder X-ray diffraction profiles contain data for diffraction angles and diffraction strengths of anhydrous crystalline ascorbic acid 2-glucoside contained in a test or standard sample. Examples of a method for determining the analytical data for the degrees of crystallinity of such samples based on their powder X-ray diffraction profiles include, for example, Hermans' method, Vonk's method, etc. Among which the Hermans' method is preferable because of its easiness and accuracy. Since any of these analytical methods has now been provided as a computer software, any powder X-ray diffractometers equipped with an analytical apparatus installed with any of the above computer softwares can be favorably used.

As "a powdered standard sample containing anhydrous crystalline ascorbic acid 2-glucoside, where the powdered standard sample consists substantially of anhydrous crystalline ascorbic acid 2-glucoside", for determining the analytical value $H_{100}$, there must be used an anhydrous crystalline ascorbic acid 2-glucoside in the form of a powder or single crystal, which has an ascorbic acid 2-glucoside purity of at least 99.9% by weight (throughout the specification, "% by weight" is abbreviated as "%", unless specified otherwise but the "%" affixed to the degree of crystallinity should not be limited thereunto), exhibits characteristic diffraction peaks inherent to anhydrous crystalline ascorbic acid 2-glucoside, and consists substantially of anhydrous crystalline ascorbic acid 2-glucoside. Examples of those in the form of a powder or single crystal include the above-identified reagent-grade powder, a particulate composition containing anhydrous crystalline ascorbic acid 2-glucoside obtained by recrystallizing the reagent-grade powder, and anhydrous crystalline ascorbic acid 2-glucoside in the form of a single crystal. For reference, when analyzed with a computer software for the Hermans' method, a powder X-ray diffraction profile of the above-identified powdered standard sample of the particulate composition containing anhydrous crystalline ascorbic acid 2-glucoside, which consists substantially of anhydrous crystalline ascorbic acid 2-glucoside, gives an analytical value $H_{100}$, usually, ranging from about 70.2% to about 70.5%.

As "a powdered standard sample containing ascorbic acid 2-glucoside, where the powdered standard sample consists substantially of an amorphous form of ascorbic acid 2-glucoside" for determining the analytical value $H_0$, it must be used an ascorbic acid 2-glucoside in the form of a powder, which has an ascorbic acid 2-glucoside purity of at least 99.1%, exhibits a powder X-ray diffraction pattern consisting of only halo inherent to its amorphous form, and does not substantially exhibit any characteristic diffraction peak inherent to anhydrous crystalline ascorbic acid 2-glucoside. Examples of such a powder include those which are obtained by dissolving the above-identified powdered standard sample for determining the aforesaid analytical value $H_{100}$ in an appropriate amount of refined water, concentrating the solution, freeze-drying the concentrate, and drying in vacuo the resultant to give a moisture content of 2.0% or lower, when determined on the Karl Fischer method. With these treatments, it is known by experience that a powder consisting substantially of an amorphous form of ascorbic acid 2-glucoside is obtained. For reference, when analyzed with a computer software for the Hermans' method, a powder X-ray diffraction profile of the above-identified powdered standard sample containing ascorbic acid 2-glucoside, which consists substantially of an amorphous form of ascorbic acid 2-glucoside, gives an analytical value $H_0$, usually, ranging from about 7.3% to about 7.6%.

As a standard sample for determining the analytical value $H_0$, it goes without saying that an ascorbic acid 2-glucoside with a higher purity is preferable, however, the purity of ascorbic acid 2-glucoside of a standard sample used for determining the analytical value $H_0$, prepared from the standard sample used for determining the analytical value $H_{100}$ as mentioned above, is limited up to 99.1%, even though the purity of the standard sample used for determining the analytical value $H_{100}$ is distinctly as high as 99.9% or higher, as shown in the later-described Experiment 1-1. Thus, the purity of "a powdered standard sample containing ascorbic acid 2-glucoside, where the powdered standard sample consists substantially of an amorphous form of ascorbic acid 2-glucoside" is set to 99.1% or higher as mentioned above.

<Average Crystallite Diameter>

In general, a powder particle in a crystal-containing powder has been recognized as being constituted by single crystals, i.e., crystallites. The size of crystallite (crystallite diameter) in a crystalline powder is speculated to be reflected in its property. The term "an average crystallite diameter for anhydrous crystalline ascorbic acid 2-glucoside" as referred to as in the specification means an average of crystallite diameters calculated respectively in such a manner of subjecting a particulate composition containing anhydrous crystalline 2-glucoside to a powder X-ray diffraction analysis; selecting five diffraction peaks from among diffraction peaks detected on the obtained powder X-ray diffraction patterns, i.e., those of diffraction peaks (see the symbols "a" to "e" in FIG. 1) at diffraction angles (2θ) of 10.4° (Miller index (hkl):120), 13.2° (Miller index (hkl):130), 18.3° (Miller index (hkl):230), 21.9° (Miller index (hkl):060), and 22.6° (Miller index (hkl):131), which located in a relatively low-angle region that is to be least disruptive to diffraction peak width due to heterogeneous strain of crystallite, and which were well separated from other diffraction peaks; calibrating the respective half widths (full-widths at half maxima) and the diffraction angles based on the measured values determined when silicon ("Si640C", provided by NIST: National Institute of Standards and Technology, as a standard sample for X-ray diffraction) is used as a standard sample; and calculating respective averages of crystallite diameters with the Scherrer's equation shown in the following Formula [2]:

Formula [2]:

$$D = \frac{K\lambda}{\beta\cos\theta} \quad \text{[Equation 2]}$$

D: Size of crystallite (Å)
λ: Wavelength of X-ray (Å)
β: Diffraction linewidth (rad)
θ: Diffraction angle (°)
K: Constant (0.9 when a half-width (a full-width at half maximum) is used for β)

Since a commonly-used powder X-ray diffractometer has been installed with a computer software for calculating such crystallite diameters, an average crystallite diameter of anhydrous crystalline ascorbic acid 2-glucoside is relatively easily determined as long as a particulate composition containing anhydrous crystalline ascorbic acid 2-glucoside is available. Prior to the measurement for powder X-ray diffraction pattern, each test sample is brayed in a mortar and sieved with a 53 μm sieve to obtain a powder passed through the sieve for use.

<Reducing Power>

The term "a reducing power of the whole particulate composition" as referred to as in the specification means a percentage (%) of the reducing saccharide content to the total sugar content in a test sample, calculated by the following Formula [3] based on the reducing sugar content and the total sugar content in terms of D-glucose determined on the Somogyi-Nelson method and the anthrone-sulfuric acid method widely used in the art, where D-glucose is used as a standard substance.

$$\text{Reducing power } (\%) = \frac{\text{Reducing sugar content}}{\text{Total sugar content}} \times 100 \quad \text{Formula [3]}$$

<Particle Size Distribution>

In the specification, the particle size distribution of a particulate composition is determined as follows: Metal sieves with opening sizes of 425, 300, 212, 150, 106, 75 and 53 μm, produced by Kabushiki Gaisha Iida Seisaku-sho, Tokyo, Japan, which are compliant with Japanese Industrial Standards (JIS Z 8801-1), are accurately weighed, stacked in the above-identified order, and mounted on "R-1", a product name of a ro-tap sieving shaker, produced by Kabushiki Gaisha Tanaka Kagaku Kikai Seisaku-sho, Osaka, Japan. A prescribed amount of weighed sample is placed on the uppermost sieve (having an opening size of 425 μm) in the stacked sieves, followed by shaking the sieves for 15 min while keeping the stacked state. Thereafter, each of the stacked sieves was accurately weighed again, and the weight of the sample collected on each of the sieves was determined by subtracting the weight of each of the sieves before loading the sample from the weight of the corresponding sieve after shaking. Thereafter, particle size distributions are expressed by calculating the weight percentage (%) of each of the weights of the particulate compositions with respective particle sizes collected on each of the sieves to the weight of the sample loaded on the uppermost sieve.

<Production Yield of Ascorbic Acid 2-glucoside>

The term "a production yield of ascorbic acid 2-glucoside" as referred to as in the specification means a content (%) of ascorbic acid 2-glucoside, d.s.b., in an enzymatic reaction solution obtained by allowing enzymes such as CGTase to act on a solution containing either liquefied starch or dextrin and L-ascorbic acid.

<Ascorbic Acid 2-glucoside Content, d.s.b.>

The term "an ascorbic acid 2-glucoside content, d.s.b." means a percentage (%) by weight of ascorbic acid 2-glucoside to the total weight of a sample containing the same when calculated excluding moisture. For example, the meaning of an ascorbic acid 2-glucoside content, d.s.b., in a solution is a percentage by weight of ascorbic acid 2-glucoside to the total solid contents remained, excluding the water contained in the solution. While the meaning of an ascorbic acid 2-glucoside content, d.s.b., in a particulate composition is a percentage by weight of the weight of ascorbic acid 2-glucoside to the total weight of the particulate composition, when calculated by regarding the residue of the particulate composition excluding moisture contained therein as the total weight of the particulate composition.

<CGTase Activity>

The term "CGTase activity" as referred to as in the specification is defined as follows: To five milliliters of an aqueous substrate solution containing 0.3% (w/v) of a soluble starch, 20 mM acetate buffer (pH 5.5), and 1 mM calcium chloride, is added 0.2 ml of an appropriately diluted enzyme solution, and the resulting substrate solution is kept at 40° C., and sampled at 0 min and 10 min after initiating the enzymatic reaction in respective amounts of 0.5 ml, followed by immediately adding 15 ml of 0.02 N sulfuric acid solution to each sample to suspend the enzymatic reaction. Each of the resulting sulfuric acid solutions is admixed with 0.2 ml of 0.1 N iodine solution to develop colors, and, after 10 min, the colored solutions are respectively measured for absorbance at a wavelength of 660 nm by an absorptiometer, followed by calculating CGTase activity using the following Formula [4] as a starch-hydrolyzing activity. One unit activity of CGTase is defined as the enzyme amount that completely diminishes the iodine color of 15 mg starch in a solution.

Formula [4]:

$$\text{Activity (unit/ml)} = \frac{Aa - Ab}{Aa} \times \frac{1}{0.2} \times (\text{dilution rate}) \qquad [\text{Equation 4}]$$

Note: "Aa" means the absorbance at a wavelength of 660 nm of a reaction solution at 0 min after initiating the enzymatic reaction.

"Ab" means the absorbance at a wavelength of 660 nm of a reaction solution at 10 min after initiating the enzymatic reaction.

<Isoamylase Activity>

The term "isoamylase activity" as referred to as in the specification is defined as follows: To three milliliters of an aqueous substrate solution containing 0.83% (w/v) of Lintner's soluble waxy corn starch and 0.1 M acetate buffer (pH 3.5) is added 0.5 ml of an appropriately diluted enzyme solution, and the resulting substrate solution is kept at 40° C. and sampled at 0.5 min and 30.5 min after initiating the enzymatic reaction in respective amounts of 0.5 ml, followed by immediately adding 15 ml of 0.02 N sulfuric acid solution to each sample to suspend the enzymatic reaction. Each of the resulting sulfuric acid solutions is admixed with 0.5 ml of 0.01 N iodine solution to develop colors at 25° C. for 15 min, and then the colored solutions are respectively measured for absorbance at a wavelength of 610 nm by an absorptiometer, followed by calculating isoamylase activity using the following Formula [5] as a starch-hydrolyzing activity. One unit activity of isoamylase is defined as an enzyme amount that increases the absorbance by 0.004 at a wavelength of 610 nm under the above measurement conditions.

Formula [5]:

$$\text{Activity (unit/ml)} = \frac{Aa - Ab}{0.004} \times (\text{dilution rate}) \qquad [\text{Equation 5}]$$

Note: "Aa" means the absorbance of a reaction solution at a wavelength of 610 nm.

"Ab" means the absorbance of a control solution at a wavelength of 610 nm.

<Pullulanase Activity>

The term "pullulanase activity" as referred to as in the specification is defined as follows: A 1.25% (w/v) aqueous pullulan (a reagent for pullulanase activity, commercialized by Hayashibara Biochemical Laboratories, Inc., Okayama, Japan) solution is provided as an aqueous substrate solution. Four milliliters of the aqueous substrate solution and 0.5 ml of 0.05 M citric acid-phosphate buffered saline (pH 5.8) were placed in a test tube and preheated to 30° C. To the test tube was added 0.5 ml of an enzyme solution, which had been appropriately diluted with 0.01 M acetate buffer (pH 6.0) and the resulting substrate solution was incubated at 30° C. and sampled in respective amounts of 0.5 ml at 0.5 min (a control solution) and 30.5 min (a reaction solution), followed by promptly adding each of the sampled solutions to two milliliters of the Somogyi copper solution to suspend the reaction, subjecting each of the resulting solution to the Somogyi-Nelson method, determining the absorbance of each solution at a wavelength of 520 nm by an absorptiometer to measure the formed reducing power, and calculating the value as a pullulan-decomposing activity by the following Formula [6]. One unit activity of pullulanase is defined as an enzyme amount that releases a reducing power corresponding to one micromole of maltotriose per minute.

Formula [6]:

$$\text{Activity (unit/ml)} = \frac{Aa - Ab}{Ac} \times 100 \times \frac{5}{0.5} \times \frac{1}{180} \times \frac{1}{30} \times (\text{dilution rate}) \qquad [\text{Equation 6}]$$

Note: "Aa" means the absorbance of a reaction solution at a wavelength of 520 nm.

"Ab" means the absorbance of a control solution at a wavelength of 520 nm.

"Ac" means the absorbance of a standard solution at a wavelength of 520 nm.

D-Glucose (100 μg/ml) is used for a standard solution.

<Controlled Cooling Method>

The term "a controlled cooling method" as referred to as in the specification means a method for precipitating crystals by "a controlled cooling" and means a cooling method where the liquid temperature "T" at the time "t" is basically expressed by the following Formula [7], wherein "τ" is the operation time established for a crystallization step, "$T_0$" is the liquid temperature at the initiation of crystallization, and "$T_f$" is the targeted liquid temperature at the termination of crystallization.

Formula [7]:

$$T=T_0-(T_0-T_f)(t/\tau)^3 \qquad [\text{Equation 7}]$$

Figure 6:
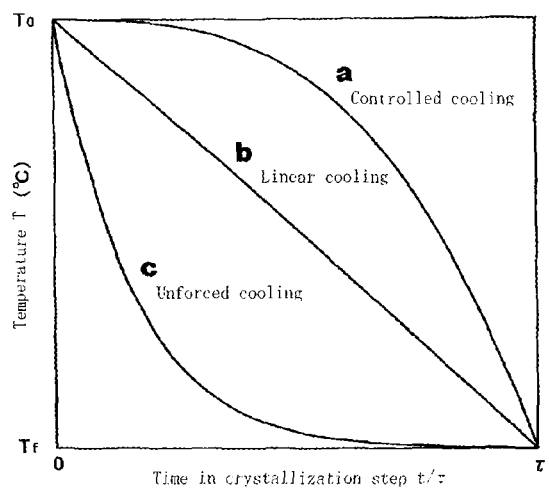
FIG. 6 is a figure of cooling patterns.

When a controlled cooling method is expressed more concretely (schematically) with a graph, it is expressed with "a" in FIG. 6, wherein the abscissa axis corresponds to the operation time established as a crystallization step and the longitudinal axis corresponds to the liquid temperature in crystallization. As shown in the symbol "a" in FIG. 6, according to a controlled cooling method, the liquid temperature gradually decreases in the early phase of crystallization at which the temperature is relatively high but it promptly decreases in the later phase at which the liquid temperature has decreased to some extent. Accordingly, the liquid temperature "$T_m$" at the time of t=τ/2, i.e., at the middle point of crystallization step is maintained at least on the connection of $T_m>[(T_0-T_f)/2+T_f]$ (or the temperature change at the middle point of crystallization step becomes less than 50% of the total temperature change). In the changing pattern of the liquid temperature against time, the controlled cooling method is clearly distinguished from both a linear cooling method (the symbol "b" in FIG. 6) where the liquid temperature linearly decreases with the time "τ" from the liquid temperature $T_0$ to $T_f$, and a usual unforced cooling method (the symbol "c" in FIG. 6) where the liquid temperature decreases exponentially and promptly in the early phase of crystallization at which the liquid temperature is relatively high but gradually decreases in the later phase of crystallization step at which the liquid temperature has been lowered. To alter the liquid temperature "T" as a function of the time "t" represented in the above Formula [7], for example, a commercialized general-purpose programmed constant circulator for crystallization system, etc., can be used.

When such a controlled cooling method is applied for crystallization step, after the addition of seed crystals of ascorbic acid 2-glucoside, the reduction of the liquid temperature is gradually carried out in the early phase of crystallization, and therefore a prompt increment of the supersaturation degree of ascorbic acid 2-glucoside and the formation of a secondary crystal nucleation by cooling are both inhibited and the growth of crystals from the added seed crystals as crystal nuclei can be predominantly proceeded. Meanwhile, in the later phase of crystallization step at which crystals have been completely generated from the added seed crystals as crystal nuclei, the homogeneously formed crystals are allowed to grow all together by promptly decreasing the liquid temperature, and therefore it gives the merit that a controlled cooling method provides a massecuite containing crystals with a homogeneous particle size and a lesser amount of microcrystals. For reference, "controlled cooling method" is described in detail in "*Wakariyasui-Batch-Shoseki*" (Accessible Batch Crystallization), pp. 32-47, edited by Noriaki KUBOTA, published by The Society of Separation Process Engineers, Japan, published on Apr. 30, 2010.

<Pseudo-Controlled Cooling Method>

The term "a pseudo-controlled cooling method" as referred to as in the specification means literally a cooling-method being artificially resembled to the above-identified controlled cooling method, wherein the liquid temperature "T" is not strictly altered against the time "t" according to the above Formula [7], and more specifically it means a cooling method, wherein the liquid temperature "T" is allowed to linearly or stepwisely decrease against the time "t" in order to keep the variation ($T_0-T_m$) of the liquid temperature "T" at the point of "t=τ/2" to be at least 5% but less than 50% of the total temperature change ($T_0-T_f$), preferably, at least 10% but less than 30%, because, varying depending on the content of seed crystals, purity, concentration, and supersaturation degree of as$_0-T_m$) of the liquid temperature "T" at the point of "t=τ/2" to be at least 5% but less than 50% of the total temperature change ($T_0-T_f$), the liquid temperature "T" gradually decreases ascorbic acid 2-glucoside in a solution containing ascorbic acid 2-glucoside used in crystallization, it is preferable that crystal nuclei are almost completely generated at the operation time "t=τ/2" (at the middle point in crystallization step). In the case of allowing the liquid temperature "T" to linearly or stepwisely decrease against the time "t" so as to adjust the variation (Test the time "t" in the early phase of crystallization at which the liquid temperature is relatively high, while the liquid temperature "T" promptly decreases against the time "t" in the later phase of crystallization step at which the liquid temperature has decreased to some extent. As a result, it may be somewhat inferior to the aforesaid controlled cooling method, however, a pseudo-controlled cooling method affords substantially the same merit as the controlled cooling method, wherein the pseudo-controlled cooling method enables to provide a massecuite containing crystals with a lesser amount of microcrystals and a homogeneous particle size.

Concretely speaking, for example, the liquid temperature "T" is allowed to linearly or stepwisely decrease against the time "t" in such a manner of dividing the operation time "τ" into at least two, preferably, at least three zones and then, in a zone of the early phase of crystallization step, allowing the thermal gradient in cooling to decrease gradually (to slow the cooling rate); and as it changes from the early phase or from the middle phase to the later phase, allowing the thermal gradient to increase (to fasten the cooling rate) to make the variation ($T_0-T_m$) of the liquid temperature "T" at the point of "t=τ/2" to be at least 5% but less than 50% of the total temperature change ($T_0-T_f$), preferably, at least 10% but less than 30%. In the case that the variation ($T_0-T_m$) of the liquid temperature "T" at the point of "t=τ/2" is at least 50% of the total temperature change ($T_0-T_f$), the cooling rate in the early phase of crystallization step is so fast as to possibly promptly increase the supersaturation degree by cooling to form the secondary crystal nuclei; while in the case of less than 5%, the cooling rate in the early phase of crystallization step is so slow as to get into the later phase of crystallization step, where a prompt cooling will start before completion of sufficiently forming crystals from the added seed crystals as crystal nuclei. In any event, it becomes impossible to obtain a massecuite containing crystals with a lesser amount of microcrystals and a homogeneous particle size.

To conduct the controlled cooling method as described above, the liquid temperature "T" should be changed as a function of the time "t" represented in Formula [7], and an apparatus or a crystallizer, which can control the liquid temperature by a preset program, is essential; however, according to a pseudo-controlled cooling method, the liquid temperature "T" can be linearly or stepwisely decreased against time "t" so as to adjust the variation $(T_0-T_m)$ of the liquid temperature "T" at the point of "t=τ/2" to a level of at least 5% but less than 50% of the total temperature change $(T_0-T_f)$, preferably, at least 10% but less than 30% so that such a pseudo-controlled cooling method has the merit that it can be relatively easily conducted even in the case that there is no facility that controls the liquid temperature accurately.

2. Particulate Composition Containing Anhydrous Crystalline Ascorbic Acid 2-glucoside Obtained by the Process of the Present Invention The following explain the particulate composition containing anhydrous crystalline ascorbic acid 2-glucoside obtained by the process of the present invention.

<Contents of Ascorbic Acid 2-glucoside and of Other Impurities>

As described above, the particulate composition containing anhydrous crystalline ascorbic acid 2-glucoside obtained by the process of the present invention is the one which contains ascorbic acid 2-glucoside in a content of, on a dry solid basis, over 98.0% but below 99.9%. In a preferred embodiment, the above particulate composition contains L-ascorbic acid and/or D-glucose derived from the materials and has a reducing power of over 0% but below 1%. As well known, since L-ascorbic acid and D-glucose have a reducing power and they induce brown coloration when heated in the presence of a compound with an amino group intramolecularly such as amino acids and proteins, these substances are not preferably incorporated into anhydrous crystalline ascorbic acid 2-glucoside as a product. However, for example, in the case of producing a particulate composition containing anhydrous crystalline ascorbic acid 2-glucoside through a step of allowing an enzyme such as CGTase to act on a solution containing either liquefied starch or dextrin and L-ascorbic acid, by a greater or less amount, both intact L-ascorbic acid and D-glucose derived from the material liquefied starch or dextrin are inevitably incorporated as reaction concomitants into a particulate composition containing anhydrous crystalline ascorbic acid 2-glucoside as a product. For example, since, in a conventional quasi-drug-grade powder, the total content of the L-ascorbic acid and D-glucose contained therein could even reach about one percent, d.s.b., an unexpected brown coloration could have been induced when the powder is used as a food material.

In the process according to the present invention, an inevitably inescapable incorporation of L-ascorbic acid and/or D-glucose is accepted and, in a particulate composition containing anhydrous crystalline ascorbic acid 2-glucoside, the reducing power of the whole particulate composition is regulated to below 1%, and particularly, over 0% but below 1%. As shown in the later-described experiment, in the case of producing a particulate composition containing anhydrous crystalline ascorbic acid 2-glucoside by the process according to the present invention, the reducing power of the whole particulate composition can be easily adjusted to over 0% but below 1%. Even though the particulate composition contains L-ascorbic acid and/or D-glucose, it does not substantially induce brown coloration even when heated in the presence of a compound with an amino group intramolecularly such as amino acids and proteins, whenever the reducing power of the whole particulate composition is over 0% but below 1%. Thus, a particulate composition containing anhydrous crystalline ascorbic acid 2-glucoside, which contains L-ascorbic acid and/or D-glucose and has a reducing power of the whole particulate composition of over 0% but below 1%, has the merit that it can be admixed with food products, cosmetics, quasi-drugs, and pharmaceuticals in general without fear of causing coloration or color change. Additionally, in the case of the reducing power of the whole particulate composition being below 1%, the content of L-ascorbic acid contained therein is not higher than 0.1%, d.s.b.

The particulate composition containing anhydrous crystalline ascorbic acid 2-glucoside, obtained by the process of the present invention, contains L-ascorbic acid in a content of not higher than 0.1%, d.s.b., particularly, over 0% but not higher than 0.1%. As L-ascorbic acid has been used in food products, etc., as an antioxidant or deoxidant, it is highly susceptible to react with oxygen. Thus, it is considered that, when heated in the coexistence of a compound with an amino group(s) intramolecularly, L-ascorbic acid not only induces brown coloration but deeply relates to the coloration of the particulate composition containing L-ascorbic acid per see. Actually, as shown in the later-described experiment, a quasi-drug-grade powder contains about 0.20 of L-ascorbic acid, and, based on the finding of the present inventors, such a quasi-drug-grade powder often causes a phenomenon that it in itself colors pale brown when stored for a relatively long period of time in the above-mentioned product form. On the contrary, in the case of the content of L-ascorbic acid in the particulate composition containing anhydrous crystalline ascorbic acid 2-glucoside being over 0% but not higher than 0.1%, the particulate composition per se has no fear of being colored pale brown even when stored for a relatively long period of time in a product form similar to that of a quasi-drug-grade powder. According to the process of the present invention, it can be relatively easily make the content of L-ascorbic acid in a particulate composition containing anhydrous crystalline ascorbic acid 2-glucoside to a level of over 0% but not higher than 0.1% without increasing the production cost by sequentially employing a column chromatography using an anion-exchange resin for removing saccharides such as D-glucose and a column chromatography using a cation-exchange resin or a porous-exchange resin in the purification step, particularly, in the case of using a simulated-moving-bed column chromatography as a column chromatography using a cation-exchange resin.

<Degree of Crystallinity and Average Crystallite Diameter>

The particulate composition containing anhydrous crystalline ascorbic acid 2-glucoside obtained by the process of the present invention has a degree of crystallinity for anhydrous crystalline ascorbic acid 2-glucoside of at least 90%, when calculated based on the powder X-ray diffraction profile of the particulate composition, and has an average crystallite diameter of at least 1,400 Å but less than 1,710 Å. As shown by the following experiments, the particulate composition containing anhydrous crystalline ascorbic acid 2-glucoside of the present invention, which has the above levels of degree of crystallinity and average crystallite diameter, has substantially the same level of purity of ascorbic acid 2-glucoside, i.e., the content of ascorbic acid 2-glucoside, d.s.b, or does not reach the purity of ascorbic acid 2-glucoside as in a reagent-grade powder, however, it has characteristics of that it significantly, more hardly cakes compared to a quasi-drug-grade powder and, compared to a reagent-grade powder, it has a superior solubility in hydrophilic solvents widely used in cosmetics and quasi-drugs.

<Particle Size Distribution>

In a preferred embodiment of the particulate composition containing anhydrous crystalline ascorbic acid 2-glucoside obtained by the process of the present invention, it contains particles with a particle size of less than 150 µm in a content of 70% or more of the whole particulate composition, and contains those with a particle size of 53 µm or more but less than 150 µm in a content of 40 to 60% of the whole particulate composition. Since the particulate composition containing anhydrous crystalline ascorbic acid 2-glucoside of the present invention can be, for example, easily controlled within the above-identified particle size distribution required for materials for food products, etc., it has the merit that it can be used as a material for food products, food additives, cosmetics, quasi-drugs, or pharmaceuticals similarly as conventional ones without altering any conventional production steps or material regulations.

3. Process for Producing the Particulate Composition Containing Anhydrous Crystalline Ascorbic Acid 2-glucoside of the Present Invention The following explain the process for producing the particulate composition containing anhydrous crystalline ascorbic acid 2-glucoside of the present invention.

The process for producing the particulate composition containing anhydrous crystalline ascorbic acid 2-glucoside of the present invention basically contains the following steps (a) to (e):

(a) a step of allowing CGTase to act on a solution containing either liquefied starch or dextrin and L-ascorbic acid, and then allowing glucoamylase to act on the resulting mixture to form ascorbic acid 2-glucoside and to obtain a solution containing ascorbic acid 2-glucoside as a reaction mixture after glucoamylase treatment in an ascorbic acid 2-glucoside production yield of at least 27%, (b) a step of purifying the solution containing ascorbic acid 2-glucoside to give an ascorbic acid 2-glucoside content of over 86% by weight, d.s.b.;

(c) a step of precipitating anhydrous crystalline ascorbic acid 2-glucoside from the purified solution with an ascorbic acid 2-glucoside content of over 86% by weight, d.s.b., by a controlled cooling method or pseudo-controlled cooling method;

(d) a step of collecting the precipitated anhydrous crystalline ascorbic acid 2-glucoside; and (e) a step of ageing, drying, and optionally pulverizing the collected anhydrous crystalline ascorbic acid 2-glucoside without dissolving and recrystallizing it to obtain a particulate composition containing anhydrous crystalline ascorbic acid 2-glucoside, which contains ascorbic acid 2-glucoside in a content of, on a dry solid basis, over 98.0% by weighty but below 99.9% by weight, and has a degree of crystallinity for anhydrous crystalline ascorbic acid 2-glucoside of at least 90%, when calculated based on the profile of powder X-ray diffraction analysis of the particulate composition.

The following explain each step:

<Step (a)>

Step (a) is for increasing the production yield of ascorbic acid 2-glucoside in a reaction solution to a level of at least 27% by allowing CGTase to act on a solution containing either liquefied starch or dextrin and L-ascorbic acid and then allowing glucoamylase to act on the resulting mixture. The materials and enzymes used are explained first and then the enzymatic reactions employed are explained.

A. Materials and Enzymes Used (L-Ascorbic Acid)

Examples of the L-ascorbic acid used in the present invention include any form of a hydroxy acid or a metal salt thereof such as alkaline metal salts and alkaline earth metal salts thereof, and even mixtures thereof can be used without difficulty.

(Liquefied Starch or Dextrin)

Examples of the liquefied starch or dextrin used in the present invention include those which are obtained by liquefying potato starch, sweet potato starch, tapioca starch, corn starch, wheat starch, etc., with a thermostable α-amylase. Upon conducting such enzymatic reaction, CGTase can be used in combination with, for example, a starch-debranching enzyme (s) such as isoamylase (EC 3.2.1.68) and pullulanase (EC 3.3.1.41) to debranch the branching sites of starch. Such liquefied starch and dextrin are suitable materials for an industrial-scale mass production compared to cyclodextrins and amyloses.

(CGTase)

Examples of the CGTase (EC 2.4.1.19) used in the present invention include any of those which are natural origins, those which are obtained by recombinant technology, and mutant enzymes obtained by introducing a modification of replacement, addition, or deletion of an amino acid (s) into natural or recombinant enzymes, without particular restriction to their origins and sources, as long as they form ascorbic acid 2-glucoside in a production yield of at least 27% when allowed alone or in combination with a starch-debranching enzyme to act on a solution containing either liquefied starch or dextrin and L-ascorbic acid and then glucoamylase is allowed to act on the resulting mixture.

According to the finding of the present inventors, CGTases, which form ascorbic acid 2-glucoside in a production yield of at least 27% when allowed alone or in combination with a starch-debranching enzyme to act on a solution containing either liquefied starch or dextrin and L-ascorbic acid and then glucoamylase is allowed to act on the resulting mixture, usually has the following common partial amino acid sequences represented by (a) to (d):

(a) Asn-Glu-Val-Asp-$X_1$-Asn-Asn;
(b) Met-Ile-Gln-$X_2$-Thr-Ala;
(c) Pro-Gly-Lys-Tyr-Asn-Ile; and
(d) Val-$X_3$-Ser-Asn-Gly-Ser-Val.
(Wherein $X_1$ means Pro or Ala, $X_2$ means Ser or Asp, and $X_3$ means Ser or Gly, respectively)

Examples of such CGTases include, for example, those which are natural or recombinant enzymes derived from microorganisms of the species *Geobacillus stearothermophilus* and *Thermoanaerobacter thermosulfurigenes*, and concrete examples of such include a CGTase derived from *Geobacillus stearothermophilus* Tc-91 strain, i.e., a CGTase having the amino acid sequence of SEQ ID NO: 1, CGTase mutants prepared by introducing a modification of replacement, addition, or deletion of an amino acid(s) by recombinant technology into the amino acid sequence of SEQ ID NO:1, i.e., a CGTase mutant having the amino acid sequence of SEQ ID NO: 4 or 5, a CGTase having the amino acid sequence of SEQ ID NO: 3 derived from a microorganism of the species *Thermoanaerobacter thermosulfurigenes*, and CGTase mutants thereof.

The above-identified *Geobacillus stearothermophilus* Tc-91 strain is the microorganism disclosed in Japanese Patent Kokai No. 63189/75 (Japanese Patent Publication No. 27791/78) applied for by the same applicant as the present invention, and it was once deposited domestically on Jul. 30, 1973, under the accession number of FERM-P 2225 and at present it has been deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, under the accession number of FERM BP-11273. For reference, it is known that the CGTase derived from *Geobacillus stearothermophilus* Tc-91 strain has a molecular weight of about 68,000 daltons and has a stronger saccharide-transferring action than CGTases derived from other microorganisms. The gene of the above-identified CGTase has been cloned and the amino acid sequence of a matured CGTase (the amino acid sequence of SEQ ID NO:1) has been determined based on the nucleotide sequence (the nucleotide sequence of SEQ ID NO:2) of the gene, and it has been known that there exist four conserved regions, recognized as commonly existing in enzymes classified as α-amylase family, on the amino acid sequence of the CGTase. The three-dimensional conformation of the CGTase has been already revealed by X-ray crystal structural analysis. The three catalytic residues of the CGTase, i.e., the $225^{th}$ aspartic acid (D225), the $253^{rd}$ glutamic acid (E253), and the $324^{th}$ aspartic acid (D324) in the amino acid sequence of SEQ ID NO:1 have been also revealed (see, for example, "*Kogyo-yo-Toshitsu-Koso-Handbook*" (Handbook of Industrial Enzymes for Saccharides), edited by Kodansha Scientific Ltd., Tokyo, Japan, published by Kodansha Ltd., Tokyo, Japan, pp. 56-63, 1999).

Concrete examples of a CGTase derived from a microorganism of the species *Thermoanaerobacter thermosulfurigenes* include "TORUZYME 3.0L", a product name of an enzyme produced as a recombinant enzyme of the CGTase derived from the above microorganism, commercialized by Novozymes Japan Ltd., Tokyo, Japan. Physicochemical properties and amino acid sequence of a CGTase derived from a microorganism of the species *Thermoanaerobacter thermosulfurigenes* have been also revealed.

(Starch-Debranching Enzyme)

When CGTase is allowed to act on a solution containing either liquefied starch or dextrin and L-ascorbic acid, a starch-debranching enzyme can be used in combination to increase the production yield of ascorbic acid 2-glucoside. As a preferred starch-debranching enzyme, isoamylase is particularly preferable because it is easily handled in terms of its enzyme activity, substrate specificity, etc. Examples of such isoamylase include, for example, those which are derived from microorganisms of the species *Pseudomonas amyloderamosa*, *Bacillus* sp., *Flavobacterium* sp., and mutant isoamylases obtained by genetically modifying the genes of the above-identified microorganisms. "GODO-FIA", a product name of an isoamylase specimen produced by Godo Shusei Co., Ltd., Tokyo, Japan, can be used as an isoamylase derived from a microorganism of the species *Flavobacterium odoratum*.

Examples of pullulanase include those which are derived from microorganisms of the species *Bacillus* sp., *Bacillus acidopullulyticas*, *Klebsiella pneumoniae*, *Klebsiella aerogenes*, *Flavobacterium pennivorans*, and *Enterobacter aerogenes*.

<Glucoamylase>

Any glucoamylases (EC 3.2.1.3) can be used without specific restriction independently of their origins and sources and include those in the form of a natural enzyme and those obtained by recombinant DNA technology, as long as ascorbic acid 2-glucoside is formed when CGTase is allowed to act on a solution containing either liquefied starch or dextrin and L-ascorbic acid and then glucoamylase is allowed to act on the resulting mixture.

Since glucoamylase is usually added to an enzymatic reaction solution after the solution is heated to suspend the saccharide-transferring reaction by CGTase, desired are those which can exert an enzymatic activity sufficient for actual use at a relatively high temperature, for example, about 40° C. to about 60° C. so as to save the energy and time needed for cooling the enzymatic reaction solution after heating. When glucoamylase to be used contains α-glucosidase, the resulting ascorbic acid 2-glucoside formed will be hydrolyzed, and therefore glucoamylases substantially free from α-glucosidase are desirably used. Any glucoamylases can be used independently of their sources and purities as long as they fulfill the above requirements, for example, a commercialized glucoamylase preparation derived from a microorganism of the genus *Rhizopus* ("GLUCOZYME #20000", a product name of an enzyme commercialized by Nagase ChemteX Corp., Osaka, Japan); and an enzyme preparation derived from a microorganism of the genus *Aspergillus* ("GLUCZYME AF6", a product name of an enzyme commercialized by Amano Enzyme Inc., Aichi, Japan), can be preferably used.

B. Enzymatic Reactions

The following explain the saccharide-transferring reaction to L-ascorbic acid. CGTase is allowed to act on a solution, usually, an aqueous solution, containing either liquefied starch or dextrin and L-ascorbic acid. When CGTase is allowed to act on an aqueous solution containing either liquefied starch or dextrin and L-ascorbic acid, one or more D-glucose residues are transferred to the hydroxyl group at the C-2 position of L-ascorbic acid, resulting in forming ascorbic acid 2-glucoside with one D-glucose residue bound to the hydroxyl group at the above C-2 position, and other α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid, which have at least two D-glucose residues bound to the hydroxyl group at the above C-2 position.

CGTase is usually added to an aqueous solution, which has been usually prepared by dissolving either liquefied starch or dextrin and L-ascorbic acid in water to give a substrate concentration of 1 to 40%, in a content of 1 to 500 units/g substrate, followed by an enzymatic reaction at a pH of about 3 to about 10 and a temperature of 30 to 70° C. for at least six hours, preferably, about 12 to about 96 hours. Since L-ascorbic acid is susceptible to oxidation, the solution should preferably be kept under anaerobic or reducing conditions during the enzymatic reaction, while shielding light and optionally coexisting, for example, a reducing agent such as thiourea or hydrogen sulfide in the reaction solution.

The weight ratio, d.s.b., of either liquefied starch or dextrin and L-ascorbic acid in the solution should preferably be set to 8:2 to 3:7. When the ratio of L-ascorbic acid to liquefied starch or dextrin exceeds the above range, saccharide-transfer to L-ascorbic acid effectively proceeds; however, the production yield of ascorbic acid 2-glucoside is restricted by the initial concentration of L-ascorbic acid to stay in a relatively low level. While, when the ratio of L-ascorbic acid exceeds the above range, intact L-ascorbic acid will remain in a considerable amount and this is not preferable for an industrial-scale production. Accordingly, the above-identified ratio range is considered the best.

In addition to CGTase, in the case of using isoamylase as a starch-debranching enzyme, such isoamylase should preferably be allowed to act on either liquefied starch or dextrin in the coexistence with CGTase in a solution containing either liquefied starch or dextrin and L-ascorbic acid, wherein the amount of isoamylase to be added is usually 200 to 2,500 units/g substrate and it is enzymatically reacted at a temperature of 55° C. or lower, varying depending on the type, optimum temperature, and optimum pH of isoamylase used. When pullulanase is used as a starch-debranching enzyme, it can be used, usually, in an amount of 1 to 500 units/g substrate in accordance with the case of isoamylase.

After the enzymatic reaction with CGTase alone or along with a starch-debranching enzyme is completed as a whole, the resulting enzymatic reaction solution is instantly heated to inactivate the CGTase alone or along with the starch-debranching enzyme to suspend the enzymatic reaction(s), followed by allowing glucoamylase to act on the resulting enzymatic reaction solution. By the action of glucoamylase, a chain of two or more D-glucose residues bound to the hydroxyl group at the C-2 position of L-ascorbic acid is cleaved to transform α-glycosyl-L-ascorbic acids such as 2-O-α-maltosyl-L-ascorbic acid and 2-O-α-maltotriosyl-L-ascorbic acid into ascorbic acid 2-glucoside.

<Step (b)>

Step (b) is for purifying the solution containing ascorbic acid 2-glucoside obtained in the above Step (a) to increase the ascorbic acid 2-glucoside content to over 86%, d.s.b.; the solution containing ascorbic acid 2-glucoside obtained in Step (a) is decolored with an activated charcoal, etc., filtered, followed by desalting the resulting filtrate with a cation-exchange resin and applying the desalted solution to column chromatography to purify the solution to give an ascorbic acid 2-glucoside content of, on a dry solid basis, over 86%, preferably, to 88% or more. As a column chromatography used for such purification, basically, any column chromatographies can be used as long as they increase the ascorbic acid 2-glucoside in a solution to over 86%, d.s.b., however, preferred examples of such are a column chromatography using a cation-exchange resin or porous resin, which follows after a column chromatography using an anion-exchange resin for removing saccharides such as D-glucose. Examples of the desired anion-exchange resins to remove saccharides such as D-glucose include such as "AMBERLITE IRA411S" and "AMBERLITE IRA478RF" (both of which are commercialized by Rohm & Hass Company, Philadelphia, USA); and "DIAION WA30" (commercialized by Mitsubishi Chemical Corp., Tokyo, Japan). Examples of the desired cation-exchange resins to separate ascorbic acid 2-glucoside from L-ascorbic acid include "DOWEX 50WX8" (commercialized by Dow Chemical Co., Midland, USA); "AMBERLITE CG120" (commercialized by Rohm & Hass Company, Philadelphia, USA); "XT-1022E" (commercialized by Tokyo Organic Chemical Industries, Ltd., Tokyo, Japan); and "DIAION SK104" and "DIAION UBK 550" (both of which are commercialized by Mitsubishi Chemical Corp., Tokyo, Japan). Examples of the desired porous resins include such as "TOYOPEARL HW-40" (commercialized by Tosoh Corp., Tokyo, Japan); and "CELLFINE GH-25" (commercialized by Chisso Corp., Tokyo, Japan). In the case of conducting a column chromatography using a cation-exchange resin or porous resin, preferable conditions are as follows: The solid concentration of a material solution to be fed to a column is about 10 to about 50%, d.s.b., the load volume to a resin is about 1/1,000- to about 1/20-fold of a wet resin volume, and refined water in an amount roughly equal to the wet resin volume is fed to the column at a linear velocity of 0.5 to 5 m/hour. Among which, in the case of using a simulated-moving-bed column chromatography as a column chromatography using a cation-exchange resin, such a column chromatography is preferable because it increases the purity of ascorbic acid 2-glucoside in the resulting purified product and reduces concomitants such as L-ascorbic acid and D-glucose, particularly, it reduces the L-ascorbic acid content and provides a particulate composition containing anhydrous crystalline ascorbic acid 2-glucoside with an L-ascorbic acid content of as low as 0.1% or lower, d.s.b. For reference, varying depending on operation temperature and predetermined flow rate, preferable elution conditions for a simulated-moving-bed column chromatography, where a cation-exchange resin is used as a packing material, are as follows: The concentration of a solution, containing ascorbic acid 2-glucoside, fed to the above column chromatography is 60% or lower; the load volume of a solution containing ascorbic acid 2-glucoside is 1/20-fold by volume or lower of the wet resin volume; and the volume of refined water used as an eluent is up to 30-folds by volume, usually, about 3- to about 20-folds by volume of the above load volume.

When the ascorbic acid 2-glucoside content, d.s.b., in the solution is 86% or lower, it is difficult to obtain a particulate composition containing anhydrous crystalline ascorbic acid 2-glucoside having a degree of crystallinity for anhydrous crystalline ascorbic acid 2-glucoside of at least 90%, even when passed through the follow-up Steps (c) to (e). The reason is speculated that, when the ascorbic acid 2-glucoside content, d.s.b., in the solution is 86% or lower, the purity of ascorbic acid 2-glucoside in the resulting particulate composition containing anhydrous crystalline ascorbic acid 2-glucoside, obtained through the subsequent steps, is relatively low and this hinders the smooth crystallization thereof.

The solution that has been purified to give an ascorbic acid 2-glucoside content of, on a dry solid basis, over 86%, preferably, 88% or more is concentrated up to give a prescribed concentration, usually, a concentration of about 65 to about 85% of ascorbic acid 2-glucoside, prior to the crystallization step for anhydrous crystalline ascorbic acid 2-glucoside. The temperature of the concentrate is usually controlled to about 30 to about 45° C. The concentrate with these concentration and temperature corresponds to an ascorbic acid 2-glucoside containing solution with a supersaturation degree of 1.05 to 1.50.

<Step (c)>

Step (c) is for precipitating anhydrous crystalline ascorbic acid 2-glucoside from a solution containing over 86%, preferably, 88% or more, d.s.b., of ascorbic acid 2-glucoside by a controlled cooling method or pseudo-controlled cooling method; the solution containing ascorbic acid 2-glucoside, which has been previously purified and concentrated to give a prescribed purity and concentration and controlled to a prescribed temperature in Step (b), is transferred to a crystallizer, admixed with 0.1 to 5% (w/v), preferably, 0.5 to 2% (w/v) of seed crystals of anhydrous crystalline ascorbic acid 2-glucoside, and stirred gently, followed by gradually decreasing the liquid temperature in the early phase of crystallization step and promptly decreasing the liquid temperature in the later phase of crystallization step by a controlled cooling method or pseudo-controlled cooling method to effect crystallization. Although the time required for crystallization varies depending on the content of seed crystals of ascorbic acid 2-glucoside to be added, for example, in the case of a pseudo-controlled cooling method, the total time required for crystallization can be divided into at least two zones, preferably, at least three zones, wherein in each zone the liquid temperature is allowed to roughly decrease in a linear fashion against the time, the liquid temperature "T" should preferably be decreased linearly or stepwisely against the time "t" in such a manner of allowing the variation ($T_0-T_m$) of the liquid temperature "T" at the point of the operation time "t=τ/2" (at the middle point of the crystallization step) to be at least 5% but less than 50%, preferably, at least 10% but less than 30% of the total temperature change ($T_0-T_f$). For example, when crystals are precipitated by cooling the solution containing ascorbic acid 2-glucoside from 40° C. to 15° C. over 48 hours, the cooling time can be divided into two zones of 36 and 12 hours, where the solution is preferably cooled from 40° C. to 30° C. over 36 hours and then cooled from 30° C. to 15° C. over 12 hours, or the solution is also preferably cooled from 40° C. to 35° C. over 30 hours and then cooled from 35° C. to 15° C. over 18 hours. More preferably, the cooling time can be divided into three zones of 24, 12 and 12 hours, where the solution is preferably, successively cooled from 40° C. to 35° C. over 24 hours in the first zone, cooled from 35° C. to 27.5° C. over 12 hours in the next zone, and then cooled from 27.5° C. to 15° C. over 12 hours in the last zone.

In this way, according to a controlled cooling method or pseudo-controlled cooling method, a massecuite, which hardly generates microcrystals of anhydrous crystalline ascorbic acid 2-glucoside and contains crystals with a substantially homogeneous crystalline diameter, can be obtained, compared to a crystallization method that unforcedly cools the solution without controlling the temperature. As described later, the obtained particulate composition containing anhydrous crystalline ascorbic acid 2-glucoside has the characteristic features of having both a higher purity of ascorbic acid 2-glucoside and a higher degree of crystallinity for anhydrous crystalline ascorbic acid 2-glucoside that is to be an important index for caking compared to a powder obtained by an unforced cooling method. In the case of a controlled cooling method or pseudo-controlled cooling method, it has a merit of obtaining a particulate composition with a more homogeneous particle size distribution than a powder obtained by a crystallization method of unforced cooling.

<Step (d)>

This step is for collecting the crystallized anhydrous crystalline ascorbic acid 2-glucoside from the massecuite obtained in the crystallization step (c) according to a conventional solid-liquid separation. The collected anhydrous crystalline ascorbic acid 2-glucoside is washed by spraying (showering) thereunto a small amount of refined water to remove an amorphous syrup adsorbed on the surface of the anhydrous crystalline ascorbic acid 2-glucoside. Preferable amount of refined water used for such spraying is usually at least 3% but up to 10% of the weight of the massecuite before centrifugation. More specifically, when the amount of refined water used for washing is less than 3%, sufficient washing may not be done and an amorphous syrup is still remained, resulting in a fear of not obtaining ascorbic acid 2-glucoside with a desired purity. On the contrary, when the amount of refined water used for washing exceeds 10%, the amount of anhydrous crystalline ascorbic acid 2-glucoside to be dissolved and removed by washing is increased and this results in a fear of decreasing the yield of crystals.

<Step (e)>

Step (e) is for ageing, drying, and optionally pulverizing the collected anhydrous crystalline ascorbic acid 2-glucoside without dissolving and recrystallizing it; the anhydrous crystalline ascorbic acid 2-glucoside collected by centrifugation is washed with a small amount of refined water such as deionized water and distilled water to wash off the impurities adsorbed on the surfaces of crystals. The content of water used for washing should not specifically be restricted, however, an excessive content of water dissolves the crystals per se, as well as the impurities, resulting in a reduction of the yield and an increment of the cost of water for washing. Therefore, the surfaces of the crystals are usually, preferably washed with water for washing in an amount of up to 30%, preferably, 15 to 25% of the weight of the crystals. The crystals thus washed are aged and dried by keeping them in an atmosphere with a predetermined temperature and humidity for a prescribed period of time to make into a particulate composition containing anhydrous crystalline ascorbic acid 2-glucoside. Although the product temperature of the particulate composition containing crystals, the relative humidity of atmosphere, and the time for ageing and drying in the ageing and drying steps should not specifically be restricted as long as a particulate composition with a desired degree of crystallinity is obtained, the product temperature and the relative humidity of atmosphere should preferably be kept at a temperature of 20 to 55° C. and a relative humidity of 60 to 90%, respectively, in the ageing and drying steps. The total time for the ageing and drying steps is preferably about 5 to about 24 hours. The particulate composition containing crystals, obtained through the ageing and drying steps, is unforcedly cooled to an ambient temperature, or it can be also advantageously cooled forcedly by blowing thereunto a clean air having about ambient temperature to give a product temperature of about ambient temperature. The crystalline powder thus obtained is made into a final product with or without optional pulverization.

The above Steps (a) to (e), excluding the crystallization step by a controlled cooling method or pseudo-controlled cooling method in the above Step (d), are basically the same as the production steps for quasi-drug-grade powders and they are free from any steps for recrystallization and repeated washing of crystals, which are both indispensable in the production steps for reagent-grade powders.

The powder thus obtained is a particulate composition containing anhydrous crystalline ascorbic acid 2-glucoside which contains ascorbic acid 2-glucoside in a content of, on a dry solid basis, over 98.0% but below 99.9%, has a degree of crystallinity for anhydrous crystalline ascorbic acid 2-glucoside of at least 90%, when calculated based on the powder X-ray diffraction profile of the particulate composition, more preferably, it contains ascorbic acid 2-glucoside in a content of, on a dry solid basis, over 98.0% but below 99.9%, has a degree of crystallinity for anhydrous crystalline ascorbic acid 2-glucoside of at least 90%, when calculated based on the powder X-ray diffraction profile of the particulate composition, contains L-ascorbic acid and/or D-glucose derived from the materials, contains L-ascorbic acid in a content of 0.1% or lower, d.s.b., and has a reducing power of the whole particulate composition of less than one percent. Since such a particulate composition hardly cakes even under the conditions where conventional quasi-drug-grade powders cake, it is a particulate composition containing anhydrous crystalline ascorbic acid 2-glucoside that significantly, more hardly cakes compared to conventional quasi-drug-grade powders. Further, compared to reagent-grade powders, the particulate composition has the merit that it has an advantageous solubility in hydrophilic solvents used widely in cosmetics and quasi-drugs.

Since the particulate composition containing anhydrous crystalline ascorbic acid 2-glucoside, produced by the process of the present invention, significantly, more hardly cakes compared to conventional quasi-drug powders, it has the advantageous merit that it can be incorporated with safeness into a single or plural other powdered materials for food products, food additives, cosmetics, quasi-drugs, and pharmaceuticals in the field of manufactures of food products including beverages, as well as of cosmetics, quasi-drugs, and pharmaceuticals, which are produced by production plants that are designed where powdered materials should be used on the premise.

The following experiments concretely explain the present invention:

<Experiment 1: Effect of the Degree of Crystallinity on the Caking of Particulate Composition Containing Anhydrous Crystalline Ascorbic Acid 2-glucoside>

Particulate compositions, which contain anhydrous crystalline ascorbic acid 2-glucoside with different degrees of crystallinity for anhydrous crystalline ascorbic acid 2-glucoside in the range of 0 to 100%, were prepared and tested for caking to examine the relationship between a degree of crystallinity and caking. The details are as follows:

<Experiment 1-1: Preparation of Test Samples>
<Test Sample 1>

"ASCORBIC ACID 2-GLUCOSIDE 999" (Code No.: AG124, Purity: at least 99.9%), a product name of a reagent-grade particulate composition containing anhydrous crystalline ascorbic acid 2-glucoside, consisting substantially of anhydrous crystalline ascorbic acid 2-glucoside, as a standard specimen, was used as Test sample 1.

<Test Sample 2>

A particulate composition consisting substantially of an amorphous form of ascorbic acid 2-glucoside, prepared by dissolving Test sample 1 in an adequate content of refined water, freeze-drying the resulting solution for three days, and drying the resultant in vacuo at a temperature of 40° C. or lower overnight, was used as a standard sample consisting substantially of an amorphous form of ascorbic acid 2-glucoside for use as "Test sample 2". Test sample 2 had a moisture content of 2.0% when measured on the Karl Fischer method.

<Test Samples 3 and 4>

As Test samples 3 and 4, those which have a degree of crystallinity for anhydrous crystalline ascorbic acid 2-glucoside lying between those of Test samples 1 and 2 were prepared by the following procedure: A particulate composition consisting of an amorphous form of ascorbic acid 2-glucoside, which had been prepared similar to Test sample 2, was spread over within metallic trays and partially crystallized by keeping them in a chamber with a constant temperature and humidity controlled at a temperature of 25° C. and a relative humidity of 90% for 24 or 72 hours to accelerate the crystallization. Successively, the metallic trays were taken out from the chamber and dried in vacuo at 38° C. overnight to obtain two types of particulate compositions, wherein the one with the keeping time of 24 hours in the constant temperature- and humidity-controlled-chamber was called "Test sample 3" and the other with the keeping time of 72 hours was called "Test sample 4". In addition, Test samples 3 and 4 were respectively enclosed in vials, sealed with caps, and preserved along with a desiccant in a desiccator under hermetical conditions until just before their analytical tests.

Experiment 1-2: Purities of Ascorbic Acid 2-glucoside and Degrees of Crystallinity of Test Samples 1 to 4

<Purities of Ascorbic Acid 2-glucoside>

The purities of ascorbic acid 2-glucoside of Test samples 1 to 4 were determined as follows: By using refined water, each of Test samples 1 to 4 was prepared into a 2% solution, which was then filtered with a 0.45-μm membrane filter. Each of the filtrates was subjected to high-performance liquid chromatography (HPLC) under the following conditions, followed by calculating the purity of ascorbic acid 2-glucoside, d.s.b., for each test sample based on a peak area appeared on a chromatogram by a differential refractometer. The results are in Table 1.

Analytical Conditions
  HPLC system: "LC-10AD", commercialized by Shimadzu Corp., Kyoto, Japan;
  Degasser: "DGU-12AM", commercialized by Shimadzu Corp., Kyoto, Japan;
  Column: "WAKOPAK WAKOBEADS T-330", $H^+$-form, commercialized by Wako Pure Chemical Industries, Osaka, Japan;
  Sample injection volume: 10 μl;
  Eluent: 0.01% (v/v) aqueous nitric acid solution;
  Flow rate: 0.5 ml/min;
  Temperature: 25° C.;
  Differential refractometer: "RID-10A", commercialized by Shimadzu Corp., Kyoto, Japan;
  Data processing apparatus: "CHROMATOPAK C-R7A", commercialized by Shimadzu Corp., Kyoto, Japan;

<Degree of Crystallinity>

The degrees of crystallinity of Test samples 1 to 4 were determined as follows: Analytical values for the degrees of crystallinity of respective Test samples 1 to 4 by the Hermans' method were determined by using "X' Pert PRO MPD", a product name of a commercially available reflected-light powder X-ray diffractometer commercialized by Spectris Co., Ltd., Tokyo, Japan, and using an analytical computer software exclusively installed in the diffractometer, based on a powder X-ray diffraction profile by a CuKα-ray (X-ray electric current: 40 mA, X-ray tube voltage: 45 kV, wavelength: 1.5405 Å), as a characteristic X-ray irradiated from a Cu target. Prior to the above analysis of degree of crystallinity by the Hermans' method, the granularity and the bending factor pre-set in the software were respectively adjusted to appropriate levels for obtaining a base-line judged as most preferable, while considering mutual overlapping peaks, diffraction intensity, and scattering intensity in respective powder X-ray diffraction patterns. The Hermans' method is described in detail in both P. H. Hermans and A. Weidinger, "*Journal of Applied Physics*, Vol. 19, pp. 491-506 (1948), and P. H. Hermans and A. Weidinger, "*Journal of Polymer Science*", Vol. 4, pp. 135-144, 1949.

The degree of crystallinity of each test sample was calculated by substituting the following data into the above Formula [1]: Hs as the value of degree of crystallinity of each test sample; $H_{100}$, the analytical value of that of Test sample 1; and $H_0$, the analytical value of that of Test sample 2. When analyzed by the Hermans' method, the analytical value of the degree of crystallinity of Test sample 1 (analytical value $H_{100}$) and that of Test sample 2 (analytical value $H_0$) were respectively 70.23% and 7.57%. The results are in Table 1 in parallel. The powder X-ray diffraction patterns of Test samples 1 and 2, as standard samples, are respectively shown in FIGS. 1 and 2.

Figure 2:
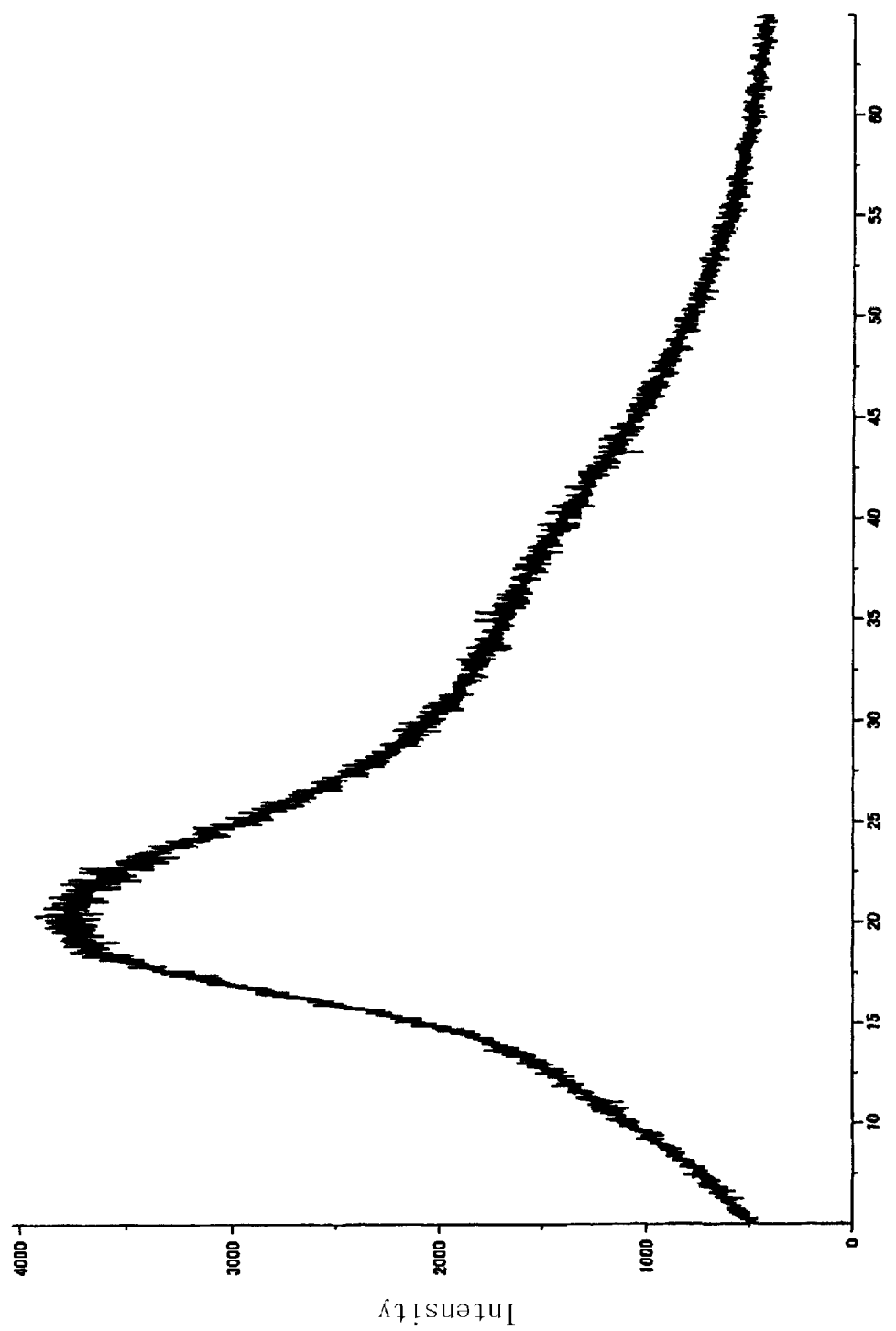
FIG. 2 is an example of powder X-ray diffraction pattern with a characteristic X-ray for a particulate composition containing ascorbic acid 2-glucoside, which substantially consists of amorphous ascorbic acid 2-glucoside.

As shown in FIG. 1, clear and sharp diffraction peaks specific to anhydrous crystalline ascorbic acid 2-glucoside were found in the range of diffraction angles (2θ) of 4 to 65° in the powder X-ray diffraction pattern of Test sample 1, but not any halo specific to an amorphous form of ascorbic acid 2-glucoside was found. While, as shown in FIG. 2, unlike the powder X-ray diffraction pattern of FIG. 1, halo specific to an amorphous form of ascorbic acid 2-glucoside was clearly found as a bunch of baseline in the powder X-ray diffraction pattern of Test sample 2, but no diffraction peak specific to anhydrous crystalline ascorbic acid 2-glucoside was found.

<Experiment 1-3: Powder X-ray Diffraction of Test Samples 1 and 2 Using Synchrotron Radiation>

This experiment was carried out to further confirm that Test samples 1 and 2 are respectively proper standard samples for determining the analytical values $H_{100}$ and $H_0$: These samples were subjected to a transmitted-light powder X-ray diffraction, which detects a weak diffraction and scattering signal, using a synchrotron radiation (called "radiation", hereinafter), as an X-ray source. The measuring condition was as follows:

<Measuring Condition>

Powder X-ray diffractometer: Model "PDS-16", a high-speed powder X-ray diffractometer (Debye Scherrer mode, camera length: 497.2 mm) commercialized by Kohzu Precision Co., Ltd., Kanagawa, Japan;

X-Ray source: "Beam line of Hyogo Prefecture (BL08B2)", a radiation light from bending electromagnet;

Wavelength: 0.7717 Å (16.066 keV);

Strength: $10^9$ photons/sec;

Measuring angle: 2 to 40°;

Exposure time: 600 sec;

Image recording: "IMAGING PLATE BAS-2040", an imaging plate commercialized by Fujifilm Corp., Tokyo, Japan; and Image analyzer: "BIO-IMAGE ANALYZER BAS-2500", commercialized by Fujifilm Corp., Tokyo, Japan.

The measurement was conducted by using "Beam line of Hyogo Prefecture (BL08B2)" placed in "SPring-8", a large synchrotron radiation facility, 1-1-1, Kouto, Sayo-cho, Sayo-gun, Hyogo, Japan.

Prior to the powder X-ray diffraction measurement, Test samples 1 and 2 were respectively ground in a mortar and sieved with a 53-µm mesh sieve. Then, each of the resulting particulate compositions passed through the sieve was homogeneously injected into "MARKTUBE No. 14", a product name of a capillary for powder X-ray diffraction (diameter: 0.6 mm, Lindeman glass), commercialized by Toho KK, Tokyo, Japan, to give an injected sample length of about 30 mm. Successively, the capillary was cut at the end terminal of the injected sample and the open end was sealed with an adhesive. Then, the capillary was fixed on a sample mount with a clay, and the sample mount was set to the powder X-ray diffractometer to give the longitudinal direction of the capillary perpendicularly against the optic axis of the diffractometer.

To remove adverse effect of the orientation of anhydrous crystalline ascorbic acid 2-glucoside on the powder X-ray diffraction profile, the measurement of the powder X-ray diffraction was carried out by allowing the sample mount to reciprocate at a uniform velocity toward the longitudinal direction of the capillary in a width of ±1.5 mm and at a time cycle of once/60 sec, and simultaneously allowing the sample mount to rotate at a uniform velocity around the rotational axis in the longitudinal direction of the capillary at a cycle of twice/sec.

In the processes of analyzing the powder X-ray diffraction profiles and preparing the powder X-ray diffraction patterns of Test samples 1 and 2, background signals inherent to the powder X-ray diffractometer were eliminated from each powder X-ray diffraction profile according to conventional manner for improving the measurement accuracy. The resulting powder X-ray diffraction patterns of Test samples 1 and 2 are respectively shown in FIGS. 3 and 4.

Figure 3:
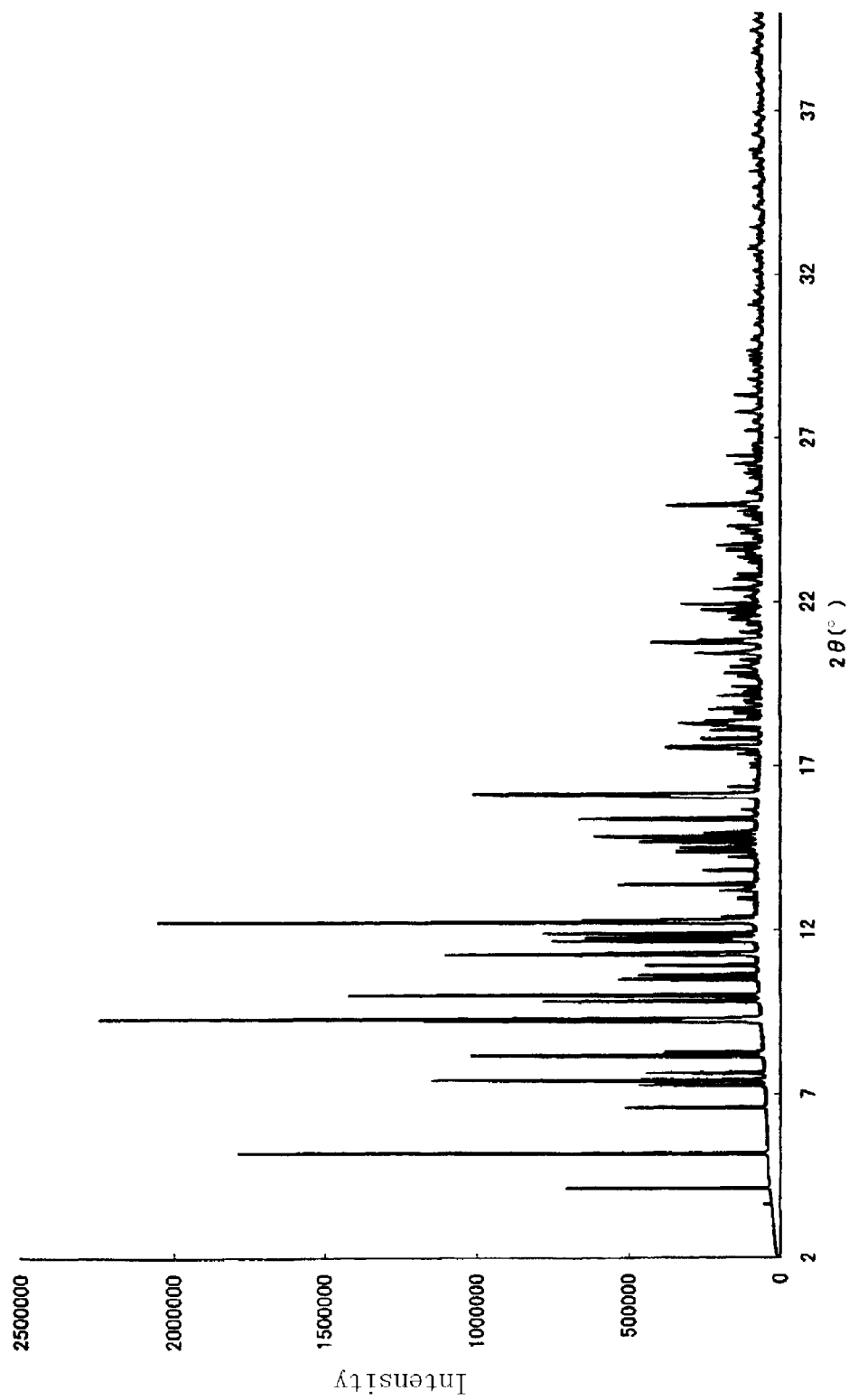
FIG. 3 is an example of powder X-ray diffraction pattern with a synchrotron radiation for a particulate composition containing anhydrous crystalline ascorbic acid 2-glucoside, which substantially consists of anhydrous crystalline ascorbic acid 2-glucoside.

As shown in FIG. 3, the powder X-ray diffraction peaks specific to anhydrous crystalline ascorbic acid 2-glucoside appeared clearly and sharply in the range of diffraction angles (2θ) of 2 to 40° for the powder X-ray diffraction pattern of Test sample 1, measured by using the synchrotron radiation. Comparing FIG. 3 with FIG. 1, since the wavelength of synchrotron radiation (0.7717 Å) was different from that of characteristic X-ray (1.5405 Å), each diffraction peak in FIG. 3 appeared by about a half diffraction angle (2θ) of each of the corresponding peaks in FIG. 1. The powder X-ray diffraction patterns in FIGS. 1 and 3, however, extremely well coincided with each other. While, the peak width at half height of each diffraction peak in FIG. 3 was evidently narrower than that in FIG. 1, and each diffraction peak in FIG. 3 showed a higher resolution than that in FIG. 1, although the strength of each diffraction peak in FIG. 3 was higher than that in FIG. 1 by nearly 100-folds. The powder X-ray diffraction pattern in FIG. 3 showed no halo specific to an amorphous form of ascorbic acid 2-glucoside, as shown in the following FIG. 4. The result indicates that the degree of crystallinity for anhydrous crystalline ascorbic acid 2-glucoside of Test sample 1 is extremely high, and Test sample 1 consists substantially of anhydrous crystalline ascorbic acid 2-glucoside.

Figure 4:
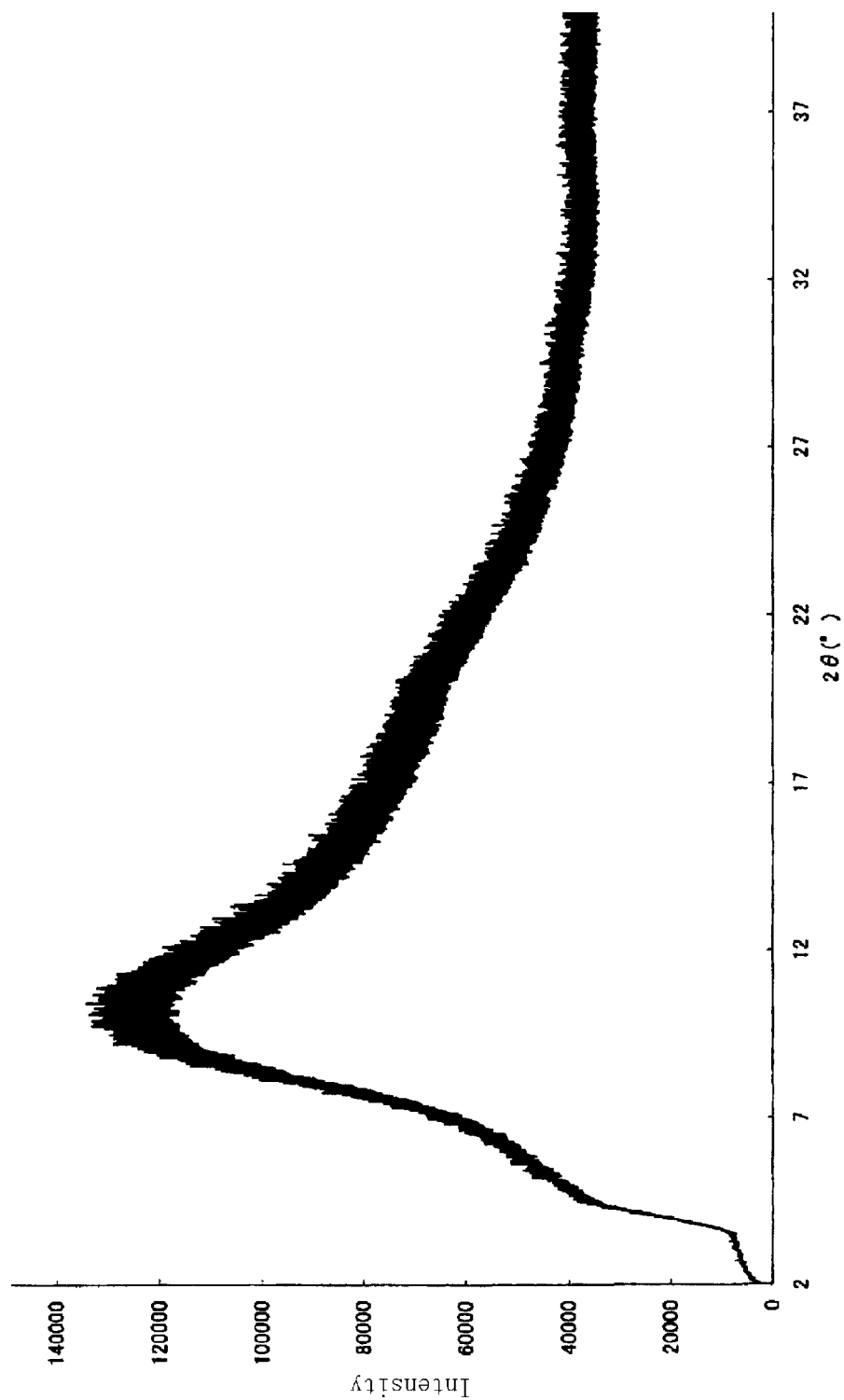
FIG. 4 is an example of powder X-ray diffraction pattern with a synchrotron radiation for a particulate composition containing ascorbic acid 2-glucoside, which substantially consists of amorphous ascorbic acid 2-glucoside.

As shown in FIG. 4, the powder X-ray diffraction pattern of Test sample 2, obtained by the powder X-ray diffraction of using the synchrotron radiation, showed a remarkable halo specific to an amorphous form of ascorbic acid 2-glucoside as a bunch of baseline but no diffraction peak specific to anhydrous crystalline ascorbic acid 2-glucoside was observed. This result indicates that Test sample 2 consists substantially of an amorphous form of ascorbic acid 2-glucoside.

The above results, obtained by using the synchrotron radiation as an X-ray source, support that Test samples 1 and 2 are proper standard samples for defining the analytical values $H_{100}$ and $H_0$, respectively, for use in Formula 1.

<Experiment 1-4: Caking Test>

The following experiment was performed to investigate the caking of respective Test samples 1 to 4: One gram aliquots of each of Test samples 1 to 4, prepared in Experiment 1-1, were separately filled into "FALCON TUBE 2059", a product name of a 14-ml polypropylene cylindrical tube (1.7 cm in diameter, 10 cm in height) having a hemispherical bottom shape and a cap, commercialized by Becton, Dickinson and Company, New Jersey, USA. The tubes were uprightly set to a tube rack and allowed to stand for 24 hours, after the tube rack was placed in "IC-410", a product name of an incubator commercialized Advantec Toyo Kaisha, Ltd., Tokyo, Japan, controlled at 50° C. After the incubation, the tubes were taken out from the incubator, followed by removing each cap, taking out each test sample from each tube to place it on a black-plastic-plane plate by turning the tubes upside down slowly, and macroscopically observing the conditions of the resulting test samples.

The degree of caking of each test sample was judged based on the following criteria: "Caked", (+): Sample clearly keeps the hemispherical shape of the bottom of the tube even when placed on the plate; "Slightly caked", (±): Sample slightly but distinguishably shows the hemispherical shape of the bottom of the tube; "Not caked" (−): Sample does not keep the hemispherical shape of the bottom of the tube. The results were shown in the column of "Caking" in Table 1.

TABLE 1

|  | Test sample | | | |
| --- | --- | --- | --- | --- |
|  | 1 | 2 | 3 | 4 |
| Purity of ascorbic acid 2-glucoside (%) | 99.9 | 99.1 | 99.1 | 99.1 |
| Degree of crystallinity (%) | 100.0 | 0.0 | 88.3 | 93.1 |
| Caking | − | + | + | − |

As shown in Table 1, Test sample 1, as a standard sample for defining the analytical value $H_{100}$ (degree of crystallinity: 100.0%), was judged as "Not caked" (−) because it collapsed and did not keep the hemispherical shape of the bottom of the tube, when taken out from the tube and placed on the plane plate. In contrast, Test sample 2, as another standard sample for defining the analytical value $H_0$ (degree of crystallinity: 0.0%), was clearly judged as "Caked" (+) because it still apparently kept the hemispherical shape of the bottom of the tube, even when taken out from the tube and placed on the plate. The hemispherical shape of Test sample 2 did not collapse when a slight vibration was merely given to the plate.

Test sample 3 with a degree of crystallinity of 88.3% still clearly kept the hemispherical shape of the bottom of the tube similar to Test sample 2, even when taken out from the tube and placed on the plane plate, and it was apparently judged as "Caked" (+). Test sample 4 with a degree of crystallinity of 93.1% instantly collapsed similar to Test sample 1 when taken out from the tube and placed on the plate, and it was judged as "Not caked" (−)

As described above, although Test samples 2 to 4 were prepared from Test sample 1 with an ascorbic acid 2-glucoside purity of 99.9%, the above-mentioned HPLC analysis showed that their purities of ascorbic acid 2-glucoside were up to 99.1%. The reason of this is not sure but it can be speculated that a slight content of ascorbic acid 2-glucoside might be lost by degradation or the like during its preparation for some reason.

The above results indicate that, in the case of particulate compositions containing at least 99.1%, d.s.b., of anhydrous crystalline ascorbic acid 2-glucoside, those with a higher degree of crystallinity for anhydrous crystalline ascorbic acid 2-glucoside tend to have a lower property of caking; and the facts that Test sample 3 with a degree of crystallinity of 88.3% was judged as "Caked" (+) and Test sample 4 with a degree of crystallinity of 93.1% was judged as "Not caked" (−) indicate that the threshold of changing from the judgment of "Caked" (+) to that of "Not caked" (−) under the above caking test lies between the degrees of crystallinity of 88.3% and 93.1%.

<Experiment 2: Relationship Between the Caking and the Degree of Crystallinity of Particulate Composition Containing Anhydrous Crystalline Ascorbic Acid 2-glucoside>

In this experiment, based on the results in Experiment 1, seven types of particulate compositions containing anhydrous crystalline ascorbic acid 2-glucoside, having a degree of crystallinity for anhydrous crystalline ascorbic acid 2-glucoside in the range of 0 to 100% and a purity of ascorbic acid 2-glucoside in the range of 99.1 to 99.9%, were used and tested for caking similarly as in Experiment 1 to investigate the relationship between the caking and the degree of crystallinity in more detail.

<Experiment 2-1: Preparation of Test Sample>

Particulate compositions of Test samples 5 to 9 in Table 2 were prepared by weighing Test samples 1 and 2, which had been prepared in Experiment 1-1, inappropriate contents, respectively, and mixing them to homogeneity. Table 2 shows the purities of ascorbic acid 2-glucoside and the degrees of crystallinity for anhydrous crystalline ascorbic acid 2-glucoside of Test samples 5 to 9, determined by the method disclosed in Experiment 1-2. The results of Test samples 1 and 2 in Table 2 were transcribed from Table 1.

<Experiment 2-2: Caking Test>

Test samples 5 to 9 were subjected to the caking test in Experiment 1-4. The results are shown in the column of "Caking" in Table 2. The results of "Caking" of Test samples 1 and 2 in Table 2 were transcribed from those described in Table 1.

TABLE 2

| Test sample | 1 | 2 | 5 | 6 | 7 | 8 | 9 |
|---|---|---|---|---|---|---|---|
| Purity of ascorbic acid 2-glucoside (%) | 99.9 | 99.1 | 99.8 | 99.7 | 99.6 | 99.5 | 99.4 |
| Degree of crystallinity (%) | 100.0 | 0.0 | 99.8 | 92.6 | 91.5 | 89.2 | 29.9 |
| Caking | − | + | − | − | − | ± | + |

As found in the results of Table 2, Test sample 9 with a degree of crystallinity of 29.9% was judged as "Caked" (+) and Test sample 8 with a degree of crystallinity of 89.2% was judged as "Slightly caked" (±). In contrast, Test samples 7, 6 and 5 with respective degrees of crystallinity of 91.5%, 92.6%, and 99.8% were all judged as "Not caked" (−) similar to Test sample 1. These results indicate that, among the particulate compositions containing anhydrous crystalline ascorbic acid 2-glucoside in an content of at least 99.1% but less than 99.9%, d.s.b., those with a degree of crystallinity for anhydrous crystalline ascorbic acid 2-glucoside of at least 90% do not cake under the conditions of this experiment.

<Experiment 3: Effect of the Purity of Ascorbic Acid 2-glucoside on the Degree of Crystallinity of Particulate Composition Containing Anhydrous Crystalline Ascorbic Acid 2-glucoside>

The antecedent experiments revealed that, in the particulate compositions containing anhydrous crystalline ascorbic acid 2-glucoside with an ascorbic acid 2-glucoside purity of as high as 99.1% or higher, there exist those with different degrees of crystallinity so that, in this experiment, the relationship between the degree of crystallinity of a particulate composition containing anhydrous crystalline ascorbic acid 2-glucoside and the purity of ascorbic acid 2-glucoside was further investigated. Further, the relationship between the purity and the caking of ascorbic acid 2-glucoside was investigated.

<Experiment 3-1: Preparation of Test Sample>

Test samples 10 to 15, having mutually different purities of ascorbic acid 2-glucoside as shown in Table 3, were prepared from an aqueous solution containing L-ascorbic acid and dextrin.

Four parts by weight of "PINEDEX #100", a product name of a dextrin commercialized by Matsutani Chemical Industries Co., Ltd., Hyogo, Japan, was dissolved in 15 parts by weight of water by heating. Then, three parts by weight of L-ascorbic acid was admixed with the solution. Successively, the solution was admixed with 100 units/g dextrin, d.s.b., of a CGTase derived from *Geobacillus stearothermophilus* Tc-62 strain and 250 units/g dextrin, d.s.b., of an isoamylase specimen, commercialized by Hayashibara Biochemical Laboratories, Inc., Okayama, Japan, and subjected to an enzymatic reaction while keeping the solution at a pH of 5.5 and a temperature of 55° C. for 50 hours to form ascorbic acid 2-glucoside. In addition, it can be speculated that α-glycosyl-L-ascorbic acids such as 2-O-α-maltosyl-L-ascorbic acid, 2-O-α-maltotriosyl-L-ascorbic acid, 2-O-α-maltotetraosyl-L-ascorbic acid, etc., would have been naturally formed in the reaction solution.

After inactivating the remaining enzymes by heating, the reaction solution was adjusted to pH 4.5, admixed with 50 units/g dextrin, d.s.b., of "GLUCZYME AF6", a product name of a glucoamylase specimen commercialized by Amano Enzymes Inc., Aichi, Japan, and subjected to an enzymatic reaction for 24 hours for hydrolyzing the above α-glycosyl-L-ascorbic acids up to ascorbic acid 2-glucoside and hydrolyzing the remaining concomitant oligosaccharides up to D-glucose. At this stage, the reaction solution contained ascorbic acid 2-glucoside in a production yield of 39%.

The reaction solution was heated to inactivate glucoamylase, decolored with an activated charcoal, filtered, subjected to a column of a cation-exchange resin ($H^+$-form) for desalting, and then subjected to an anion-exchange resin ($OH^-$-form) to absorb L-ascorbic acid and ascorbic acid 2-glucoside, followed by washing the resin with water to remove D-glucose and feeding 0.5 N hydrochloric acid solution to effect elution. The eluate was concentrated to give a solid content of about 50% and then subjected to a column chromatography using "DOWEX 50WX4" ($Ca^{2+}$-form), a product name of a strong-acid cation exchange resin commercialized by Dow Chemical Company. The concentrate was loaded on the column in a volume of about 1/50-fold of the wet resin volume, followed by feeding to the column refined water in a volume of 50-folds of the load volume of the concentrate at a linear velocity of 1 m/hour and fractionating the resulting eluate by 0.05-volume aliquots of the column volume. Thereafter, the composition of each fraction was measured on HPLC described in Experiment 1-2, and six fractions with an ascorbic acid 2-glucoside content of at least 80%, d.s.b., were concentrated in vacuo to give respective solid concentrations of about 76%. The resulting concentrates were respectively placed in a crystallizer, admixed with Test sample 1 in Experiment 1-1, as a seed crystal, in a content of two percent of each of the solid contents, d.s.b., followed by unforcedly cooling each concentrate from 40° C. to 15° C. over about two days while stirring gently to precipitate anhydrous crystalline ascorbic acid 2-glucoside.

Thereafter, according to a conventional manner, Test samples 10 to 15, shown in Table 3, were obtained by collecting crystals from each massecuite by a basket-type centrifuge, washing the crystals with a small content of distilled water, ageing and drying the washed crystals, blowing thereunto 25° C. air for 30 min to the aged and dried crystals for cooling, and pulverizing the resultants. "AA2G", a product name of a particulate composition containing anhydrous crystalline ascorbic acid 2-glucoside, as a conventional quasi-drug-grade powder, commercialized by Hayashibara Biochemical Laboratories, Inc., Okayama, Japan, was used as Test sample 16.

ascorbic acid 2-glucoside when actually stored, Test sample 1 obtained in Experiment 1-1, Test samples 10 to 15 obtained in Experiment 3-1, and Test sample 16 were subjected to a storage stability test which was designed by taking account of conditions, environment, and period of time for actual storage of a particulate composition containing anhydrous crystalline ascorbic acid 2-glucoside.

Ten kilogram aliquots of any of Test samples 1 and 10 to 16 were respectively weighed and placed in a polyethylene-double-bag (800 mm by 600 mm) for each test sample. Then, each bag was placed in a 18-liter steel can in such a manner of allowing the opening part of each bag to open and stand upright without closing the opening part, allowing the bags to stand without capping the steel cans, and storing for 45 days in a room away from a relatively high temperature and humidity. After 45 days storage, each polyethylene-double-bag enclosing any of the test samples was taken out from the cans, and the samples were taken out from the bags and placed on a black-plastic-plane-plate for macroscopic observation of their flowabilities and caked states.

The test samples were judged about their caking by the following criteria: "Caked" (+), clump (s) is/are detected in a test sample and the flowability of the test sample has lowered in comparison with that at the initiation of the test; and "Not caked" (−), no clump is detected in a test sample and the flowability of the test sample has not been changed in comparison with that at the initiation of the test. The storage form of each test sample in the storage stability test is the same as that of a quasi-drug-grade powder that is commercially distributed and stored, except for not closing the opening part of the bag with a rubber band, not putting in any desiccant, and being stored in a steel can without closing it with a lid. The above three differences were of those, which had been set as a storage environment for a storage test that was slightly harder than an actual storage environment, to expedite the test results. The results are in Table 3 in parallel.

As shown in Table 3, except for Test sample 2 consisting substantially of an amorphous form of ascorbic acid 2-glucoside and Test sample 16 as a quasi-drug-grade powder, the remaining Test samples 1 and 10 to 15 tend to increase their degrees of crystallinity for anhydrous crystalline ascorbic acid 2-glucoside as the increase of their purities of ascorbic

TABLE 3

| Test sample | 1 | 2 | 10 | 11 | 12 | 13 | 14 | 15 | 16 |
|---|---|---|---|---|---|---|---|---|---|
| Purity of ascorbic acid 2-glucoside (%) | 99.9 | 99.1 | 97.4 | 98.0 | 98.6 | 99.1 | 99.5 | 99.7 | 98.9 |
| Degree of crystallinity (%) | 100.0 | 0.0 | 88.7 | 89.0 | 91.6 | 94.8 | 99.4 | 99.5 | 88.9 |
| Caking | − | + | + | ± | − | − | − | − | ± |
| Storage stability | − | | + | + | − | − | − | − | + |

Test samples 1 and 2 as found in Table 3 were similar to those in Experiment 1-1, and their purities and degrees of crystallinity for anhydrous crystalline ascorbic acid 2-glucoside were transcribed from the antecedent experimental results. Test samples 10 to 16 were tested for caking by the method similarly as in Experiment 1-4. The results are in Table 3. The results of the caking tests for Test samples 1 and 2 as found in Table 3 were transcribed from Table 1 without any change.

<Experiment 3-2: Storage Stability Test>

To confirm that the caking test conducted in Experiment 1-4, etc., is a proper test for evaluating the caking of a particulate composition containing anhydrous crystalline acid 2-glucoside. In the caking test, Test samples 10 and 11 with respective ascorbic acid 2-glucoside purities of 97.4% and 98.0% were judged as "Caked" (+) or "Slightly caked" (±). On the contrary, Test samples 12 to 15 with ascorbic acid 2-glucoside purities of 98.6 to 99.7% were judged as "Not caked" (−). These results indicate that the threshold value of the purity of ascorbic acid 2-glucoside that influences on the caking lies at around 98.0% and they conclude that an ascorbic acid 2-glucoside purity of over 98.0% must be needed for obtaining a particulate composition containing anhydrous crystalline ascorbic acid 2-glucoside that is judged as "Not caked" (−).

No caking was observed in Test samples 12 to 15 similarly as in Test sample 1, though the purities of ascorbic acid 2-glucoside of Test samples 12 to 15 were 98.6% to 99.7%, which were almost the same levels as that of Test sample 16, a quasi-drug-grade powder, with a purity of 98.9%, and were significantly lower than that of Test sample 1, a reagent-grade powder consisting substantially of anhydrous crystalline ascorbic acid 2-glucoside. The degrees of crystallinity of Test samples 12 to 15 were 91.6% to 99.5% being as high as 90% or more, and Test sample 16, a quasi-drug-grade powder, had a degree of crystallinity of 88.9% being as low as less than 90%. From these results, it can be concluded that the degree of crystallinity for anhydrous crystalline ascorbic acid 2-glucoside should be made 90% or more to obtain a desired particulate composition containing anhydrous crystalline ascorbic acid 2-glucoside, which significantly, more hardly cakes compared to Test sample 16 as a quasi-drug-grade powder.

As shown in the bottom column of Table 3, Test samples 10 and 11 with respective ascorbic acid 2-glucoside purities of 97.4% and 98.0% were judged as "Caked" (+) even on a storage stability test, where they were stored for 45 days in bags in respective contents of 10 kg/bag along the lines of their actual commercialized product form. On the contrary, Test samples 12 to 15 with an ascorbic acid 2-glucoside purity of 98.6% to 99.7% were judged as "Not caked" (−) similar to the results in their caking tests. These facts indicate that the caking test as in Experiment 1-4, etc., is a proper test for evaluating the caking of a particulate composition containing anhydrous crystalline ascorbic acid 2-glucoside under an actual storage environment.

<Experiment 4: Relationship Between the Reducing Power and the Browning of Particulate Composition Containing Anhydrous Crystalline Ascorbic Acid 2-glucoside>

The test samples used in the precedent experiments were all particulate compositions containing anhydrous crystalline ascorbic acid 2-glucoside prepared from solutions containing ascorbic acid 2-glucoside obtained through a step of allowing CGTase to act on a solution containing L-ascorbic acid and an amylaceous substance. When employing such production process, the resulting particulate compositions will contain L-ascorbic acid and D-glucose as concomitants specific to the production process regardless of the content of such concomitants. Since both L-ascorbic acid and D-glucose have reducibility, particulate compositions containing anhydrous crystalline ascorbic acid 2-glucoside, varying depending on the content of L-ascorbic acid and D-glucose, may possibly cause unfavorable color change in the final products when used in products containing compounds with an amino group, such as proteins and amino acids. Among which, since L-ascorbic acid has a relatively high reactivity with oxygen, it is speculated that L-ascorbic acid must be a causative of inducing not only unfavorable color change in products using the same but undesired browning of a conventional quasi-drug-grade powder per se that was occasionally observed when stored for a relatively long period of time.

Accordingly, in this experiment, Test samples 1 and 12 to 16, which had been used in the antecedent Experiments, were examined for the relationship between the coloration and the total content of L-ascorbic acid plus D-glucose, the content of L-ascorbic acid, or the reducing power of the whole particulate composition by conducting an accelerated test on heat treatment according to the following procedures:

One hundred and fifty milligrams of each of the test samples was weighed and placed in a 10-ml test tube with a screw cap, and the test tubes in a closed condition of their opening parts with the screw caps were placed in "DRYING-OVEN SA310", a product name of an oven commercialized by Masuda Corp., Osaka, Japan, and heated at 80° C. for three days. Subsequently, after removing the screw caps from the test tubes, three milliliters of deionized water was added to each of the tubes to dissolve each sample. The resulting solutions were measured for absorbance at a wavelength of 400 nm using "UV-2400PC", a product name of a spectrophotometer commercialized by Shimadzu Corp., Kyoto, Japan. The degree of coloration caused by heating was judged based on the following two criteria: When the absorbance at a wavelength of 400 nm is less than 0.50, it is judged as "Not browned or substantially not browned" (−); and when the absorbance at a wavelength of 400 nm is 0.50 or higher, it is judged as "Browned" (+). The results are in Table 4.

The total content of L-ascorbic acid and D-glucose in each test sample was determined on HPLC described in Experiment 1-1. The reducing power of the whole particulate composition of each test sample was determined by measuring the contents of reducing sugar and total sugars by the Somogyi-Nelson method and the anthrone-sulfuric acid method generally used in the art, respectively, using D-glucose as a standard substance; and calculating the reducing power by substituting the data into the aforesaid Formula [3]. The total content of L-ascorbic acid and D-glucose, the content of L-ascorbic acid, and the reducing power of the whole particulate composition for each sample were as shown in Table 4.

TABLE 4

| Test sample | | 1 | 12 | 13 | 14 | 15 | 16 |
|---|---|---|---|---|---|---|---|
| Composition (%), d.s.b. | Ascorbic acid 2-glucoside | 99.9 | 98.6 | 99.1 | 99.5 | 99.7 | 98.9 |
| | Total content of L-ascorbic acid and D-glucose (L-Ascorbic acid) | 0.0 (0.0) | 0.2 (0.1) | 0.1 (<0.1) | 0.1 (<0.1) | 0.1 (0.0) | 0.3 (0.2) |
| | Others | 0.1 | 1.2 | 0.8 | 0.4 | 0.3 | 0.8 |
| Reducing power of the whole particulate composition (%) | | 0.05 | 0.98 | 0.86 | 0.2 | 0.12 | 1.12 |
| Browning property | | − | − | − | − | − | + |

As shown in Table 4, in particulate compositions containing anhydrous crystalline ascorbic acid 2-glucoside, the contents of both L-ascorbic acid and D-glucose in Test sample 1, which is a reagent-grade powder consisting substantially of anhydrous crystalline ascorbic acid 2-glucoside, were lower than their detection limits. On the contrary, L-ascorbic acid and/or D-glucose were/was detected in any of Test samples 12 to 15, as the particulate compositions containing anhydrous crystalline ascorbic acid 2-glucoside of the present invention, and Test sample 16 as a conventional quasi-drug-grade powder. In these powders, as evident from Test samples 12 to 15, when the total content of L-ascorbic acid and D-glucose was not higher than 0.2%, d.s.b., it was judged as "Not browned or substantially not browned" (−); while as evident from Test sample 16, when the total content of L-ascorbic acid and D-glucose reached 0.3%, d.s.b., it was judged as "Browned" (+). As for L-ascorbic acid which is considered to most deeply relate to the coloration of powders, those like Test samples 12 to 15, which contain L-ascorbic acid in a content of 0.1% or lower, d.s.b., were judged as "Not browned or substantially not browned" (−); while the one like Test sample 16, which has an L-ascorbic acid content reaching 0.2%, d.s.b., was judged as "Browned" (+). As already mentioned, since L-ascorbic acid has a relatively high reactivity with oxygen and relates to the browning of particulate compositions containing anhydrous crystalline ascorbic acid 2-glucoside, those with an L-ascorbic acid content of over 0% but not higher than 0.1%, d.s.b., are no need of apprehension of causing substantial browning even when stored for a relatively long period of time in the product form of a conventional quasi-drug-grade powder.

From the viewpoint of the reducing power, as evident from Test samples 12 to 15, those with a reducing power of the whole particulate composition of over 0% but below 1% were judged as "Not browned or substantially not browned" (−). On the contrary, as evident from Test sample 16, test samples with a reducing power of the whole particulate composition of over 1% were judged as "Browned" (+). These results were well coincident with the above results obtained by the judgement with an index of the total content of L-ascorbic acid and D-glucose.

The above results indicate that particulate compositions containing anhydrous crystalline ascorbic acid 2-glucoside with no fear of causing browning can be obtained by controlling the reducing powers of the whole particulate compositions to a level of over 0% but below 1% even though they inevitably contain L-ascorbic acid and/or D-glucose in a detectable level due to their production processes. Considering both the aspects of the browning of not only the final products prepared with the particulate compositions but the particulate compositions per se, the above results show that the contents of L-ascorbic acid in particulate compositions should preferably be over 0% but not higher than 0.1%, d.s.b.

<Experiment 5: Effect of Cooling Method in Crystallization on the Degree of Crystallinity of Particulate Composition Containing Anhydrous Crystalline Ascorbic Acid 2-glucoside>

To examine the effect of cooling method in crystallization on the degrees of crystallinity of particulate compositions containing anhydrous crystalline ascorbic acid 2-glucoside, the particulate compositions containing anhydrous crystalline ascorbic acid 2-glucoside in Table 5 (Test samples 17 to 22) were prepared by the following method. The production yield of ascorbic acid 2-glucoside in each enzymatic reaction solution was determined by the method in Experiment 1-2.

(1) Test Sample 17

Similarly as in the later-described Example for Reference 1, Test sample 17 as a particulate composition containing anhydrous crystalline ascorbic acid 2-glucoside was prepared except that, in the method of the later-described Example for Reference 1, the durations of actions of CGTase and isoamylase were suspended at 25 hours as a half-the-time as in Example for Reference 1, followed by purifying the enzymatic reaction solution to give an ascorbic acid 2-glucoside content of at least 86% and then concentrating in vacuo the solution containing ascorbic acid 2-glucoside to give a concentration of about 76%, transferring the resulting concentrate to a crystallizer with a jacket tank equipped around the crystallizer, precipitating crystals by a pseudo-controlled cooling method of gradually cooling the concentrate from 40° C. to 30° C. over 1.5 days, and then promptly cooling it from 30° C. to 15° C. over 0.5 day by controlling the temperature of the water in the jacket tank. The production yield of ascorbic acid 2-glucoside in the enzymatic reaction solution was 25.3%.

(2) Test Sample 18

Similarly as in Example 1, Test sample 18 as a particulate composition containing anhydrous crystalline ascorbic acid 2-glucoside was prepared except that, in the method of the later-described Example 1, the liquefied potato starch used as a material was replaced with "PINEDEX #100", a product name of a dextrin commercialized by Matsutani Chemical Industries Co., Ltd., Hyogo, Japan; and crystals were obtained by purifying the solution after enzymatic reactions, concentrating the purified solution under a reduced pressure, and unforcedly cooling the concentrate from 40° C. to 15° C. over about two days. The production yield of ascorbic acid 2-glucoside in the enzymatic reaction solution was 27.0%.

(3) Test Sample 19

Test sample 19 as a particulate composition containing anhydrous crystalline ascorbic acid 2-glucoside was prepared similarly as in Test sample 18, except that a solution after enzymatic reactions was transferred to a crystallizer with a jacket tank equipped around the crystallizer and crystallized by a pseudo-controlled cooling method of gradually cooling the solution from 40° C. to 30° C. over 1.5 days and then promptly cooling it from 30° C. to 15° C. over 0.5 day by controlling the temperature of the water in the jacket tank. The production yield of ascorbic acid 2-glucoside in the enzymatic reaction solution was 27.0%.

(4) Test Sample 20

Similarly as in Example 4, Test sample 20 as a particulate composition containing anhydrous crystalline ascorbic acid 2-glucoside was prepared except that, in the method of the later-described Example 4, a solution containing ascorbic acid 2-glucoside was concentrated to give a concentration of about 76% under a reduced pressure and the obtained solution with a temperature of 40° C. was transferred to a crystallizer and unforcedly cooled in such a manner of cooling the solution from 40° C. to 15° C. over about two days to precipitate crystals. The production yield of ascorbic acid 2-glucoside in the enzymatic reaction solution was 32.5%.

(5) Test Sample 21

Test sample 21 as a particulate composition containing anhydrous crystalline ascorbic acid 2-glucoside was prepared similarly as in Test sample 20 except that a solution after enzymatic reactions was transferred to a crystallizer with a jacket tank equipped around the crystallizer, followed by precipitating crystals by a pseudo-controlled cooling method of gradually cooling the solution from 40° C. to 30° C. over 1.5 days and then promptly cooling it from 30° C. to 15° C. over 0.5 day by controlling the temperature of the water in the jacket tank. The production yield of ascorbic acid 2-glucoside in the enzymatic reaction solution was 32.5%.

(6) Test Sample 22

Similarly as in Experiment 3-1, Test sample 22 as a particulate composition containing anhydrous crystalline ascorbic acid 2-glucoside was prepared except that, in the preparation method for test samples of Experiment 3-1, the enzymatic reactions by CGTase and isoamylase were suspended at 30 hours after initiating the enzymatic reactions, and the solution, which had been purified to give an ascorbic acid 2-glucoside content of 86.2%, was concentrated to give a concentration of about 76% under a reduced pressure, followed by transferring the resulting solution with a temperature of 40° C. to a crystallizer and cooling the solution by an unforced cooling method from 40° C. to 15° C. over about two days to precipitate crystals. The production yield of ascorbic acid 2-glucoside in the enzymatic reaction solution was 35.3%.

<Measurement for the Purity and the Degree of Crystallinity of Ascorbic Acid 2-glucoside>

According to a similar method as in Experiment 1-2, the purities and the degrees of crystallinity for anhydrous crystalline ascorbic acid 2-glucoside of Test samples 17 to 22 were determined.

<Average Crystallite Diameter>

The average crystallite diameters of Test samples 17 to 22 were measured by the following method. For the calculation by the above-described Formula [2], in the diffraction patterns, which had been prepared based on the powder X-ray diffraction profiles that had been used for determining the degree of crystallinity of each test sample, the half-widths and the diffraction angles (2θ) of five diffraction peaks detected at diffraction angles (2θ) of 10.4° (Miller index (hkl):120), 13.2° (Miller index (hkl):130), 18.3° (Miller index (hkl):230), 21.9° (Miller index (hkl):060), and 22.6° (Miller index (hkl):131), which correspond to the symbols "a" to "e" in FIG. 1, respectively, were treated with "X' pert Highscore Plus", an analytical processing computer software provided with "X' Pert PRO MPD", a product name of a commercially available powder X-ray diffractometer, and subjected to the calculation of average crystallite diameter of anhydrous crystalline ascorbic acid 2-glucoside in each test sample with the program of "Scherrer Formula" in the above computer software.

The above results are in Table 5.

TABLE 5

| Test sample | 17 | 18 | 19 | 20 | 21 | 22 |
|---|---|---|---|---|---|---|
| Production yield (%) of ascorbic acid 2-glucoside | 25.3 | 27.0 | 27.0 | 32.5 | 32.5 | 35.3 |
| Purity (%) of ascorbic acid 2-glucoside | 98.6 | 98.5 | 99.2 | 98.3 | 99.3 | 99.6 |
| Degree of crystallinity (%) | 86.0 | 88.5 | 90.7 | 87.3 | 92.1 | 98.9 |
| Average crystallite diameter (Å) | 1,410 | 1,220 | 1,450 | 1,250 | 1,650 | 1,705 |

As shown in Table 5, Test samples 19 and 21, which had been prepared by purifying and concentrating an enzymatic reaction solution with an ascorbic acid 2-glucoside production yield of 27.0% or 32.5% and crystallizing anhydrous crystalline ascorbic acid 2-glucoside by a pseudo-controlled cooling method, had a degree of crystallinity of over 90% and respective average crystallite diameters of 1,450 Å and 1,650 Å. While, Test sample 17, which had been prepared by purifying and concentrating an enzymatic reaction solution with an ascorbic acid 2-glucoside production yield of 25.3% and precipitating anhydrous crystalline ascorbic acid 2-glucoside from the resulting solution containing L-ascorbic acid 2-glucoside by also a pseudo-controlled cooling method similarly as in the above, had an average crystallite diameter of as relatively high as 1,410 Å but had a degree of crystallinity of less than 90%. Test samples 18 and 20, which had been prepared by purifying and concentrating an enzymatic reaction solution with an ascorbic acid 2-glucoside production yield of 27.0% or 32.5% similarly as in Test samples 19 and 21 and precipitating anhydrous crystalline ascorbic acid 2-glucoside from the solution containing L-ascorbic acid 2-glucoside by a pseudo-controlled cooling method, had a degree of crystallinity of less than 90% and respective average crystallite diameters of as low as 1,220 Å and 1,250 Å. Test sample 22, which had been prepared by purifying and concentrating an enzymatic reaction solution with an ascorbic acid 2-glucoside production yield of 35.3% and precipitating anhydrous crystalline ascorbic acid 2-glucoside from the solution containing L-ascorbic acid 2-glucoside by an unforced cooling method, had a degree of crystallinity of as high as 98.9% and an average crystallite diameter of as high as 1,705 Å.

The results in Table 5 indicate that, even a particulate composition containing anhydrous crystalline ascorbic acid 2-glucoside prepared from a reaction solution with the same production yield of ascorbic acid 2-glucoside, the degree of crystallinity and the average crystallite diameter of anhydrous crystalline ascorbic acid 2-glucoside, which has been crystallized by a pseudo-controlled cooling method, are higher than those of the one obtained by crystallizing by an unforced cooling method. In the case of precipitating anhydrous crystalline 2-glucoside by an unforced cooling method, a particulate composition containing anhydrous crystalline ascorbic acid 2-glucoside with a degree of crystallinity of over 90% could not be obtained unless the production yield of ascorbic acid 2-glucoside is over 35%, while in the case of applying a pseudo-controlled cooling method in crystallization, even an enzymatic reaction solution with an ascorbic acid 2-glucoside production yield of 32.5% (Test sample 21) or 27.0% (Test sample 19) as less than 35%, a particulate composition containing anhydrous crystalline ascorbic acid 2-glucoside with a degree of crystallinity of over 90% has been obtained. These results indicate that a pseudo-controlled cooling method effectively increases the degree of crystallinity and the average crystallite diameter, and a particulate composition containing anhydrous crystalline ascorbic acid 2-glusocide with a degree of crystallinity for anhydrous crystalline ascorbic acid 2-glucoside of over 90% can be obtained by applying either a pseudo-controlled cooling method or controlled cooling method after purification and concentration, as long as the production yield of ascorbic acid 2-glucoside in an enzymatic reaction solution is over 27.0%. Since Test samples 19 and 21 have an ascorbic acid 2-glucoside purity in the range of over 98.0% but below 99.9% and a degree of crystallinity of over 90%, they are particulate compositions containing anhydrous crystalline ascorbic acid 2-glucoside that significantly, more hardly cake compared to a conventional quasi-drug-grade powder.

<Experiment 6: Effect of Average Crystallite Diameter on the Solubility in Hydrophilic Solvent>

As test samples, Test samples 17 to 22 used in the above experiment, particulate compositions containing anhydrous crystalline ascorbic acid 2-glucoside prepared by the methods in the later-described Examples 1 to 4, Test sample 1 prepared in Experiment 1-1, and Test sample 16 (a quasi-drug-grade powder) used in Experiment 3-1 were used for examining their solubilities in hydrophilic solvents widely used in cosmetics and quasi-drugs.

Any one of the above test samples and the particulate compositions of Examples 1 to 4 was weighed 0.25 g and placed in "FALCON TUBE 2059", a product name of a 14-ml polypropylene cylindrical tube having a hemispherical bottom shape and a cap, commercialized by Becton, Dickinson and Company, New Jersey, USA. To each tube with each sample was added five milliliters of a solution, which had been prepared by diluting 1,3-butylene glycol (a special-grade reagent commercialized by Wako Pure Chemical Industries, Ltd., Tokyo, Japan) with deionized water to give a concentration of 30%, and the resulting mixture was heated for 30 min in a constant temperature water bath with 50° C., followed by allowing the tube upset twice, retaining it at 50° C. for 15 min, and macroscopically judging the appearance as follows: "Passable solubility" (−), when a powder was regarded as being completely dissolved; "Impassable solubility" (+), when an insoluble substance(s) was/were observed. When such an insoluble substance(s) was/were observed, it was further kept at 50° C. for 15 min and it was judged as "Slightly impassable solubility" (±), when a powder was deemed completely dissolved. The results are in Table 6.

By using the above test samples or the particulate compositions of Examples 1 to 4, they were subjected to the caking test and the storage stability test by the methods in Experiments 1-4 and 3-2. The results are in Table 6 in parallel. Test samples 1 and 16 were measured for average crystallite diameter by the method in Experiment 5, and the results are in Table 6 in parallel. The results on the ascorbic acid 2-glucoside purity, degree of crystallinity, caking, and storage stability for Test samples 1 and 16 were transcribed from the results in Table 3 for Test samples 1 and 16.

of average crystallite diameter that influences on the solubility in hydrophilic solvents is speculated to be lower than 1,705 Å, and a particulate composition containing anhydrous crystalline ascorbic acid 2-glucoside with an average crystallite diameter of less than 1,700 Å, more particularly, 1,670 Å or lower was judged to be superior to a reagent-grade powder in solubility against hydrophilic solvents. Among Test samples 19 and 21 and the particulate compositions of Examples 1 to 4, which had been evaluated as satisfactory in any items of solubility, caking, and storage stability, the lowest average crystallite diameter is 1,450 Å (Test sample 19) so that a preferable average crystallite diameter was judged to be in the range of 1,400 Å or more but less than 1,700 Å, more preferably, 1,450 Å or more but not higher than 1,670 Å.

<Experiment 7: Production Yield of Ascorbic Acid 2-glucoside by CGTases Derived from Various Microorganisms>

In an enzymatic reaction system where CGTase is allowed to act on a solution containing liquefied starch and L-ascorbic acid and then glucoamylase is allowed to act on the resulting solution to form ascorbic acid 2-glucoside, the following experiment was conducted to examine how does the difference of origin of CGTase influence on the production yield of ascorbic acid 2-glucoside in an enzymatic reaction solution obtained through the above enzymatic reactions.

<Commercialized CGTase>

Among CGTases derived from various microorganisms, the following CGTases are used as commercialized CGTases: "CONTIZYME", a product name of a commercialized CGTase specimen sold by Amano enzyme Inc., Tokyo, Japan, was used as a CGTase derived from a microorganism of the species *Bacillus macerans*; a CGTase derived from *Geobacillus stearothermophilus* TC-91 strain, produced by Hayashibara Biochemical Laboratories, Inc., Okayama, Japan, was used as a CGTase derived from a microorganism of the species *Geobacillus stearothermophi-*

TABLE 6

| Test sample | 1 | 16 | 17 | 18 | 19 | 20 | 21 | 22 | Example 1 | Example 2 | Example 3 | Example 4 |
|---|---|---|---|---|---|---|---|---|---|---|---|---|
| Production yield (%) of ascorbic acid 2-glucoside | | 25.3 | 27.0 | 27.0 | 32.5 | 32.5 | 35.3 | 28.0 | 29.5 | 31.0 | 32.5 | |
| Purity (%) of ascorbic acid 2-glucoside | 99.9 | 98.9 | 98.6 | 98.5 | 99.2 | 98.3 | 99.3 | 99.6 | 99.3 | 99.5 | 99.2 | 99.7 |
| Degree of crystallinity (%) | 100 | 88.9 | 86.0 | 88.5 | 90.7 | 87.3 | 92.1 | 98.9 | 90.3 | 91.0 | 91.5 | 92.4 |
| Average crystallite diameter (Å) | 1,770 | 1,380 | 1,410 | 1,220 | 1,450 | 1,250 | 1,650 | 1,705 | 1,460 | 1,540 | 1,610 | 1,670 |
| Solubility | + | − | − | − | − | − | − | ± | − | − | − | − |
| Caking | − | + | + | + | − | + | − | − | − | − | − | − |
| Storage stability | − | + | + | + | − | + | − | − | − | − | − | − |

As shown in Table 6, Test samples 16 to 21 and the later-described particulate compositions of Examples 1 to 4 with an average crystallite diameter of 1,670 Å or lower were judged as "Passable solubility" (−). On the contrary, Test sample 22 with an average crystallite diameter of 1,705 Å was judged as "Slightly impassable solubility" (±). Test sample 1 (a reagent-grade powder) with an average crystallite diameter of 1,770 Å was judged as "Impassable solubility" (+). The powders of Test samples 1, 19, 21, and 22 and the particulate compositions of Examples 1 to 4 were judged as "Not caked" (−) in the caking test and the storage stability test, while Test samples 16 to 18 and 20 were judged as "Caked" (+). Based on these results, the threshold

*lus*; and "TORUZYME 3.0L", a product name of a commercialized recombinant CGTase sold by Novozymes Japan Ltd., Tokyo, Japan, was used as a CGTase derived from a microorganism of the species *Thermoanaerobacter thermosulfurigenes*.

<Experiment 7-1: Preparation of CGTases Derived from Various Microorganisms>

<Experiment 7-1-1: Preparation of CGTase Derived from *Paenibacillus illinoisensis* NBRC15379 Strain>

*Paenibacillus illinoisensis* NBRC15379 strain was cultured in a liquid culture medium containing 2% dextrin, 0.5% ammonium chloride, 0.05% potassium hydrogen phosphate, 0.025% magnesium sulfate, and 0.5% calcium carbonate at 27° C. for three days. The resulting culture was centrifuged and the resulting supernatant was salted out with ammonium sulfate in usual manner and dialyzed to obtain a crude enzyme solution of CGTase. The crude enzyme solution thus obtained was fed to DEAE-TPYOPEAL 650S commercialized by Tosoh Corp., Tokyo, Japan, a cation-exchange column chromatography, and a hydrophobic column chromatography using BUTYL-TOYOPEARL 650 M gel commercialized by Tosoh Corp., Tokyo, Japan, to obtain a partially purified CGTase.

<Experiment 7-1-2: Preparation of Mutant of CGTase Derived from *Geobacillus stearothermophilus* Tc-91 Strain>

As described above, a gene of a CGTase derived from *Geobacillus stearothermophilus* Tc-91 strain has been cloned and the amino acid sequence of a mature CGTase (amino acid sequence represented by SEQ ID NO:1) has been determined based on the nucleotide sequence (nucleotide sequence represented by SEQ ID NO:2) of the gene. By introducing a mutation into the genetic DNA of the CGTase by the following procedure to obtain a mutant CGTase with a higher productivity of ascorbic acid 2-glucoside than the wild-type CGTase.

Figure 5:
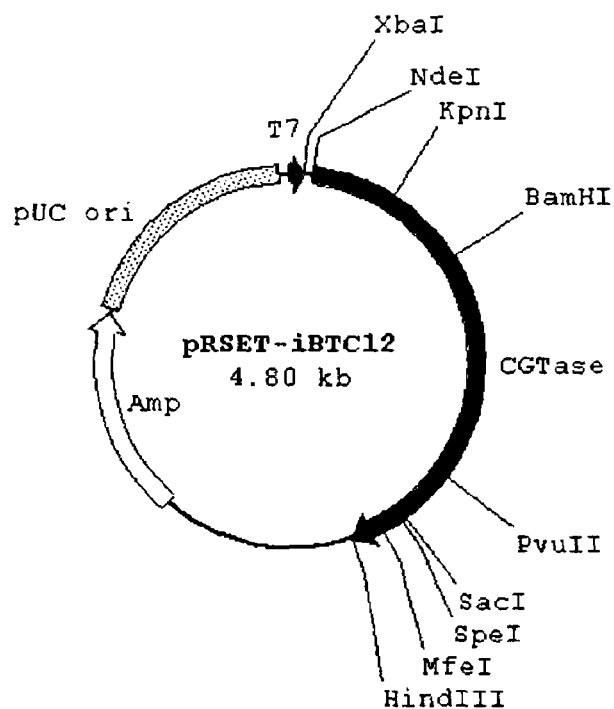
FIG. 5 is a figure of the structure and the restriction enzyme recognition sites of a recombinant DNA "pRSET-iBTC12", which contains a CGTase gene derived from *Geobacillus stearothermophilus* Tc-91 strain used in the present invention.

By using a CGTase gene derived from *Geobacillus stearothermophilus* Tc-91 strain (deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, under the accession number of FERM BP-11273), which had been possessed by the inventors of the present invention, the gene was mutated to introduce or disadvantage a restriction enzyme cleavage site(s) without altering the amino acid sequence encoded by the CGTase gene, and introduced into a plasmid vector to obtain a recombinant DNA containing a gene encoding the wild-type CGTase. FIG. 5 shows the structure of the recombinant DNA "pRSET-iBTC12". Thereafter, a gene fragment (Nde I-EcoT221 fragment) encoding a region containing a wild-type CGTase active residue in the above-obtained recombinant DNA was cleaved and randomly mutated in a test tube by using "GeneMorph PCR Mutagenesis Kit", a product name of a PCR mutation kit commercialized by Stratagene Company, CA, USA, and the resultants were returned to the original DNA to obtain a gene mixture encoding CGTase mutants with various amino acid replacements. By introducing the mutated genes into expression plasmid vectors, recombinant DNAs were obtained. A CGTase mutant gene library was obtained by transforming *E. coli* with the recombinant DNAs.

Over 1,300 strains of transformants were isolated from the obtained gene library and respectively cultured, followed by preparing a cell lysate as a crude enzyme solution containing a CGTase mutant from cells obtained by each culture. The resulting crude enzyme solution was allowed to act on an aqueous solution containing L-ascorbic acid and partial starch hydrolysate, followed by treating the formed α-glycosyl L-ascorbic acids with glucoamylase to form ascorbic acid 2-glucoside, and screening transformants capable of producing CGTase mutants with a relatively-high productivity of ascorbic acid 2-glucoside by comparing the productivity with that of the wild-type CGTase. During the screening process, two transformant strains possessing the aimed mutant CGTase genes, i.e., #129 and #268 strains were obtained. The nucleotide sequences of mutant CGTase genes which are possessed by the transformants were decoded and revealed that a CGTase mutant produced by the transformant #129 strain has an amino acid sequence of SEQ ID NO:1, wherein two amino acid residues have been replaced; the $176^{th}$ glycine residues (G) has been replaced with arginine residue (R) and the $452^{nd}$ tyrosine residue (Y) has been replaced with histidine residue (H), i.e., it has the amino acid sequence of SEQ ID NO:4. While, the CGTase mutant produced from the transformant #268 strain has the amino acid sequence of SEQ ID NO:1, wherein a single amino acid residue has been replaced; the $228^{th}$ lysine residue (K) has been replaced with isoleucine residue (I), i.e., it has the amino acid sequence of SEQ ID NO: 5. These CGTase mutants were respectively named G176R/Y452H and K228I based on the replaced sites of amino acids in the amino acid sequence of SEQ ID NO:1 and the amino acid substitutions.

The above two transformants, which possess genetic DNAs encoding the above CGTase mutants, were respectively aerobically cultured at 37° C. for 24 hours using T culture medium (containing per liter 12 g of bacto-tryptone, 24 g of bacto-yeast extract, 5 ml of glycerol, 17 mM of potassium phosphate, and 72 mM of dipotassium phosphate) containing 100 µl/ml of sodium ampicillin. The cells, obtained by centrifuging each culture, were respectively subjected to disruption treatment with "Ultra Sonic Homogenizer UH-600", a product name of an ultrasonic disruptor commercialized by MST Corporation, Aichi, Japan, and the supernatant of disrupted cells was heated at 60° C. for 30 min to denature and inactivate the non-thermostable proteins derived from the host. The solutions with heat treatment were respectively further centrifuged to obtain partially purified specimens of the CGTase mutants.

The enzyme activity for each of the above CGTases was determined by the above-identified method and calculated by using Formula [4].

<Experiment 7-2: Production Reaction of Ascorbic Acid 2-glucoside>

Five parts by weight of "PINEDEX #1", a product name of a dextrin commercialized by Matsutani Chemical Industries Co., Ltd., Hyogo, Japan, was added to 20 parts by weight of water, dissolved by heating, admixed with three parts by weight of L-ascorbic acid, and adjusted to pH 5.5 for use as a substrate solution. To the substrate solution was added any one of the above-described commercialized CGTases and the CGTases prepared in Experiment 7-1 in an amount of 100 units/g dextrin, d.s.b., and allowed to enzymatically react at 55° C. for 40 hours, followed by heating the enzymatic reaction solutions to inactivate the remaining enzyme to form ascorbic acid 2-glucoside along with α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid. The reaction solutions thus obtained were heated to inactivate the remaining enzyme, adjusted to pH 4.5, admixed with "GLUCZYME AF6", a product name of a glucoamylase specimen (6,000 units/g), commercialized by Amano Enzyme, Inc., Aichi, Japan, in an amount of 50 units/g dextrin, d.s.b., reacted at 55° C. for 24 hours to hydrolyze α-glycosyl-L-ascorbic acids up to ascorbic acid 2-glucoside and to hydrolyze the concomitant saccharides up to D-glucose, and heated to inactivate the remaining glucoamylase to obtain enzymatic reaction solutions 1 to 6.

<Experiment 7-3: Measurement for the Production Yield of Ascorbic Acid 2-glucoside>

The production yields of ascorbic acid 2-glucoside in the enzymatic reaction solutions 1 to 6, obtained in Experiment 7-2, were determined as follows: The enzymatic reaction solutions 1 to 6 were respectively prepared into a 2% solution with refined water, filtered with a 0.45-µm membrane filter and subjected to the HPLC analysis described in Experiment 1-2, followed by calculating the ascorbic acid 2-glucoside content of each of the resulting enzymatic reaction solutions based on the peak area appeared on a chromatogram by a differential refractometer for each solution, and converting the calculated data into those expressed based on a dry solid basis. The results are in Table 7. The production yield of ascorbic acid 2-glucoside in each enzymatic reaction solution in Table 7 is the one that can be reproducibly obtained within a considerable dispersion, even when the production reaction of ascorbic acid 2-glucoside and the glucoamylase treatment are repeated five times under the same conditions for each CGTase.

TABLE 7

| Reaction solution | Type of CGTase | Production yield of ascorbic acid 2-glucoside in enzymatic reaction solution (% by weight)* |
|---|---|---|
| 1 | CGTase from *Bacillus macerans* | 16 |
| 2 | CGTase from *Paenibacillus illinoisensis* NBRC15379 | 18 |
| 3 | CGTase from *Geobacillus stearothermophilus* Tc-91 | 28 |
| 4 | CGTase from *Thermoanaerobacter thermosulfurigenes* | 30 |
| 5 | G176R/Y452H, a mutant of CGTase from *Geobacillus stearothermophilus* Tc-91 | 32 |
| 6 | K228I, a mutant of CGTase derived from *Geobacillus stearothermophilus* Tc-91 strain | 31 |

Note
*After glucoamylase treatment

As shown in Table 7, in the case of using the CGTase derived from a microorganism of the species *Bacillus macerans* (reaction solution 1), the production yield of ascorbic acid 2-glucoside after glucoamylase treatment was up to 16%, and in the case of using the CGTase derived from a microorganism of the species *Paenibacillus illinoisensis* (reaction solution 2), the production yield of ascorbic acid 2-glucoside was as low as 18%. On the contrary, in the case of using the CGTase derived from *Geobacillus stearothermophilus* Tc-91 strain (reaction solution 3), the production yield of ascorbic acid 2-glucoside reached 28%, and in the case of using the CGTase derived from a microorganism of the species *Thermoanaerobacter thermosulfurigenes* (reaction solution 4), the production yield of ascorbic acid 2-glucoside reached 30%. Further, in the case of using G176R/Y452H and K228I, mutants of a CGTase derived from *Geobacillus stearothermophilus* Tc-91 strain, the production yields of ascorbic acid 2-glucoside reached 32% and 31%, respectively.

The results clearly indicate that the CGTases derived from microorganisms of the species *Bacillus macerans* and *Paenibacillus illinoisensis* could not produce ascorbic acid 2-glucoside in an efficient production yield, and they are not suitable for producing ascorbic acid 2-glucoside.

<Experiment 8: Effect of Crystallization Method on the Purities and the Properties of Ascorbic Acid 2-glucoside in Particulate Composition Containing Anhydrous Crystalline Ascorbic Acid 2-glucoside>

By using a conventional unforced-cooling method and pseudo-controlled cooling method as crystallization methods for precipitating anhydrous crystalline ascorbic acid 2-glucoside, particulate compositions containing anhydrous crystalline ascorbic acid 2-glucoside were prepared from the enzymatic reaction solutions 3 to 6 with different production yields of ascorbic acid 2-glucoside obtained in Experiment 7, followed by examining the effects of such crystallization methods on the purities and the properties of powdered ascorbic acid 2-glucoside. The enzymatic reaction solutions 1 and 2 with a distinctly-low production yield of ascorbic acid 2-glucoside at their stages of enzymatic reaction solutions, i.e., the enzymatic reaction solutions, which had been prepared by allowing a CGTase derived from a microorganism of the species *Bacillus macerans* or *Paenibacillus illinoisensis* to act on each of their substrates, were not used to prepare powders because they were judged to be unable to efficiently produce any particulate composition containing anhydrous crystalline ascorbic acid 2-glucoside.

<Experiment 8-1: Preparation of Test Samples>
<Test Samples 23 to 26>

The enzymatic reaction solutions 3 to 6 with different ascorbic acid 2-glucoside production yields obtained in Experiment 7 were respectively decolored with an activated charcoal, filtered, desalted with a cation-exchange resin ($H^+$-form), and subjected to an anion-exchange resin ($OH^-$-form) to adsorb thereupon L-ascorbic acid and ascorbic acid 2-glucoside, followed by washing the resin with water to remove saccharides containing D-glucose and feeding 0.5 N aqueous hydrochloric acid solution to effect elution. Each of the eluates was concentrated to give a solid concentration of about 50%, d.s.b., and subjected to a column chromatography using a column packed with "DIAION UBK 550" ($Na^+$-form), a product name of a strong-acid cation exchange resin commercialized by Mitsubishi Chemical Corp., Tokyo, Japan, in order to obtain high ascorbic acid 2-glucoside content fractions with an ascorbic acid 2-glucoside content of 86% or more. The collected fractions were pooled and concentrated to give a solid content of about 75%, d.s.b., to obtain ascorbic acid 2-glucoside containing solutions 3 to 6 (containing 86.3 to 87.1%, d.s.b., of ascorbic acid 2-glucoside), which corresponded to the enzymatic reaction solutions 3 to 6, respectively.

Each of the above ascorbic-acid-2-gluoside-containing solutions 3 to 6 was placed in a crystallizer, admixed with anhydrous crystalline ascorbic acid 2-glucoside as a seed crystal in a content of about two percent (w/v) of the volume of each saccharide solution, and crystallized by unforcedly cooling each solution from 40° C. to 15° C. over about 48 hours under stirring conditions to obtain a massecuite with precipitated anhydrous crystalline ascorbic acid 2-glucoside. An anhydrous crystalline ascorbic acid 2-glucoside was collected from the massecuite by a conventional basket-type centrifuge, washed with deionized water in a content of eight percent of the weight of each massecuite, aged and dried at 40° C. for three hours, forcedly cooled by blowing thereunto 25° C. clean air for 30 min, and pulverized into particulate compositions containing anhydrous crystalline ascorbic acid 2-glucoside. These particulate compositions containing anhydrous crystalline ascorbic acid 2-glucoside, obtained from the ascorbic acid 2-glucoside containing solutions 3 to 6 by an unforced-cooling method, were respectively named Test samples 23 to 26.

<Test Samples 23c to 26c>

Similarly as in the above, a massecuite with precipitated anhydrous crystalline ascorbic acid 2-glucoside was obtained except that each of the ascorbic-acid-2-glucoside-containing solutions 3 to 6 with different ascorbic acid 2-glucoside contents, d.s.b., prepared in the above, was concentrated in vacuo to give a solid concentration of about 75%, d.s.b., placed in a crystallizer, admixed with anhydrous crystalline ascorbic acid 2-glucoside as a seed crystal in a content of about two percent (w/v) of the volume of the concentrate, and subjected to crystallization by a pseudo-controlled cooling method of cooling from 40° C. to 15° C. over about 48 hours under stirring conditions. In the pseudo-controlled cooling method, the crystallization time of 48 hours in total was divided into three zones of 24 hours, 12 hours, and 12 hours, wherein in the first zone, the liquid temperature was cooled from 40° C. to 35° C. over 24 hours; in the middle zone, the liquid temperature was cooled from 35° C. to 27.5° C. over 12 hours; and in the last zone, the liquid temperature was cooled from 27.5° C. to 15° C. over 12 hours. From the obtained each massecuite, anhydrous crystalline ascorbic acid 2-glucoside was collected by a conventional basket-type centrifuge, washed with deionized water in a content of eight percent of the massecuite weight, aged and dried at 40° C. for three hours, forcedly cooled by blowing thereunto 25° C. clean air for 30 min, and pulverized into particulate compositions containing anhydrous crystalline ascorbic acid 2-glucoside. These particulate compositions, containing anhydrous crystalline ascorbic acid 2-glucoside obtained from the ascorbic acid 2-glucoside containing solutions 3 to 6 by the pseudo-controlled cooling method, were respectively named Test samples 23c to 26c.

<Experiment 8-2: Purities and Properties of Ascorbic Acid 2-glucoside of Test Samples 23 to 26 and Test Samples 23c to 26c>

For Test samples 23 to 26 and Test samples 23c to 26c obtained in the above, they were examined, similarly as in Experiment 6, for their purities, degrees of crystallinity, average crystallite diameters, cakings, and solubilities in 1,3-butylene glycol as a hydrophilic solvent. The results are in Table 8. The result for Test sample 16 as a quasi-drug-grade powder was transcribed from Table 6 and shown in Table 8 in parallel.

TABLE 8

| Test sample | Purity of ascorbic acid 2-glucoside (% by weight) | Degree of crystallinity (%) | Average crystallite diameter (Å) | Caking | Solubility |
|---|---|---|---|---|---|
| 23 | 98.5 | 87.2 | 1,220 | + | − |
| 24 | 98.4 | 87.8 | 1,240 | + | − |
| 25 | 98.5 | 88.5 | 1,280 | + | − |
| 26 | 98.5 | 87.6 | 1,280 | + | − |
| 23c | 99.5 | 90.6 | 1,480 | − | − |
| 24c | 99.5 | 92.2 | 1,520 | − | − |
| 25c | 99.6 | 93.4 | 1,540 | − | − |

TABLE 8-continued

| Test sample | Purity of ascorbic acid 2-glucoside (% by weight) | Degree of crystallinity (%) | Average crystallite diameter (Å) | Caking | Solubility |
|---|---|---|---|---|---|
| 26c | 99.5 | 92.8 | 1,500 | − | − |
| 16 | 98.9 | 88.9 | 1,380 | + | − |

As shown in Table 8, the ascorbic acid 2-glucoside content, d.s.b., or the purity of ascorbic acid 2-glucoside in the particulate compositions containing anhydrous crystalline ascorbic acid 2-glucoside of Test samples 23 to 26 and Test samples 23c to 26c were all over 98%, and these Test samples were particulate compositions containing a relatively-high purity anhydrous crystalline ascorbic acid 2-glucoside similar to Test sample 16 that is a particulate composition containing anhydrous crystalline ascorbic acid 2-glucoside as a conventional quasi-drug-grade powder.

As for the degrees of crystallinity, Test samples 23 to 26, which had been prepared by applying a conventional unforced cooling method in the crystallization step for anhydrous crystalline ascorbic acid 2-glucoside, remained in the degrees of crystallinity of less than 90% similar to that of Test sample 16 as a conventional quasi-drug-grade powder; while all Test samples 23c to 26c, which had been prepared by applying a pseudo-controlled cooling method in the crystallization step, showed a degree of crystallinity of 90% or more, reconfirming that such a pseudo-controlled cooling method has an effect of increasing the degree of crystallinity of a resulting particulate composition containing anhydrous crystalline ascorbic acid 2-glucoside. Similarly as the degrees of crystallinity of powders, the average crystallite diameters of Test samples 23 to 26 remained in the range of 1,220 to 1,280 Å, while Test samples 23c to 26c had average crystallite diameters of as high as 1,480 to 1,540 Å.

Also regarding the caking of powders, Test samples 23 to 26, which had degrees of crystallinity of less than 90% and average crystallite diameters of less than 1,400 Å, were judged as "Caked" (+), while Test samples 23c to 26c, which had degrees of crystallinity of at least 90% and average crystallite diameters of 1,400 Å or more, were judged as "Not caked" (−). For the solubility in 1,3-butylene glycol, every test sample was judged as "Passable solubility" (−).

The results in Experiments 7 and 8 indicate that a particulate composition, which has a degree of crystallinity of at least 90% and significantly, more hardly cakes, is produced by preparing an enzymatic reaction solution with an ascorbic acid 2-glucoside production yield of 27% or more by using, in a process for producing anhydrous crystalline ascorbic acid 2-glucoside, any of a CGTase derived from a microorganism of the species *Geobacillus stearothermophilus*, mutant enzymes thereof, and a CGTase derived from a microorganism of the species *Thermoanaerobacter thermosulfurigenes*; purifying the enzymatic reaction solution to give an ascorbic acid 2-glucoside content of 86% or more; and applying a pseudo-controlled cooling method or controlled cooling method in the crystallization step.

<Experiment 9: Effect of the Combination Use of Starch-Debranching Enzyme on the Production Yields of Ascorbic Acid 2-glucoside by CGTases Derived from Various Microorganisms>

The following experiment was conducted to examine how the combination use of a starch-debranching enzyme effects on the production yield of ascorbic acid 2-glucoside in an enzymatic reaction solution, obtained through an enzymatic reaction using any of CGTases derived from various microorganisms in an enzymatic reaction system, where any of such CGTases is allowed to act on a solution containing liquefied starch and L-ascorbic acid and then glucoamylase is allowed to act on the resulting solution to form ascorbic acid 2-glucoside.

<Experiment 9-1: Production Reaction of Ascorbic Acid 2-glucoside>

A production reaction of ascorbic acid 2-glucoside was conducted similarly as in Experiment 7, except for allowing 1,000 units/g dextrin, d.s.b., of an enzyme preparation of isoamylase (derived from a microorganism of the species *Pseudomonas amyloderamosa*, commercialized by Hayashibara Co., Ltd., Okayama, Japan) as a starch-debranching enzyme along with any of the CGTases used in Experiment 7. The resulting ascorbic acid 2-glucoside was treated with glucoamylase to obtain any of the enzymatic reaction solutions 7 to 12 as shown in the later-described Table 9, followed by measuring the production yield of ascorbic acid 2-glucoside in each of the enzymatic reaction solutions 7 to 12 by the method in Experiment 1-2. The results are in Table 9.

(reaction solution 8), even when a starch-debranching enzyme was used in combination, the production yields of ascorbic acid 2-glucoside after glucoamylase treatment remained in 21% and 25%, respectively, which were significantly lower than those obtained with a single use of any of the CGTases other than the above-identified CGTases (see reaction solutions 3 to 6 in Table 7).

The above results indicate that, when a starch-debranching enzyme is used in combination, the CGTase derived from *Geobacillus stearothermophilus* Tc-91 strain, the CGTase derived from a microorganism of the species *Thermoanaerobacter thermosulfurigenes*, and G176R/Y452H and K228I as mutants of the CGTase derived from *Geobacillus stearothermophilus* Tc-91 strain more efficiently produce ascorbic acid 2-glucoside because they attain a higher production yield of ascorbic acid 2-glucoside by about 3% to about 9% than that attained with a single use of any of the CGTases without using a starch-debranching enzyme.

The above results reconfirmed that the CGTases derived from microorganisms of the species *Bacillus macerans* and *Paenibacillus illinoisensis* are not suitable for producing ascorbic acid 2-glucoside because they could not efficiently

TABLE 9

| Reaction solution | Type of CGTase | Production yield of ascorbic acid 2-glucoside in enzymatic reaction solution (% by weight)* |
|---|---|---|
| 7 | CGTase from *Bacillus macerans* | 21 |
| 8 | CGTase from *Paenibacillus illinoisensis* NBRC15379 | 25 |
| 9 | CGTase from *Geobacillus stearothermophilus* Tc-91 | 37 |
| 10 | CGTase from *Thermoanaerobacter thermosulfurigenes* | 33 |
| 11 | G176R/Y452H, a mutant of CGTase derived from *Geobacillus stearothermophilus* Tc-91 strain | 37 |
| 12 | K228I, a mutant of CGTase from *Geobacillus stearothermophilus* Tc-91 | 36 |

Note
*After glucoamylase treatment

As found in Table 9, when used in combination with a starch-debranching enzyme, the CGTase derived from a microorganism of the species *Bacillus macerans* (reaction solution 7) and the CGTase derived from a microorganism of the species *Paenibacillus illinoisensis* (reaction solution 8) exhibited ascorbic acid 2-glucoside production yields of 21% and 25%, respectively, after glucoamylase treatment. While, the CGTase derived from *Geobacillus stearothermophilus* Tc-91 strain (reaction solution 9) exhibited an ascorbic acid 2-glucoside production yield of 37%, and the CGTase derived from a microorganism of the species *Thermoanaerobacter thermosulfurigenes* (reaction solution 10) exhibited an ascorbic acid 2-glucoside production yield of 33%. In the case of using G176R/Y452H and K228I, mutants of a CGTase derived from *Geobacillus stearothermophilus* Tc-91 strain, exhibited 37% and 36%, respectively.

Varying depending on CGTases' origins, the combination use of a starch-debranching enzyme (isoamylase) with the enzymatic reaction by CGTase more significantly increased the production yield of ascorbic acid 2-glucoside after glucoamylase treatment in any of the enzymatic reaction solutions 7 to 12 by 3% to 9%, compared to those obtained with a single use of the respective CGTases (see the reaction solutions 1 to 6 in Table 7). In the case of the CGTase derived from a microorganism of the species *Bacillus macerans* (reaction solution 7) and the CGTase derived from a microorganism of the species *Paenibacillus illinoisensis* produce ascorbic acid 2-glucoside even when used in combination with a starch-debranching enzyme.

<Experiment 10: Effect of Crystallization Method on the Production of Particulate Composition Containing Anhydrous Crystalline Ascorbic Acid 2-glucoside from Reaction Solution Obtained by Using CGTase and Starch-Debranching Enzyme in Combination>

In this experiment, the effect of crystallization method on the purity and the properties of a powdered ascorbic acid 2-glucoside was examined similarly as in Experiment 8, when in producing a particulate composition containing anhydrous crystalline ascorbic acid 2-glucoside from an enzymatic reaction solution obtained by using a CGTase and a starch-debranching enzyme in combination. For the enzymatic reaction solutions 7 and 8 with a relatively-low production yield of ascorbic acid 2-glucoside, any powders thereof were not prepared for the same reason as in Experiment 8.

<Experiment 10-1: Preparation of Test Samples>
<Test Samples 27 to 30>

The enzymatic reaction solutions 9 to 12, obtained in Experiment 9, were respectively purified similarly as in Experiment 8 into ascorbic acid 2-glucoside containing solutions 9 to 12 with an ascorbic acid 2-glucoside content of 86% or more, followed by precipitating anhydrous crystalline ascorbic acid 2-glucoside by applying thereunto an unforced-cooling method similarly as in Experiment 8-1 to prepare particulate compositions containing anhydrous crystalline ascorbic acid 2-glucoside for use as Test samples 27 to 30.

<Test Samples 27c to 30c>

Similarly as in Test samples 27 to 30, except for applying the same pseudo-controlled cooling method as in Experiment 8 in the crystallization step for ascorbic acid 2-glucoside, particulate compositions containing anhydrous crystalline ascorbic acid 2-glucoside were prepared from the ascorbic-acid-2-glucoside-containing solutions 9 to 12 with an ascorbic acid content of 86% or more for use as Test samples 27c and 30c.

<Experiment 10-2: Purities and Properties of Ascorbic Acid 2-glucoside of Test Samples 27 to 30 and Test Samples 27c to 30c>

Similarly as in Experiment 8, Test samples 27 to 30 and Test samples 27c to 30c were respectively examined for their purities of ascorbic acid 2-glucoside, degrees of crystallinity, average crystallite diameters, cakings, and solubilities in 1,3-butylene glycol as a hydrophilic solvent. The results are in Table 10. The result of Test sample 16 as a quasi-drug-grade powder was transcribed from Table 6 and shown in Table 10 in parallel.

TABLE 10

| Test sample | Purity of ascorbic acid 2-glucoside (% by weight) | Degree of crystallinity (%) | Average crystallite diameter (Å) | Caking | Solubility |
|---|---|---|---|---|---|
| 27 | 99.4 | 92.6 | 1,440 | − | − |
| 28 | 99.2 | 88.0 | 1,280 | + | − |
| 29 | 99.5 | 94.2 | 1,480 | − | − |
| 30 | 99.6 | 93.8 | 1,460 | − | − |
| 27c | 99.7 | 97.6 | 1,660 | − | − |
| 28c | 99.6 | 97.2 | 1,620 | − | − |
| 29c | 99.8 | 98.0 | 1,680 | − | − |
| 30c | 99.6 | 97.1 | 1,650 | − | − |
| 16 | 98.9 | 88.9 | 1,380 | + | − |

As evident from Table 10, any of Test samples 27 to 30 excluding Test sample 28 and Test samples 27c to 30c had an ascorbic acid 2-glucoside purity of at least 99.2%, a degree of crystallinity of at least 92.6%, and an average crystallite diameter of 1,440 Å or more, and they were powders that exhibited no caking under the conditions tested. Test sample 28, which had been prepared from an enzymatic reaction solution with an ascorbic acid 2-glucoside production yield of up to 33% at the stage of an enzymatic reaction prepared by applying an unforced cooling method in crystallization step, had an ascorbic acid 2-glucoside purity of 99.2%, a degree of crystallinity of 88.0%, and an average crystallite diameter of 1,280 Å, and it was judged as "Caked" (+) in the caking test. On the contrary, as evident from the results of Test sample 28c, even when the production yield of ascorbic acid 2-glucoside stays at most 33% at the stage of an enzymatic reaction, a powder that does not exhibit caking can be obtained by applying a pseudo-controlled cooling method in the crystallization step to make it to have a degree of crystallinity of at least 90% and an average crystallite diameter of 1,400 Å or more.

The above results indicate that a particulate composition containing anhydrous crystalline ascorbic acid 2-glucoside, which substantially, more hardly cakes and has a degree of crystallinity of at least 90%, can be produced from an enzymatic reaction solution with an increased production yield of ascorbic acid 2-glucoside to 35% or higher by combinationally using a starch-debranching enzyme in a reaction for producing ascorbic acid 2-glucoside, independently of a cooling method used in crystallization step; and a particulate composition containing anhydrous crystalline ascorbic acid 2-glucoside, which substantially, more hardly cakes and has a degree of crystallinity of at least 90%, can be produced even from an enzymatic reaction solution with an increased production yield of ascorbic acid 2-glucoside to about 33% as below as 35% by applying a pseudo-controlled cooling method or controlled cooling method in crystallization step.

<Experiment 11: Common Partial Amino Acid Sequences of CGTases Suitable for Producing Ascorbic Acid 2-glucoside>

To characterize CGTases suitable for producing ascorbic acid 2-glucoside, amino acid sequences (SEQ ID NOs: 1, 4 and 5) of a CGTase derived from *Geobacillus stearothermophilus* Tc-91 strain and its mutant enzymes, and an amino acid sequence (SEQ ID NO: 3) of a CGTase derived from a microorganism of the species *Thermoanaerobacter thermosulfurigenes*, which are suitable for producing ascorbic acid 2-glucoside, were compared with an amino acid sequence (SEQ ID NO:6) of a CGTase derived from a microorganism of the species *Bacillus macerans* and the one (SEQ ID NO:7) of a CGTase derived from a microorganism of the species *Paenibacillus illinoisensis*, which are not suitable for producing ascorbic acid 2-glucoside. In comparing these amino acid sequences, there used were those of the CGTases derived from *Geobacillus stearothermophilus* Tc-91 strain and a microorganism of the species *Bacillus macerans*, which had been determined uniquely by the same applicant as the present invention, disclosed respectively in Japanese Patent Kokai No. 135581/86 applied for by the same applicant as the present invention. An amino acid sequence registered in "GenBank", a gene data base, under the accession number of 35484 was used as the one for a CGTase derived from a microorganism of the species *Thermoanaerobacter thermosulfurigenes*. Further, it was used as the amino acid sequence of a CGTase derived from a microorganism of the species *Paenibacillus illinoisensis*, the one encoded by the nucleotide sequence, determined uniquely by the same applicant as the present invention after cloning the CGTase gene of *Paenibacillus illinoisensis* NBRC15379 strain.

In comparison of the above amino acid sequences, the following partial amino acid sequences of (a) to (d) were determined as those which commonly exist in CGTases suitable for producing ascorbic acid 2-glucoside, i.e., a CGTase derived from *Geobacillus stearothermophilus* Tc-91 strain, mutant enzymes thereof, and a CGTase derived from a microorganism of the species *Thermoanaerobacter thermosulfurigenes*, but do not exist in CGTases not suitable for producing ascorbic acid 2-glucoside, i.e., CGTases derived from microorganisms of the species *Bacillus macerans* and *Paenibacillus illinoisensis*:

(a) Asn-Glu-Val-Asp-$X_1$-Asn-Asn;
(b) Met-Ile-Gln-$X_2$-Thr-Ala;
(c) Pro-Gly-Lys-Tyr-Asn-Ile; and
(d) Val-$X_3$-Ser-Asn-Gly-Ser-Val.
(Wherein $X_1$ means Pro or Ala, $X_2$ means Ser or Asp, and $X_3$ means Ser or Gly)

Based on the above results, it was revealed that the CGTase suitable for producing ascorbic acid 2-glucoside by the process according to the present invention, i.e., CGTases, which attain an ascorbic acid 2-glucoside production yield of 27% or more, are characterized by the above-identified partial amino acid sequences of (a) to (d).

The following Examples, Comparative Examples, and Examples for Reference explain the present invention in more detail, but the present invention should never be restricted thereby.

EXAMPLE 1

<Production of Particulate Composition Containing Anhydrous Crystalline Ascorbic Acid 2-glucoside>

Four parts by weight of liquefied potato starch was added to 20 parts by weight of water, dissolved therein by heating, and admixed with three parts by weight of L-ascorbic acid, followed by adjusting the resulting solution to pH 5.5 for use as a substrate solution. To the substrate solution was added a crude enzyme solution (produced by Hayashibara Biochemical Laboratories, Inc., Okayama, Japan) of a CGTase derived from *Geobacillus stearothermophilus* Tc-91 strain (deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, under the accession number of FERM BP-11273) in an amount of 100 units/g solid of the liquefied potato starch, d.s.b., and enzymatically reacted at 55° C. for 40 hours to form ascorbic acid 2-glucoside and α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid.

After heating the enzymatic reaction solution to inactivate the remaining enzyme, the resulting solution was adjusted to pH 4.5, admixed with "GLUCZYME AF6", a product name of a glucoamylase specimen (6,000 units/g), commercialized by Amano Enzyme, Inc., Aichi, Japan, in an amount of 50 units/g solid, d.s.b., of the liquefied potato starch and treated at 55° C. for 24 hours to hydrolyze α-glycosyl-L-ascorbic acids up to ascorbic acid 2-glucoside and to hydrolyze the concomitant saccharides up to D-glucose. The production yield of L-ascorbic acid 2-glucoside was about 28%.

After inactivating the remaining enzyme by heating, the enzymatic reaction solution was decolored with an activated charcoal and filtered, and the filtrate was desalted with a cation-exchange resin (H+-form). Then, L-ascorbic acid and ascorbic acid 2-glucoside in the desalted solution were allowed to adsorb on an anion-exchange resin (OH−-form), followed by washing the resin with water to remove D-glucose before elution with 0.5 N aqueous hydrochloric acid solution. The concentrate was concentrated to give a solid concentration of about 50% and subjected to a simulated-moving-bed column chromatography using 10 columns packed with "DIAION UBK 550" (Na+-form), a product name of a strong-acid cation exchange resin commercialized by Mitsubishi Chemical Corp., Tokyo, Japan. The resulting eluate was charged to the columns in a level of about 1/40-fold volume of the wet resin volume, followed by feeding to the columns an eluent in a level of about 5-fold volumes of the charged volume and sequentially collecting fractions rich in ascorbic acid 2-glucoside but poor in L-ascorbic acid. The fractions were pooled, revealing that it contained 87.2%, d.s.b., of ascorbic acid 2-glucoside.

After the pooled fractions were concentrated under a reduced pressure into an about 76% concentrate, which was then placed in a crystallizer and admixed with "ASCORBIC ACID 2-GLUCOSIDE 999" (Code No.: AG124, an ascorbic acid 2-glucoside purity of at least 99.9%), a product name of a particulate composition containing anhydrous crystalline ascorbic acid 2-glucoside, commercialized as an analytical standard reagent by Hayashibara Biochemical Laboratories, Inc., Okayama, Japan, as a seed crystal, in a content of two percent of the solid contents. Then, the mixture solution was adjusted to 40° C. and subjected to a pseudo-controlled cooling method of cooling the solution from 40° C. to 30° C. over 1.5 days and then cooling it from 30° C. to 15° C. over 0.5 day under gentle stirring conditions to precipitate anhydrous crystalline ascorbic acid 2-glucoside.

The precipitated crystals were collected by a basket-type centrifuge, washed by spraying thereunto a small content of cold refined water, aged and dried at 38° C. for three hours, cooled by blowing thereunto 25° C. air for 45 min, and pulverized to obtain a particulate composition containing anhydrous crystalline ascorbic acid 2-glucoside, which had an ascorbic acid 2-glucoside purity of 99.3%, a total L-ascorbic acid and D-glucose content of 0.1%, an L-ascorbic acid content of less than 0.1%, a reducing power of the whole particulate composition of 0.27%, a degree of crystallinity for anhydrous crystalline ascorbic acid 2-glucoside of 90.3%, and an average crystallite diameter of 1,460 Å. Incidentally, the above degree of crystallinity was determined by the Hermans' method using the analytical values $H_{100}$ and $H_0$ obtained in Experiment 1-2. When measured for particle size distribution, the particulate composition contained particles with a particle size of less than 150 μm in a content of 91.0% and those with a particle size of 53 μm or more but less than 150 μm in a content of 50.7%.

The particulate composition is readily handleable because it substantially, more hardly cakes and has a superior solubility in hydrophilic solvents widely used in cosmetics and quasi-drugs, compared to a conventional quasi-drug-grade powder commercialized as a skin-whitening ingredient for quasi-drugs. Since the particulate composition does not differ from such a conventional quasi-drug-grade powder in that it is a particulate composition containing anhydrous crystalline ascorbic acid 2-glucoside similarly as the above conventional quasi-drug-grade powder, it can be used alone or in combination with other ingredients as a powdered material for food products, food additives, cosmetics, quasi-drugs, pharmaceuticals, etc.

EXAMPLE 2

<Production of Particulate Composition Containing Anhydrous Crystalline Ascorbic Acid 2-glucoside>

A particulate composition containing anhydrous crystalline ascorbic acid 2-glucoside was prepared similarly as in Example 1, except for allowing a pullulanase (Product code of "EN201", commercialized by Hayashibara Biochemical Laboratories, Inc., Okayama, Japan) derived from a microorganism of the species *Klebsiella pneumoniae* (*Aerobacter aerogenes*) to act on a solution containing liquefied starch and L-ascorbic acid in an amount of five units per solid of the liquefied starch, when allowing CGTase to act on the solution containing liquefied starch and L-ascorbic acid; and employing a pseudo-controlled cooling method of cooling the solution from 40° C. to 35° C. over 1.5 days and then cooling it from 35° C. to 15° C. over 0.5 day, when precipitating anhydrous crystalline ascorbic acid 2-glucoside. Furthermore, the production yield of ascorbic acid 2-glucoside in the enzymatic reaction solution after glucoamylase treatment was about 29.5%. The ascorbic acid 2-glucoside content, d.s.b, in the solution, which had been subjected to crystallization of ascorbic acid 2-glucoside, was 91.80.

The product had an ascorbic acid 2-glucoside purity of 99.5%, a total L-ascorbic acid and D-glucose content of 0.1%, an L-ascorbic acid content of less than 0.1%, a reducing power of the whole particulate composition of 0.21%, a degree of crystallinity for anhydrous crystalline ascorbic acid 2-glucoside of 91.0%, and an average crystallite diameter of 1,540 Å. Incidentally, the above degree of crystallinity was determined by the Hermans' method using the analytical values $H_{100}$ and $H_0$ obtained in Experiment 1-2. When measured for particle size distribution, the particulate composition contained particles with a particle size of less than 150 μm in a content of 93.0% and those with a particle size of 53 μm or more but less than 150 μm in a content of 53.7%.

The particulate composition is readily handleable because it substantially, more hardly cakes and has a superior solubility in hydrophilic solvents widely used in cosmetics and quasi-drugs, compared to a conventional quasi-drug-grade powder commercialized as a skin-whitening ingredient for quasi-drugs. Since the particulate composition does not differ from such a conventional quasi-drug-grade powder in that it is a particulate composition containing anhydrous crystalline ascorbic acid 2-glucoside similarly as the above conventional quasi-drug-grade powder, it can be used alone or in combination with other ingredients as a powdered material for food products, food additives, cosmetics, quasi-drugs, pharmaceuticals, etc.

EXAMPLE 3

<Production of Particulate Composition Containing Anhydrous Crystalline Ascorbic Acid 2-glucoside>

Five parts by weight of corn starch was added to 15 parts by weight of water and then dissolved therein by heating after the addition of a commercialized liquefying enzyme. The resulting solution was admixed with three parts by weight of L-ascorbic acid and adjusted to pH 5.5 for use as a substrate solution. To the substrate solution was added "TORUZYME 3.0L" (see, for example, Patent Literatures 30 and 31), a product name of a commercially available CGTase specimen, commercialized by Novozymes Japan Ltd., Tokyo, Japan, which had been prepared by recombining a CGTase gene derived from a microorganism of the genus *Thermoanaerobacter* and allowing the resulting recombinant CGTase to express in a microorganism of the genus *Bacillus*, in an amount of 100 units/g solid of the corn starch, d.s.b., and enzymatically reacted at 55° C. for 50 hours to form ascorbic acid 2-glucoside and other α-glycosyl-L-ascorbic acids.

After inactivating the remaining enzymes by heating, the enzymatic reaction solution was adjusted to pH 4.5, admixed with "GLUCOZYME #20000", a product name of a glucoamylase specimen with an activity of 20,000 units/g, commercialized by Nagase ChemteX Corp., Osaka, Japan, in an amount of 50 units/g solid of the corn starch, d.s.b., and enzymatically reacted at 55° C. for 24 hours to hydrolyze α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid up to ascorbic acid 2-glucoside and to hydrolyze the concomitant saccharides up to D-glucose. The production yield of ascorbic acid 2-glucoside in the resulting reaction solution was about 31%.

After inactivating the remaining enzyme by heating, the reaction solution was decolored with an activated charcoal and filtered. The filtrate was desalted with a cation-exchange resin ($H^+$-form) and fed to an anion-exchange resin ($OH^-$-form) to adsorb thereupon L-ascorbic acid and ascorbic acid 2-glucoside, followed by washing the anion-exchange resin with water to remove D-glucose and feeding 0.5 N hydrochloric acid solution to the resin for elution. The eluate was subjected to a column chromatography using "TOYOPEARL HW-40", a product name of a porous resin of Tosoh Corp., Tokyo, Japan, to collect fractions rich in ascorbic acid 2-glucoside but poor in L-ascorbic acid. The collected fractions were pooled, revealing that it contained 88.6%, d.s.b., of ascorbic acid 2-glucoside.

The pooled fractions were concentrated under a reduced pressure into an about 76% concentrate, which was then placed in a crystallizer and admixed with the particulate composition containing anhydrous crystalline ascorbic acid 2-glucoside prepared in Example 1, as a seed crystal, in a content of two percent of the solid contents. Thereafter, the concentrate was heated to 40° C. and subjected to a pseudo-controlled cooling method of cooling the concentrate under gentle stirring conditions from 40° C. to 33° C. over 1.5 days and then from 33° C. to 15° C. over 0.5 day to precipitate anhydrous crystalline ascorbic acid 2-glucoside.

The crystals were collected by using a basket-type centrifuge, washed by spraying thereunto a small amount of distilled water, ageing and drying the resultant at 35° C. for eight hours, cooling the resultant product by blowing thereunto 25° C. air for 15 min, and pulverizing the cooled product to obtain a particulate composition containing anhydrous crystalline ascorbic acid 2-glucoside, which had an ascorbic acid 2-glucoside purity of 99.2%, a total L-ascorbic acid and D-glucose content of less than 0.1%, an L-ascorbic acid content of less than 0.1%, a reducing power of the whole particulate composition of 0.17%, a degree of crystallinity for anhydrous crystalline ascorbic acid 2-glucoside of 91.5%, and an average crystallite diameter of 1,610 Å. Incidentally, the above degree of crystallinity was determined by the Hermans' method using the analytical values $H_{100}$ and $H_0$ obtained in Experiment 1-2. When measured for particle size distribution, the particulate composition contained particles with a particle size of less than 150 μm in a content of 83.2% and those with a particle size of 53 μm or more but less than 150 μm in a content of 57.1%.

The particulate composition is readily handleable because it substantially, more hardly cakes and has a superior solubility in hydrophilic solvents widely used in cosmetics and quasi-drugs, compared to a conventional quasi-drug-grade powder commercialized as a skin-whitening ingredient for quasi-drugs. Since the particulate composition does not differ from such a conventional quasi-drug-grade powder in that it is a particulate composition containing anhydrous crystalline ascorbic acid 2-glucoside similarly as the above conventional quasi-drug-grade powder, it can be used alone or in combination with other ingredients as a powdered material for food products, food additives, cosmetics, quasi-drugs, pharmaceuticals, etc.

EXAMPLE 4

<Production of Particulate Composition Containing Anhydrous Crystalline Ascorbic Acid 2-glucoside>

A particulate composition containing anhydrous crystalline ascorbic acid 2-glucoside was prepared by using the same method as in Example 1, except for adding six parts by weight of corn starch to 15 parts by weight of water, dissolving the corn starch by heating after the addition of a commercialized liquefying enzyme, adding three parts by weight of L-ascorbic acid to the resulting solution, allowing "TORUZYME 3.0L", a product name of a commercially available CGTase, commercialized by Novozymes Japan Ltd., Tokyo, Japan, to act on the solution, at which an isoamylase specimen derived from a microorganism of the species *Pseudomonas amyloderamosa* (ATCC 21262), commercialized by Hayashibara Biochemical Laboratories, Inc., Okayama, Japan, was allowed to act on the solution in an amount of 500 units/g solid of the corn starch, d.s.b., and employing a pseudo-controlled cooling method of cooling the solution from 40° C. to 35° C. over 24 hours and then cooling it from 35° C. to 15° C. over 12 hours, when precipitating anhydrous crystalline ascorbic acid 2-glucoside. The production yield of ascorbic acid 2-glucoside in the reaction solution after glucoamylase treatment was about 32.5%. The ascorbic acid 2-glucoside content, d.s.b., in the solution, which had been subjected to precipitation of anhydrous crystalline ascorbic acid 2-glucoside, was 89.6%.

The product had an ascorbic acid 2-glucoside purity of 99.7%, a total L-ascorbic acid and D-glucose content of less than 0.1%, an L-ascorbic acid content of less than 0.1%, a reducing power of the whole particulate composition of 0.10%, a degree of crystallinity for anhydrous crystalline ascorbic acid 2-glucoside of 92.4%, and an average crystallite diameter of 1,670 Å. Incidentally, the above degree of crystallinity was determined by the Hermans' method using the analytical values $H_{100}$ and $H_0$ obtained in Experiment 1-2. When measured for particle size distribution, the particulate composition contained particles with a particle size of less than 150 µm in a content of 94.5% and those with a particle size of 53 µm or more but less than 150 µm in a content of 55.3%.

The particulate composition is readily handleable because it substantially, more hardly cakes and has a superior solubility in hydrophilic solvents widely used in cosmetics and quasi-drugs, compared to a conventional quasi-drug-grade powder commercialized as a skin-whitening ingredient for quasi-drugs. Since the particulate composition does not differ from such a conventional quasi-drug-grade powder in that it is a particulate composition containing anhydrous crystalline ascorbic acid 2-glucoside similarly as the above conventional quasi-drug-grade powder, it can be used alone or in combination with other ingredients as a powdered material for food products, food additives, cosmetics, quasi-drugs, pharmaceuticals, etc.

EXAMPLE 5

<Production of Particulate Composition Containing Anhydrous Crystalline Ascorbic Acid 2-glucoside>

Five parts by weight of corn starch was added to 15 parts by weight of water and then dissolved therein by heating after the addition of a commercialized liquefying enzyme. The resulting solution was admixed with three parts by weight of L-ascorbic acid and adjusted to pH 5.5 for use as a substrate solution. To the substrate solution was added G176R/Y452H as a mutant of a CGTase derived from *Geobacillus stearothermophilus* Tc-91 strain used in Experiments 7 and 9 in an amount of 100 units/g solid of the corn starch, d.s.b., and enzymatically reacted at 55° C. for 50 hours to form ascorbic acid 2-glucoside and other α-glycosyl-L-ascorbic acids.

After inactivating the remaining enzymes by heating, the reaction solution was adjusted to pH 4.5, admixed with "GLUCOZYME #20000", a product name of a glucoamylase specimen (20,000 units/g), commercialized by Nagase ChemteX Corp., Osaka, Japan, in an amount of 50 units/g solid of the corn starch, d.s.b., and enzymatically reacted at 55° C. for 24 hours to hydrolyze α-glycosyl-L-ascorbic acids such as 2-O-α-maltosyl-L-ascorbic acid, 2-O-α-maltotriosyl-L-ascorbic acid, and 2-O-α-maltotetraosyl-L-ascorbic acid up to ascorbic acid 2-glucoside and to hydrolyze the concomitant saccharides up to D-glucose. The production yield of ascorbic acid 2-glucoside in the resulting reaction solution was about 31.5%.

After inactivating the remaining enzyme by heating, the reaction solution was decolored with an activated charcoal and filtered. The filtrate was desalted with a cation-exchange resin ($H^+$-form) and fed to an anion-exchange resin ($OH^-$-form) to adsorb L-ascorbic acid and ascorbic acid 2-glucoside thereupon, followed by washing the anion-exchange resin with water to remove D-glucose and feeding 0.5 N hydrochloric acid solution to the resin for elution. The eluate was fed to a column chromatography using "TOYOPEARL HW-40", a product name of a porous resin of Tosoh Corp., Tokyo, Japan, to collect fractions rich in ascorbic acid 2-glucoside but poor in L-ascorbic acid. The collected fractions were pooled, revealing that it contained 87.6%, d.s.b., of ascorbic acid 2-glucoside.

The pooled fractions were then placed in a crystallizer and admixed with "ASCORBIC ACID 2-GLUCOSIDE 999" (Code No.: AG124, an ascorbic acid 2-glucoside purity of at least 99.9%), a product name of a standard-reagent-grade particulate composition containing anhydrous crystalline ascorbic acid 2-glucoside, commercialized by Hayashibara Biochemical Laboratories, Inc., Okayama, Japan, as a seed crystal, in a content of two percent of the solid contents. Then, the mixture solution was adjusted to 40° C. and subjected to a pseudo-controlled cooling method of successively cooling the solution from 40° C. to 35° C. over 24 hours, from 35° C. to 30° C. over 12 hours, and from 30° C. to 15° C. over 12 hours under gentle stirring conditions to precipitate anhydrous crystalline ascorbic acid 2-glucoside. The crystals were collected by using a basket-type centrifuge, washed by spraying thereunto a refined water in a content of about five percent of the weight of a massecuite, ageing and drying the resultant at 35° C. for eight hours, cooling the dried product by blowing thereunto 20° C. air for 10 min, and pulverizing the cooled product to obtain a particulate composition containing anhydrous crystalline ascorbic acid 2-glucoside, which had an ascorbic acid 2-glucoside purity of 99.2%, a total L-ascorbic acid and D-glucose content of 0.4%, an L-ascorbic acid content of less than 0.1%, and a reducing power of the whole particulate composition of 0.50%.

The particulate composition containing anhydrous crystalline ascorbic acid 2-glucoside product thus obtained had a degree of crystallinity for anhydrous crystalline ascorbic acid 2-glucoside of 90.4%, and an average crystallite diameter of 1,480 Å. The above degree of crystallinity was determined by the Hermans' method using the analytical values $H_{100}$ and $H_0$ obtained in Experiment 1-2. When the particulate composition was measured for particle size distribution, it contained particles with a particle size of less than 150 µm in a content of 85.2% and those with a particle size of 53 µm or more but less than 150 µm in a content of 69.3%. When the composition was subjected to the same caking test as in Experiment 1-4, it was judged as "Not caked" (−). Also, the product was judged as "Passable solubility", when subjected to the same test for solubility in 1,3-butylene glycol as in Experiment 6.

The particulate composition containing anhydrous crystalline ascorbic acid 2-glucoside produced by the above-identified process is powder that significantly, more hardly cakes and is easily storable and handleable even though the particulate composition has no major difference compared to "AA2G", a product name of a particulate composition containing anhydrous crystalline ascorbic acid 2-glucoside, as a commercialized conventional quasi-drug-grade powder, sold by Hayashibara Shoji, Co., Ltd., Okayama, Japan.

Since the particulate composition is similar to such a conventional quasi-drug-grade powder in that it is a particulate composition containing anhydrous crystalline ascorbic acid 2-glucoside and since it is easily stored and handled, it can be more suitably used as a material for food products, food additives, cosmetics, quasi-drugs, pharmaceuticals, etc.

EXAMPLE 6

<Production of Particulate Composition Containing Anhydrous Crystalline Ascorbic Acid 2-glucoside>

Four parts by weight of liquefied potato starch was added to 20 parts by weight of water and then dissolved therein by heating. The resulting solution was admixed with three parts by weight of L-ascorbic acid and adjusted to pH 5.5 for use as a substrate solution. To the substrate solution was added a CGTase derived from *Geobacillus stearothermophilus* Tc-91 strain in an amount of 100 units/g solid of the starch, d.s.b., and "GODO-FIA", a product name of an isoamylase specimen derived from a microorganism of the species *Flavobacterium odoratus* produced by Godo Shusei Co., Ltd., Tokyo, Japan, in an amount of 500 units/g solid of the starch, d.s.b., and enzymatically reacted at 55° C. for 40 hours to form ascorbic acid 2-glucoside and α-glycosyl-L-ascorbic acids such as 2-O-α-maltosyl-L-ascorbic acid, 2-O-α-maltotriosyl-L-ascorbic acid, and maltotetraosyl-L-ascorbic acid.

After heated to inactivate the remaining enzymes, the enzymatic reaction solution was adjusted to pH 4.5, admixed with "GLUCZYME AF6", a product name of a glucoamylase specimen (6,000 units/g), commercialized by Amano Enzyme Inc., Aichi, Japan, in an amount of 50 units/g solid of the starch, d.s.b., and treated by heating at 55° C. for 24 hours to hydrolyze α-glycosyl-L-ascorbic acids into ascorbic acid 2-glucoside and the concomitant saccharides up to D-glucose. The production yield of L-ascorbic acid 2-glucoside in the reaction solution was about 36%.

The reaction solution was heated to inactivate the remaining enzyme, decolored with an activated charcoal, filtered, desalted with a cation-exchange resin ($H^+$-form), and subjected to an anion-exchange resin ($OH^-$-form) to adsorb thereupon L-ascorbic acid and ascorbic acid 2-glucoside, followed by washing the anion-exchange resin with water to remove saccharides containing D-glucose and feeding 0.5 N aqueous hydrochloric acid solution to effect elution. The eluate was concentrated up to give a solid concentration of about 50%, d.s.b., and subjected to a simulated-moving-bed column chromatography using 10 columns packed with "DIAION UBK 550" ($Na^+$-form), a product name of a strong-acid cation exchange resin commercialized by Mitsubishi Chemical Corp., Tokyo, Japan. The eluate, which had been concentrated to give a solid concentration of about 50%, was charged to the columns in a level of about 1/40-fold volume of the wet resin volume, and fed with an eluent in a level of about 15-fold volumes of the charged volume to elute ascorbic acid 2-glucoside, followed by collecting fractions rich in ascorbic acid 2-glucoside but poor in L-ascorbic acid. The fractions were pooled, revealing that it contained about 86.6%, d.s.b., of ascorbic acid 2-glucoside.

The pooled fractions were concentrated in vacuo into an about 76% concentrate, which was then placed in a crystallizer and admixed with "ASCORBIC ACID 2-GLUCOSIDE 999" (Code No.: AG124, an ascorbic acid 2-glucoside purity of at least 99.9%), a product name of a reagent-grade particulate composition containing anhydrous crystalline ascorbic acid 2-glucoside, commercialized by Hayashibara Biochemical Laboratories, Inc., Okayama, Japan, as a seed crystal, in a level of two percent of the solid contents. Then, the mixture solution was adjusted to 40° C. and cooled over 48 hours by successively cooling the solution from 40° C. to 35° C. over 20 hours, from 35° C. to 30° C. over 16 hours, and from 30° C. to 15° C. over 12 hours under gentle stirring conditions by a pseudo-controlled cooling method to crystallize anhydrous crystalline ascorbic acid 2-glucoside. The crystals were collected by using a basket-type centrifuge, washed by spraying thereunto a refined water in a content of about five percent of the weight of the massecuite, ageing and drying the resultant at 38° C. for three hours, cooling the resultant product by blowing thereunto 20° C. air for 45 min, and pulverizing the cooled product to obtain a particulate composition containing anhydrous crystalline ascorbic acid 2-glucoside, which had an ascorbic acid 2-glucoside purity of 99.5%, d.s.b., a total L-ascorbic acid and D-glucose content of 0.1%, an L-ascorbic acid content of less than 0.1%, and a reducing power of the whole particulate composition of 0.21%.

The particulate composition containing anhydrous crystalline ascorbic acid 2-glucoside obtained by the above-identified process had a degree of crystallinity for anhydrous crystalline ascorbic acid 2-glucoside of 93.9%, and an average crystallite diameter of 1,630 Å. Incidentally, the above degree of crystallinity was determined by the Hermans' method using the analytical values $H_{100}$ and $H_0$ obtained in Experiment 1-2. When the particulate composition was measured for particle size distribution, it contained particles with a particle size of less than 150 μm in a content of 91.2% and those with a particle size of 53 μm or more but less than 150 μm in a content of 57.3%. When the composition was subjected to the same caking test as in Experiment 1-4, it was judged as "Not caked" (−). Also, when the product was subjected to the same test for solubility in 1,3-butylene glycol as in Experiment 6, it was judged as "Passable solubility".

The particulate composition containing anhydrous crystalline ascorbic acid 2-glucoside is a powder that significantly, more hardly cakes compared to a conventional quasi-drug-grade powder, and it can be advantageously used as a material for food products, food additives, cosmetics, quasi-drugs, pharmaceuticals, etc.

EXAMPLE 7

<Production of Particulate Composition Containing Anhydrous Crystalline Ascorbic Acid 2-glucoside>

A particulate composition containing anhydrous crystalline ascorbic acid 2-glucoside was produced similarly as in Example 6, except for using, in the production reaction for ascorbic acid 2-glucoside, "TORUZYME 3.0L", a product name of a recombinant CGTase, commercialized by Novozymes Japan Ltd., Tokyo, Japan, prepared from a CGTase derived from a microorganism of the genus *Thermoanaerobacter*, and "PROMOZYME", a product name of a pullulanase specimen derived from a microorganism of the species *Bacillus acidopullulyticus*, commercialized by Novozymes Japan Ltd., Tokyo, Japan, as a starch-debranching enzyme to be used in combination with the CGTase, in an amount of 50 units/g solid of the starch, d.s.b.; and, in the crystallization step, applying a pseudo-controlled cooling method of cooling the enzymatic reaction solution from 40° C. to 15° C. over 48 hours by five steps, i.e., sequentially cooling the solution from 40° C. to 38° C. over 12 hours, from 38° C. to 35° C. over 12 hours, from 35° C. to 30° C. over eight hours, from 30° C. to 23° C. over eight hours, and then from 23° C. to 15° C. over eight hours. The particulate composition had, on a dry solid basis, an ascorbic acid 2-glucoside content of 99.3%, a total L-ascorbic acid and D-glucose content of 0.1%, an L-ascorbic acid content of less than 0.1%, and a reducing power of the whole particulate composition of 0.28%. This process afforded an ascorbic acid 2-glucoside production yield of 32.9% in the reaction solution after glucoamylase treatment. The ascorbic acid 2-glucoside content, d.s.b., in the solution, which had been subjected to crystallization of anhydrous crystalline ascorbic acid 2-glucoside, was 86.4%.

The particulate composition containing anhydrous crystalline ascorbic acid 2-glucoside had a degree of crystallinity for anhydrous crystalline ascorbic acid 2-glucoside of 96.4%, and had an average crystallite diameter of 1,570 Å. Incidentally, the above degree of crystallinity was determined by the Hermans' method using the analytical values $H_{100}$ and $H_0$ obtained in Experiment 1-2. When the particulate composition was measured for particle size distribution, it contained particles with a particle size of less than 150 μm in a content of 92.2% and those with a particle size of 53 μm or more but less than 150 μm in a content of 54.8%. When the composition was subjected to the same caking test as in Experiment 1-4, it was judged as "Not caked" (−). Also, the product was judged as "Passable solubility", when subjected to the same test for solubility in 1,3-butylene glycol as in Experiment 6.

The particulate composition containing anhydrous crystalline ascorbic acid 2-glucoside produced by the above-identified process is a powder that significantly, more hardly cakes and is easily storable and handleable even though the particulate composition has no major difference compared to "AA2G", a product name of a particulate composition containing anhydrous crystalline ascorbic acid 2-glucoside, as a commercialized conventional quasi-drug-grade powder, sold by Hayashibara Shoji, Co., Ltd., Okayama, Japan.

Since the particulate composition is similar to such a conventional quasi-drug-grade powder in that it is a particulate composition containing anhydrous crystalline ascorbic acid 2-glucoside and since it is easily stored and handled, it can be more suitably used as a material for food products, food additives, cosmetics, quasi-drugs, pharmaceuticals, etc.

EXAMPLE 8

<Production of Particulate Composition Containing Anhydrous Crystalline Ascorbic Acid 2-glucoside>

A particulate composition containing anhydrous crystalline ascorbic acid 2-glucoside was produced similarly as in Example 3, except for using a general-purpose programmed constant circulator for crystallization system in the crystallization step for anhydrous crystalline ascorbic acid 2-glucoside, and applying a controlled cooling method of cooling the reaction solution from 40° C. to 15° C. over 48 hours by a 20-step cooling profile near-identical to Formula [7] in such a manner of feeding a temperature-controlled heat carrier to the jacket of a crystallizer. The particulate composition thus obtained had, on a dry solid basis, an ascorbic acid 2-glucoside content of 99.6%, a total L-ascorbic acid and D-glucose content of 0.1%, an L-ascorbic acid content of less than 0.1%, and a reducing power of the whole particulate composition of 0.17%. This production afforded an ascorbic acid 2-glucoside production yield of about 31% in the reaction solution after glucoamylase treatment. The ascorbic acid 2-glucoside content, d.s.b., in the solution, which had been subjected to crystallization of anhydrous crystalline ascorbic acid 2-glucoside, was 88.7%.

The particulate composition containing anhydrous crystalline ascorbic acid 2-glucoside had a degree of crystallinity for anhydrous crystalline ascorbic acid 2-glucoside of 93.0%, and had an average crystallite diameter of 1,650 Å. Incidentally, the above degree of crystallinity was determined by the Hermans' method using the analytical values $H_{100}$ and $H_0$ obtained in Experiment 1-2. When the particulate composition was measured for particle size distribution, it contained particles with a particle size of less than 150 μm in a content of 90.4% and those with a particle size of 53 μm or more but less than 150 μm in a content of 65.3%. When the composition was subjected to the same caking test as in Experiment 1-4, it was judged as "Not caked" (−). Also, the product was judged as "Passable solubility", when subjected to the same test for solubility in 1,3-butylene glycol as in Experiment 6.

The particulate composition containing anhydrous crystalline ascorbic acid 2-glucoside produced by the above-identified process is a powder that significantly, more hardly cakes and is easily storable and handleable even though the particulate composition has no major difference compared to "AA2G", a product name of a particulate composition containing anhydrous crystalline ascorbic acid 2-glucoside, as a commercialized conventional quasi-drug-grade powder, sold by Hayashibara Shoji, Co., Ltd., Okayama, Japan.

Since the particulate composition is similar to such a conventional quasi-drug-grade powder in that it is a particulate composition containing anhydrous crystalline ascorbic acid 2-glucoside and since it is easily stored and handled, it can be more suitably used as a material for food products, food additives, cosmetics, quasi-drugs, pharmaceuticals, etc.

COMPARATIVE EXAMPLE 1

<Production of Particulate Composition Containing Anhydrous Crystalline Ascorbic Acid 2-glucoside>

A particulate composition containing anhydrous crystalline ascorbic acid 2-glucoside was prepared similarly as in Example 1, except for using a conventional unforced cooling method without applying a pseudo-controlled cooling method in the crystallization step for anhydrous crystalline ascorbic acid 2-glucoside. The particulate composition thus obtained had, on a dry solid basis, an ascorbic acid 2-glucoside content of 98.6%, a total L-ascorbic acid and D-glucose content of 0.5%, an L-ascorbic acid content of less than 0.3%, and a reducing power of the whole particulate composition of 0.72%. This production afforded an ascorbic acid 2-glucoside production yield of about 28.4% in the reaction solution after glucoamylase treatment, and the ascorbic acid 2-glucoside content, d.s.b., in the solution, which had been subjected to precipitation of anhydrous crystalline ascorbic acid 2-glucoside, was 86.5%.

The particulate composition containing anhydrous crystalline ascorbic acid 2-glucoside had a degree of crystallinity for anhydrous crystalline ascorbic acid 2-glucoside of 87.5%, and had an average crystallite diameter of 1,290 Å. Incidentally, the above degree of crystallinity was determined by the Hermans' method using the analytical values $H_{100}$ and $H_0$ obtained in Experiment 1-2. When the particulate composition measured for particle size distribution, it contained particles with a particle size of less than 150 μm in a content of 74.8% and those with a particle size of 53 μm or more but less than 150 μm in a content of 68.6%. When the composition was subjected to the same caking test as in Experiment 1-4, it was judged as "Caked" (+). Also, when the product was subjected to the same test for solubility in 1,3-butylene glycol as in Experiment 6, it was judged as "Passable solubility".

COMPARATIVE EXAMPLE 2

<Production of Particulate Composition Containing Anhydrous Crystalline Ascorbic Acid 2-glucoside>

A particulate composition containing anhydrous crystalline ascorbic acid 2-glucoside was prepared similarly as in Example 3, except for using a conventional unforced cooling method without applying a pseudo-controlled cooling method in the crystallization step for anhydrous crystalline ascorbic acid 2-glucoside. The particulate composition thus obtained had, on a dry solid basis, an ascorbic acid 2-glucoside content of 98.3%, a total L-ascorbic acid and D-glucose content of 0.6%, an L-ascorbic acid content of less than 0.4%, and a reducing power of the whole particulate composition of 0.85%. This production afforded an ascorbic acid 2-glucoside production yield of about 30.5% in the reaction solution after glucoamylase treatment, and the ascorbic acid 2-glucoside content, d.s.b., in the solution, which had been subjected to crystallization of anhydrous crystalline ascorbic acid 2-glucoside, was 87.8%.

The particulate composition containing anhydrous crystalline ascorbic acid 2-glucoside had a degree of crystallinity for anhydrous crystalline ascorbic acid 2-glucoside of 88.6%, and had an average crystallite diameter of 1,310 Å. Incidentally, the above degree of crystallinity was determined by the Hermans' method using the analytical values $H_{100}$ and $H_0$ obtained in Experiment 1-2. When the particulate composition measured for particle size distribution, it contained particles with a particle size of less than 150 μm in a content of 76.5% and those with a particle size of 53 μm or more but less than 150 μm in a content of 68.4%. When the composition was subjected to the same caking test as in Experiment 1-4, it was judged as "Caked" (+). Also, when the product was subjected to the same test for solubility in 1,3-butylene glycol as in Experiment 6, it was judged as "Passable solubility".

EXAMPLE FOR REFERENCE 1

<Production of Particulate Composition Containing Anhydrous Crystalline Ascorbic Acid 2-glucoside>

Five parts by weight of potato starch was added to 15 parts by weight of water and then dissolved therein by heating after the addition of a commercialized liquefying enzyme. The resulting solution was admixed with three parts by weight of L-ascorbic acid and adjusted to pH 5.5 for use as a substrate solution. To the substrate solution was added a CGTase derived from *Geobacillus stearothermophilus* Tc-91 strain (deposited with International Patent Organism Depositary in National Institute of Advanced Industrial Science and Technology, Tsukuba Central 6, 1-1, Higashi 1-chome, Tsukuba-shi, Ibaraki-ken, 305-8566 Japan, under the accession number of FERM BP-11273) and an isoamylase, produced by Hayashibara Biochemical Laboratories, Inc., Okayama, Japan, in respective amounts of 100 units and 1,000 units/g solid of the potato starch, d.s.b., and reacted at 55° C. for 50 hours to form ascorbic acid 2-glucoside and other α-glycosyl-L-ascorbic acids. After inactivating the remaining enzymes by heating, the reaction solution was adjusted to pH 4.5, admixed with "GLUCOZYME #20000", a product name of a glucoamylase specimen with an activity of 20,000 units/g, commercialized by Nagase ChemteX Corp., Osaka, Japan, in an amount of 50 units/g solid of the potato starch, d.s.b., and enzymatically reacted at 55° C. for 24 hours to hydrolyze α-glycosyl-L-ascorbic acids up to ascorbic acid 2-glucoside and to hydrolyze the concomitant saccharides up to D-glucose. The production yield of ascorbic 2-glucoside in the resulting reaction solution was about 38%.

After heated to inactivate the remaining enzyme, the reaction solution was decolored with an activated charcoal and filtered. The filtrate was desalted with a cation-exchange resin ($H^+$-form) and fed to an anion-exchange resin ($OH^-$-form) to adsorb L-ascorbic acid and ascorbic acid 2-glucoside thereupon, followed by washing the anion-exchange resin with water to remove D-glucose and feeding 0.5 N hydrochloric acid solution to the resin to effect elution. The eluate was fed to a column chromatography using "TOYOPEARL HW-40", a product name of a porous resin of Tosoh Corp., Tokyo, Japan, to collect fractions rich in ascorbic acid 2-glucoside but poor in L-ascorbic acid. The collected fractions were pooled, revealing that it contained 87.6%, d.s.b., of ascorbic acid 2-glucoside.

The pooled fractions were concentrated in vacuo into an about 76% concentrate, which was then placed in a crystallizer and admixed with the particulate composition containing anhydrous crystalline ascorbic acid 2-glucoside prepared in Example 1, as a seed crystal, in a level of two percent of the solid contents. Thereafter, the resulting mixture was heated to 40° C. and subjected to an unforced cooling method of cooling the mixture to 15° C. over two days under gentle stirring conditions to precipitate anhydrous crystalline ascorbic acid 2-glucoside. The crystals were collected by using a basket-type centrifuge, washed by spraying thereunto a small amount of distilled water, ageing and drying the resultant at 35° C. for eight hours, cooling the resultant product by blowing thereunto 20° C. air for 10 min, and pulverizing the cooled product to obtain a particulate composition containing anhydrous crystalline ascorbic acid 2-glucoside, which had an ascorbic acid 2-glucoside purity of 98.5%, a total L-ascorbic acid and D-glucose content of less than 0.1%, an L-ascorbic acid content of less than 0.1%, a reducing power of the whole particulate composition of 0.15%, a degree of crystallinity for anhydrous crystalline ascorbic acid 2-glucoside of 91.8%, and an average crystallite diameter of 1,320 Å. Incidentally, the above degree of crystallinity was determined by the Hermans' method using the analytical values $H_{100}$ and $H_0$ obtained in Experiment 1-2. When the particulate composition was measured for particle size distribution, it contained particles with a particle size of less than 150 μm in a content of 83.0% and those with a particle size of 53 μm or more but less than 150 μm in a content of 57.7%. When the composition was subjected to the same caking test, storage stability test, and solubility test as in respective Experiments 1-4, 3-2, and 6, it was judged as "Not caked" (−) in the caking test and the storage stability test, but judged as "Impassable solubility" (−) in the solubility test.

INDUSTRIAL APPLICABILITY

As described above, according to the process for producing a particulate composition containing anhydrous crystalline ascorbic acid 2-glucoside, a particulate composition containing anhydrous crystalline ascorbic acid 2-glucoside, which significantly, more hardly cakes compared to conventional quasi-drug-grade powders, can be produced by using either starch or dextrin and L-ascorbic acid as materials and applying a controlled cooling method or pseudo-controlled cooling method in the crystallization step even when the production yield of ascorbic acid 2-glucoside in an enzymatic reaction solution does not reach 35%. As described above, the process according to the present invention expands the range of choices for enzymes used and enables to more effectively produce particulate compositions containing anhydrous crystalline ascorbic acid 2-glucoside on an industrial scale by using, as materials, either starch or dextrin and L-ascorbic acid that are finite resources; and thus, it has a particular industrial utility.

Explanation of Symbols

In FIG. 1, the symbols "a" to "e" mean as follows:
a: A diffraction peak at a diffraction angle (2θ) of 10.4° (Miller index (hkl):120) for use in calculating crystallite diameter;
b: A diffraction peak at a diffraction angle (2θ) of 13.2° (Miller index (hkl):130) for use in calculating crystallite diameter;
c: A diffraction peak at a diffraction angle (2θ) of 18.3° (Miller index (hkl):230) for use in calculating crystallite diameter;
d: A diffraction peak at a diffraction angle (2θ) of 21.9° (Miller index (hkl):060) for use in calculating crystallite diameter; and
e: A diffraction peak at a diffraction angle (2θ) of 22.6° (Miller index (hkl):131) for use in calculating crystallite diameter.

In FIG. 5, the following symbols mean as follows:
pUC on: A replication origin of plasmid pUC;
T7: T7 Promotor;
White arrow (Amp): An ampicillin-resistant gene; and
Black arrow: A CGTase gene.

In FIG. 6, the symbols "a" to "c" mean as follows:
a: Controlled cooling curve;
b: Linear cooling; and
c: Unforced cooling curve.

---

What is claimed is:

1. A particulate composition comprising anhydrous crystalline 2-O-α-D-glucosyl-L-ascorbic acid, which comprises 2-O-α-D-glucosyl-L-ascorbic acid in an amount of over 98.0% by weight but 99.8% by weight or lower, on a dry solid basis;

which has a degree of crystallinity of 90% or higher for anhydrous crystalline 2-O-α-D-glucosyl-L-ascorbic acid, when calculated based on a profile of powder X-ray diffraction analysis of said composition;

which contains particles with a particle size of less than 150 μm in an amount of 70% by weight or higher to the whole particulate composition, and those with a particle size of at least 53 μm but less than 150 μm in an amount of 40 to 60% by weight to the whole composition; and which has a reducing power of the whole composition being less than one percent by weight.

* * * * *

SEQUENCE LISTING

```
<160> NUMBER OF SEQ ID NOS: 7

<210> SEQ ID NO 1
<211> LENGTH: 680
<212> TYPE: PRT
<213> ORGANISM: Geobacillus stearothermophilus

<400> SEQUENCE: 1

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30

Gly Ala Leu Phe Ser Ser Gly Cys Thr Asn Leu Arg Lys Tyr Cys Gly
        35                  40                  45

Gly Asp Trp Gln Gly Ile Ile Asn Lys Ile Asn Asp Gly Tyr Leu Thr
    50                  55                  60

Asp Met Gly Val Thr Ala Ile Trp Ile Ser Gln Pro Val Glu Asn Val
65                  70                  75                  80

Phe Ser Val Met Asn Asp Ala Ser Gly Ser Ala Ser Tyr His Gly Tyr
                85                  90                  95

Trp Ala Arg Asp Phe Lys Lys Pro Asn Pro Phe Phe Gly Thr Leu Ser
            100                 105                 110

Asp Phe Gln Arg Leu Val Asp Ala Ala His Ala Lys Gly Ile Lys Val
        115                 120                 125

Ile Ile Asp Phe Ala Pro Asn His Thr Ser Pro Ala Ser Glu Thr Asn
    130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
    210                 215                 220

Asp Ala Val Lys His Met Pro Phe Gly Trp Gln Lys Ser Leu Met Asp
225                 230                 235                 240
```

```
Glu Ile Asp Asn Tyr Arg Pro Val Phe Thr Phe Gly Glu Trp Phe Leu
            245                 250                 255
Ser Glu Asn Glu Val Asp Ala Asn Asn His Tyr Phe Ala Asn Glu Ser
        260                 265                 270
Gly Met Ser Leu Leu Asp Phe Arg Phe Gly Gln Lys Leu Arg Gln Val
    275                 280                 285
Leu Arg Asn Asn Ser Asp Asn Trp Tyr Gly Phe Asn Gln Met Ile Gln
290                 295                 300
Asp Thr Ala Ser Ala Tyr Asp Glu Val Leu Asp Gln Val Thr Phe Ile
305                 310                 315                 320
Asp Asn His Asp Met Asp Arg Phe Met Ile Asp Gly Gly Asp Pro Arg
                325                 330                 335
Lys Val Asp Met Ala Leu Ala Val Leu Leu Thr Ser Arg Gly Val Pro
            340                 345                 350
Asn Ile Tyr Tyr Gly Thr Glu Gln Tyr Met Thr Gly Asn Gly Asp Pro
        355                 360                 365
Asn Asn Arg Lys Met Met Ser Ser Phe Asn Lys Asn Thr Arg Ala Tyr
    370                 375                 380
Gln Val Ile Gln Lys Leu Ser Ser Leu Arg Arg Asn Asn Pro Ala Leu
385                 390                 395                 400
Ala Tyr Gly Asp Thr Glu Gln Arg Trp Ile Asn Gly Asp Val Tyr Val
                405                 410                 415
Tyr Glu Arg Gln Phe Gly Lys Asp Val Val Leu Val Ala Val Asn Arg
            420                 425                 430
Ser Ser Ser Asn Tyr Ser Ile Thr Gly Leu Phe Thr Ala Leu Pro
        435                 440                 445
Ala Gly Thr Tyr Thr Asp Gln Leu Gly Gly Leu Leu Asp Gly Asn Thr
    450                 455                 460
Ile Gln Val Gly Ser Asn Gly Ser Val Asn Ala Phe Asp Leu Gly Pro
465                 470                 475                 480
Gly Glu Val Gly Val Trp Ala Tyr Ser Ala Thr Glu Ser Thr Pro Ile
                485                 490                 495
Ile Gly His Val Gly Pro Met Met Gly Gln Val Gly His Gln Val Thr
            500                 505                 510
Ile Asp Gly Glu Gly Phe Gly Thr Asn Thr Gly Thr Val Lys Phe Gly
        515                 520                 525
Thr Thr Ala Ala Asn Val Val Ser Trp Ser Asn Asn Gln Ile Val Val
    530                 535                 540
Ala Val Pro Asn Val Ser Pro Gly Lys Tyr Asn Ile Thr Val Gln Ser
545                 550                 555                 560
Ser Ser Gly Gln Thr Ser Ala Ala Tyr Asp Asn Phe Glu Val Leu Thr
                565                 570                 575
Asn Asp Gln Val Ser Val Arg Phe Val Val Asn Asn Ala Thr Thr Asn
            580                 585                 590
Leu Gly Gln Asn Ile Tyr Ile Val Gly Asn Val Tyr Glu Leu Gly Asn
        595                 600                 605
Trp Asp Thr Ser Lys Ala Ile Gly Pro Met Phe Asn Gln Val Val Tyr
    610                 615                 620
Ser Tyr Pro Thr Trp Tyr Ile Asp Val Ser Val Pro Glu Gly Lys Thr
625                 630                 635                 640
Ile Glu Phe Lys Phe Ile Lys Lys Asp Ser Gln Gly Asn Val Thr Trp
                645                 650                 655
Glu Ser Gly Ser Asn His Val Tyr Thr Thr Pro Thr Asn Thr Thr Gly
```

```
              660                 665                 670
Lys Ile Ile Val Asp Trp Gln Asn
        675             680

<210> SEQ ID NO 2
<211> LENGTH: 2133
<212> TYPE: DNA
<213> ORGANISM: Geobacillus stearothermophilus
<220> FEATURE:
<221> NAME/KEY: CDS
<222> LOCATION: (1)..(2133)

<400> SEQUENCE: 2 atg aga aga tgg ctt tcg cta gtc ttg agc atg tca ttt gta ttt agt     48
Met Arg Arg Trp Leu Ser Leu Val Leu Ser Met Ser Phe Val Phe Ser
1               5                  10                  15 gca att ttt ata gta tct gat acg cag aaa gtc acc gtt gaa gca gct     96
Ala Ile Phe Ile Val Ser Asp Thr Gln Lys Val Thr Val Glu Ala Ala
                20                  25                  30 gga aat ctt aat aag gta aac ttt aca tca gat gtt gtc tat caa att    144
Gly Asn Leu Asn Lys Val Asn Phe Thr Ser Asp Val Val Tyr Gln Ile
            35                  40                  45 gta gtg gat cga ttt gtg gat gga aat aca tcc aat aat ccg agt gga    192
Val Val Asp Arg Phe Val Asp Gly Asn Thr Ser Asn Asn Pro Ser Gly
        50                  55                  60 gca tta ttt agc tca gga tgt acg aat tta cgc aag tat tgc ggt gga    240
Ala Leu Phe Ser Ser Gly Cys Thr Asn Leu Arg Lys Tyr Cys Gly Gly
65                  70                  75                  80 gat tgg caa ggc atc atc aat aaa att aac gat ggg tat tta aca gat    288
Asp Trp Gln Gly Ile Ile Asn Lys Ile Asn Asp Gly Tyr Leu Thr Asp
                85                  90                  95 atg ggt gtg aca gcg ata tgg att tct cag cct gta gaa aat gta ttt    336
Met Gly Val Thr Ala Ile Trp Ile Ser Gln Pro Val Glu Asn Val Phe
                100                 105                 110 tct gtg atg aat gat gca agc ggt tca gcc tcc tat cat ggt tat tgg    384
Ser Val Met Asn Asp Ala Ser Gly Ser Ala Ser Tyr His Gly Tyr Trp
            115                 120                 125 gcg cgc gat ttc aaa aag cca aac ccg ttt ttt ggt acc ctc agt gat    432
Ala Arg Asp Phe Lys Lys Pro Asn Pro Phe Phe Gly Thr Leu Ser Asp
        130                 135                 140 ttc caa cgt tta gtt gat gcc gca cat gca aaa gga ata aag gta att    480
Phe Gln Arg Leu Val Asp Ala Ala His Ala Lys Gly Ile Lys Val Ile
145                 150                 155                 160 att gac ttt gcc ccc aac cat act tct cct gct tca gaa acg aat cct    528
Ile Asp Phe Ala Pro Asn His Thr Ser Pro Ala Ser Glu Thr Asn Pro
                165                 170                 175 tct tat atg gaa aac gga cga ctg tac gat aat ggg aca ttg ctt ggc    576
Ser Tyr Met Glu Asn Gly Arg Leu Tyr Asp Asn Gly Thr Leu Leu Gly
                180                 185                 190 ggt tac aca aat gat gcc aac atg tat ttt cac cat aac ggt gga aca    624
Gly Tyr Thr Asn Asp Ala Asn Met Tyr Phe His His Asn Gly Gly Thr
            195                 200                 205 acg ttt tcc agc tta gag gat ggg att tat cga aat ctg ttt gac ttg    672
Thr Phe Ser Ser Leu Glu Asp Gly Ile Tyr Arg Asn Leu Phe Asp Leu
        210                 215                 220 gcg gac ctt aac cat cag aac cct gtt att gat agg tat tta aaa gat    720
Ala Asp Leu Asn His Gln Asn Pro Val Ile Asp Arg Tyr Leu Lys Asp
225                 230                 235                 240 gca gta aaa atg tgg ata gat atg ggg att gat ggt atc cgt atg gat    768
Ala Val Lys Met Trp Ile Asp Met Gly Ile Asp Gly Ile Arg Met Asp
                245                 250                 255
```

```
gcg gtg aag cac atg ccg ttt gga tgg caa aaa tct ctg atg gat gag      816
Ala Val Lys His Met Pro Phe Gly Trp Gln Lys Ser Leu Met Asp Glu
        260                 265                 270 att gat aac tat cgt cct gtc ttt acg ttt ggg gag tgg ttt ttg tca      864
Ile Asp Asn Tyr Arg Pro Val Phe Thr Phe Gly Glu Trp Phe Leu Ser
            275                 280                 285 gaa aat gaa gtg gac gcg aac aat cat tac ttt gcc aat gaa agt gga      912
Glu Asn Glu Val Asp Ala Asn Asn His Tyr Phe Ala Asn Glu Ser Gly
    290                 295                 300 atg agt ttg ctc gat ttt cgt ttc gga caa aag ctt cgt caa gta ttg      960
Met Ser Leu Leu Asp Phe Arg Phe Gly Gln Lys Leu Arg Gln Val Leu
305                 310                 315                 320 cgc aat aac agc gat aat tgg tat ggc ttt aat caa atg att caa gat     1008
Arg Asn Asn Ser Asp Asn Trp Tyr Gly Phe Asn Gln Met Ile Gln Asp
                325                 330                 335 acg gca tca gca tat gac gag gtt ctc gat caa gta aca ttc ata gac     1056
Thr Ala Ser Ala Tyr Asp Glu Val Leu Asp Gln Val Thr Phe Ile Asp
            340                 345                 350 aac cat gat atg gat cgg ttt atg att gac gga gga gat ccg cgc aag     1104
Asn His Asp Met Asp Arg Phe Met Ile Asp Gly Gly Asp Pro Arg Lys
    355                 360                 365 gtg gat atg gca ctt gct gta tta ttg aca tcc cgt ggc gta ccg aat     1152
Val Asp Met Ala Leu Ala Val Leu Leu Thr Ser Arg Gly Val Pro Asn
370                 375                 380 att tac tat ggt aca gag caa tac atg acc ggt aac ggc gat cca aac     1200
Ile Tyr Tyr Gly Thr Glu Gln Tyr Met Thr Gly Asn Gly Asp Pro Asn
385                 390                 395                 400 aat cgt aag atg atg agt tca ttc aat aaa aat act cgc gcg tat caa     1248
Asn Arg Lys Met Met Ser Ser Phe Asn Lys Asn Thr Arg Ala Tyr Gln
                405                 410                 415 gtg att caa aaa cta tct tct ctc cga cga aac aat ccg gcg tta gct     1296
Val Ile Gln Lys Leu Ser Ser Leu Arg Arg Asn Asn Pro Ala Leu Ala
            420                 425                 430 tat ggt gat acc gaa cag cgt tgg atc aat ggc gat gtg tat gtg tat     1344
Tyr Gly Asp Thr Glu Gln Arg Trp Ile Asn Gly Asp Val Tyr Val Tyr
    435                 440                 445 gag cga cag ttt ggc aaa gat gtt gtg tta gtt gcc gtt aat cgt agt     1392
Glu Arg Gln Phe Gly Lys Asp Val Val Leu Val Ala Val Asn Arg Ser
450                 455                 460 tca agc agt aat tac tcg att act ggc tta ttt aca gct tta cca gca     1440
Ser Ser Ser Asn Tyr Ser Ile Thr Gly Leu Phe Thr Ala Leu Pro Ala
465                 470                 475                 480 gga aca tat acg gat cag ctt ggc ggt ctt tta gac gga aat aca att     1488
Gly Thr Tyr Thr Asp Gln Leu Gly Gly Leu Leu Asp Gly Asn Thr Ile
                485                 490                 495 caa gtc ggt tca aat gga tca gtt aat gca ttt gac tta gga ccg ggg     1536
Gln Val Gly Ser Asn Gly Ser Val Asn Ala Phe Asp Leu Gly Pro Gly
            500                 505                 510 gaa gtc ggt gta tgg gca tac agt gca aca gaa agc acg cca att att     1584
Glu Val Gly Val Trp Ala Tyr Ser Ala Thr Glu Ser Thr Pro Ile Ile
    515                 520                 525 ggt cat gtt gga ccg atg atg ggg caa gtc ggt cat caa gta acc att     1632
Gly His Val Gly Pro Met Met Gly Gln Val Gly His Gln Val Thr Ile
530                 535                 540 gat ggc gaa gga ttc gga aca aat acg ggc act gtg aag ttc gga acg     1680
Asp Gly Glu Gly Phe Gly Thr Asn Thr Gly Thr Val Lys Phe Gly Thr
545                 550                 555                 560 aca gct gcc aat gtt gtg tct tgg tct aac aat caa atc gtt gtg gct     1728
Thr Ala Ala Asn Val Val Ser Trp Ser Asn Asn Gln Ile Val Val Ala
```

```
                       565                 570                 575
gta cca aat gtg tca cca gga aaa tat aat att acc gtc caa tca tca      1776
Val Pro Asn Val Ser Pro Gly Lys Tyr Asn Ile Thr Val Gln Ser Ser
            580                 585                 590 agc ggt caa acg agt gcg gct tat gat aac ttt gaa gta cta aca aat      1824
Ser Gly Gln Thr Ser Ala Ala Tyr Asp Asn Phe Glu Val Leu Thr Asn
        595                 600                 605 gat caa gtg tca gtg cgg ttt gtt gtt aat aac gcg act acc aat cta      1872
Asp Gln Val Ser Val Arg Phe Val Val Asn Asn Ala Thr Thr Asn Leu
    610                 615                 620 ggg caa aat ata tac att gtt ggc aac gta tat gag ctc ggc aac tgg      1920
Gly Gln Asn Ile Tyr Ile Val Gly Asn Val Tyr Glu Leu Gly Asn Trp
625                 630                 635                 640 gac act agt aag gca atc ggt cca atg ttc aat caa gtg gtt tac tcc      1968
Asp Thr Ser Lys Ala Ile Gly Pro Met Phe Asn Gln Val Val Tyr Ser
                645                 650                 655 tat cct aca tgg tat ata gat gtc agt gtc cca gaa gga aag aca att      2016
Tyr Pro Thr Trp Tyr Ile Asp Val Ser Val Pro Glu Gly Lys Thr Ile
            660                 665                 670 gag ttt aag ttt att aaa aaa gac agc caa ggt aat gtc act tgg gaa      2064
Glu Phe Lys Phe Ile Lys Lys Asp Ser Gln Gly Asn Val Thr Trp Glu
        675                 680                 685 agt ggt tca aat cat gtt tat acg aca cca acg aat aca acc gga aaa      2112
Ser Gly Ser Asn His Val Tyr Thr Thr Pro Thr Asn Thr Thr Gly Lys
    690                 695                 700 att ata gtg gat tgg cag aac                                          2133
Ile Ile Val Asp Trp Gln Asn
705                 710

<210> SEQ ID NO 3
<211> LENGTH: 681
<212> TYPE: PRT
<213> ORGANISM: Thermoanaerobacter thermosulfurigenes

<400> SEQUENCE: 3

Ala Pro Asp Thr Ser Val Ser Asn Val Val Asn Tyr Ser Thr Asp Val
1               5                   10                  15

Ile Tyr Gln Ile Val Thr Asp Arg Phe Leu Asp Gly Asn Pro Ser Asn
            20                  25                  30

Asn Pro Thr Gly Asp Leu Tyr Asp Pro Thr His Thr Ser Leu Lys Lys
        35                  40                  45

Tyr Phe Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ala Val Leu Pro Asp Ser Thr Phe Gly Gly Ser Thr
                85                  90                  95

Ser Tyr His Gly Tyr Trp Ala Arg Asp Phe Lys Lys Pro Asn Pro Phe
            100                 105                 110

Phe Gly Ser Phe Thr Asp Phe Gln Asn Leu Ile Ala Thr Ala His Ala
        115                 120                 125

His Asn Ile Lys Val Ile Ile Asp Phe Ala Pro Asn His Thr Ser Pro
    130                 135                 140

Ala Ser Glu Thr Asp Pro Thr Tyr Gly Glu Asn Gly Arg Leu Tyr Asp
145                 150                 155                 160

Asn Gly Val Leu Leu Gly Gly Tyr Thr Asn Asp Thr Asn Gly Tyr Phe
                165                 170                 175
```

-continued

His His Tyr Gly Gly Thr Asn Phe Ser Ser Tyr Glu Asp Gly Ile Tyr
                180                 185                 190

Arg Asn Leu Phe Asp Leu Ala Asp Leu Asp Gln Gln Asn Ser Thr Ile
            195                 200                 205

Asp Ser Tyr Leu Lys Ala Ala Ile Lys Leu Trp Leu Asp Met Gly Ile
        210                 215                 220

Asp Gly Ile Arg Met Asp Ala Val Lys His Met Ala Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Tyr Leu Gly Thr Asn Glu Val Asp Pro Asn Asn Thr Tyr
            260                 265                 270

Phe Ala Asn Glu Ser Gly Met Ser Leu Leu Asp Phe Arg Phe Ala Gln
        275                 280                 285

Lys Val Arg Gln Val Phe Arg Asp Asn Thr Asp Thr Met Tyr Gly Leu
290                 295                 300

Asp Ser Met Ile Gln Ser Thr Ala Ala Asp Tyr Asn Phe Ile Asn Asp
305                 310                 315                 320

Met Val Thr Phe Ile Asp Asn His Asp Met Asp Arg Phe Tyr Thr Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
        355                 360                 365

Asn Gly Asp Pro Tyr Asn Arg Ala Met Met Thr Ser Phe Asp Thr Thr
370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Gln Lys Gln Arg Trp Ile Asn Asn
                405                 410                 415

Asp Val Tyr Ile Tyr Glu Arg Gln Phe Gly Asn Asn Val Ala Leu Val
            420                 425                 430

Ala Ile Asn Arg Asn Leu Ser Thr Ser Tyr Tyr Ile Thr Gly Leu Tyr
        435                 440                 445

Thr Ala Leu Pro Ala Gly Thr Tyr Ser Asp Met Leu Gly Gly Leu Leu
450                 455                 460

Asn Gly Ser Ser Ile Thr Val Ser Ser Asn Gly Ser Val Thr Pro Phe
465                 470                 475                 480

Thr Leu Ala Pro Gly Glu Val Ala Val Trp Gln Tyr Val Ser Thr Thr
                485                 490                 495

Asn Pro Pro Leu Ile Gly His Val Gly Pro Thr Met Thr Lys Ala Gly
            500                 505                 510

Gln Thr Ile Thr Ile Asp Gly Arg Gly Phe Gly Thr Thr Ala Gly Gln
        515                 520                 525

Val Leu Phe Gly Thr Thr Pro Ala Thr Ile Val Ser Trp Glu Asp Thr
530                 535                 540

Glu Val Lys Val Lys Val Pro Ala Leu Thr Pro Gly Lys Tyr Asn Ile
545                 550                 555                 560

Thr Leu Lys Thr Ala Ser Gly Val Thr Ser Asn Ser Tyr Asn Asn Ile
                565                 570                 575

Asn Val Leu Thr Gly Asn Gln Val Cys Val Arg Phe Val Val Asn Asn
            580                 585                 590

Ala Thr Thr Val Trp Gly Glu Asn Val Tyr Leu Thr Gly Asn Val Ala

```
                    595                 600                 605
Glu Leu Gly Asn Trp Asp Thr Ser Lys Ala Ile Gly Pro Met Phe Asn
            610                 615                 620

Gln Val Val Tyr Gln Tyr Pro Thr Trp Tyr Tyr Asp Val Ser Val Pro
625                 630                 635                 640

Ala Gly Thr Thr Ile Glu Phe Ile Lys Lys Asn Gly Ser Thr Val Thr
                645                 650                 655

Trp Glu Gly Gly Tyr Asn His Val Tyr Thr Thr Pro Thr Ser Gly Thr
            660                 665                 670

Ala Thr Val Ile Val Asp Trp Gln Pro
        675                 680

<210> SEQ ID NO 4
<211> LENGTH: 680
<212> TYPE: PRT
<213> ORGANISM: Artificial Sequence
<220> FEATURE:
<223> OTHER INFORMATION: synthetic

<400> SEQUENCE: 4

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30

Gly Ala Leu Phe Ser Ser Gly Cys Thr Asn Leu Arg Lys Tyr Cys Gly
        35                  40                  45

Gly Asp Trp Gln Gly Ile Ile Asn Lys Ile Asn Asp Gly Tyr Leu Thr
    50                  55                  60

Asp Met Gly Val Thr Ala Ile Trp Ile Ser Gln Pro Val Glu Asn Val
65                  70                  75                  80

Phe Ser Val Met Asn Asp Ala Ser Gly Ser Ala Ser Tyr His Gly Tyr
                85                  90                  95

Trp Ala Arg Asp Phe Lys Lys Pro Asn Pro Phe Gly Thr Leu Ser
            100                 105                 110

Asp Phe Gln Arg Leu Val Asp Ala Ala His Ala Lys Gly Ile Lys Val
        115                 120                 125

Ile Ile Asp Phe Ala Pro Asn His Thr Ser Pro Ala Ser Glu Thr Asn
    130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Arg
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
    210                 215                 220

Asp Ala Val Lys His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
                245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
```

```
                275                 280                 285
Leu Arg Asn Asn Ser Asp Asn Trp Tyr Gly Phe Asn Gln Met Ile Gln
290                 295                 300

Asp Thr Ala Ser Ala Tyr Asp Glu Val Leu Asp Gln Val Thr Phe Ile
305                 310                 315                 320

Asp Asn His Asp Met Asp Arg Phe Met Ile Asp Gly Gly Asp Pro Arg
                325                 330                 335

Lys Val Asp Met Ala Leu Ala Val Leu Leu Thr Ser Arg Gly Val Pro
                340                 345                 350

Asn Ile Tyr Tyr Gly Thr Glu Gln Tyr Met Thr Gly Asn Gly Asp Pro
                355                 360                 365

Asn Asn Arg Lys Met Met Ser Ser Phe Asn Lys Asn Thr Arg Ala Tyr
370                 375                 380

Gln Val Ile Gln Lys Leu Ser Ser Leu Arg Arg Asn Asn Pro Ala Leu
385                 390                 395                 400

Ala Tyr Gly Asp Thr Glu Gln Arg Trp Ile Asn Gly Asp Val Tyr Val
                405                 410                 415

Tyr Glu Arg Gln Phe Gly Lys Asp Val Val Leu Val Ala Val Asn Arg
                420                 425                 430

Ser Ser Ser Ser Asn Tyr Ser Ile Thr Gly Leu Phe Thr Ala Leu Pro
                435                 440                 445

Ala Gly Thr His Thr Asp Gln Leu Gly Gly Leu Leu Asp Gly Asn Thr
                450                 455                 460

Ile Gln Val Gly Ser Asn Gly Ser Val Asn Ala Phe Asp Leu Gly Pro
465                 470                 475                 480

Gly Glu Val Gly Val Trp Ala Tyr Ser Ala Thr Glu Ser Thr Pro Ile
                485                 490                 495

Ile Gly His Val Gly Pro Met Met Gly Gln Val Gly His Gln Val Thr
                500                 505                 510

Ile Asp Gly Glu Gly Phe Gly Thr Asn Thr Gly Thr Val Lys Phe Gly
                515                 520                 525

Thr Thr Ala Ala Asn Val Val Ser Trp Ser Asn Asn Gln Ile Val Val
530                 535                 540

Ala Val Pro Asn Val Ser Pro Gly Lys Tyr Asn Ile Thr Val Gln Ser
545                 550                 555                 560

Ser Ser Gly Gln Thr Ser Ala Ala Tyr Asp Asn Phe Glu Val Leu Thr
                565                 570                 575

Asn Asp Gln Val Ser Val Arg Phe Val Val Asn Asn Ala Thr Thr Asn
                580                 585                 590

Leu Gly Gln Asn Ile Tyr Ile Val Gly Asn Val Tyr Glu Leu Gly Asn
                595                 600                 605

Trp Asp Thr Ser Lys Ala Ile Gly Pro Met Phe Asn Gln Val Val Tyr
                610                 615                 620

Ser Tyr Pro Thr Trp Tyr Ile Asp Val Ser Val Pro Glu Gly Lys Thr
625                 630                 635                 640

Ile Glu Phe Lys Phe Ile Lys Lys Asp Ser Gln Gly Asn Val Thr Trp
                645                 650                 655

Glu Ser Gly Ser Asn His Val Tyr Thr Thr Pro Thr Asn Thr Thr Gly
                660                 665                 670

Lys Ile Ile Val Asp Trp Gln Asn
                675                 680

<210> SEQ ID NO 5
```

<211> LENGTH: 680
<212> TYPE: PRT
<213> ORGANISM: Artificial Sequence
<220> FEATURE:
<223> OTHER INFORMATION: synthetic

<400> SEQUENCE: 5

```
Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
            20                  25                  30

Gly Ala Leu Phe Ser Ser Gly Cys Thr Asn Leu Arg Lys Tyr Cys Gly
        35                  40                  45

Gly Asp Trp Gln Gly Ile Ile Asn Lys Ile Asn Asp Gly Tyr Leu Thr
    50                  55                  60

Asp Met Gly Val Thr Ala Ile Trp Ile Ser Gln Pro Val Glu Asn Val
65                  70                  75                  80

Phe Ser Val Met Asn Asp Ala Ser Gly Ser Ala Ser Tyr His Gly Tyr
                85                  90                  95

Trp Ala Arg Asp Phe Lys Lys Pro Asn Pro Phe Phe Gly Thr Leu Ser
            100                 105                 110

Asp Phe Gln Arg Leu Val Asp Ala Ala His Ala Lys Gly Ile Lys Val
        115                 120                 125

Ile Ile Asp Phe Ala Pro Asn His Thr Ser Pro Ala Ser Glu Thr Asn
    130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
    210                 215                 220

Asp Ala Val Ile His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
                245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
        275                 280                 285

Leu Arg Asn Asn Ser Asp Asn Trp Tyr Gly Phe Asn Gln Met Ile Gln
    290                 295                 300

Asp Thr Ala Ser Ala Tyr Asp Glu Val Leu Asp Gln Val Thr Phe Ile
305                 310                 315                 320

Asp Asn His Asp Met Asp Arg Phe Met Ile Asp Gly Gly Asp Pro Arg
                325                 330                 335

Lys Val Asp Met Ala Leu Ala Val Leu Leu Thr Ser Arg Gly Val Pro
            340                 345                 350

Asn Ile Tyr Tyr Gly Thr Glu Gln Tyr Met Thr Gly Asn Gly Asp Pro
        355                 360                 365

Asn Asn Arg Lys Met Met Ser Ser Phe Asn Lys Asn Thr Arg Ala Tyr
    370                 375                 380
```

```
Gln Val Ile Gln Lys Leu Ser Ser Leu Arg Arg Asn Asn Pro Ala Leu
385                 390                 395                 400

Ala Tyr Gly Asp Thr Glu Gln Arg Trp Ile Asn Gly Asp Val Tyr Val
                405                 410                 415

Tyr Glu Arg Gln Phe Gly Lys Asp Val Val Leu Val Ala Val Asn Arg
            420                 425                 430

Ser Ser Ser Ser Asn Tyr Ser Ile Thr Gly Leu Phe Thr Ala Leu Pro
        435                 440                 445

Ala Gly Thr Tyr Thr Asp Gln Leu Gly Gly Leu Leu Asp Gly Asn Thr
    450                 455                 460

Ile Gln Val Gly Ser Asn Gly Ser Val Asn Ala Phe Asp Leu Gly Pro
465                 470                 475                 480

Gly Glu Val Gly Val Trp Ala Tyr Ser Ala Thr Glu Ser Thr Pro Ile
                485                 490                 495

Ile Gly His Val Gly Pro Met Met Gly Gln Val Gly His Gln Val Thr
            500                 505                 510

Ile Asp Gly Glu Gly Phe Gly Thr Asn Thr Gly Thr Val Lys Phe Gly
        515                 520                 525

Thr Thr Ala Ala Asn Val Val Ser Trp Ser Asn Asn Gln Ile Val Val
    530                 535                 540

Ala Val Pro Asn Val Ser Pro Gly Lys Tyr Asn Ile Thr Val Gln Ser
545                 550                 555                 560

Ser Ser Gly Gln Thr Ser Ala Ala Tyr Asp Asn Phe Glu Val Leu Thr
                565                 570                 575

Asn Asp Gln Val Ser Val Arg Phe Val Val Asn Asn Ala Thr Thr Asn
            580                 585                 590

Leu Gly Gln Asn Ile Tyr Ile Val Gly Asn Val Tyr Glu Leu Gly Asn
        595                 600                 605

Trp Asp Thr Ser Lys Ala Ile Gly Pro Met Phe Asn Gln Val Val Tyr
    610                 615                 620

Ser Tyr Pro Thr Trp Tyr Ile Asp Val Ser Val Pro Glu Gly Lys Thr
625                 630                 635                 640

Ile Glu Phe Lys Phe Ile Lys Lys Asp Ser Gln Gly Asn Val Thr Trp
                645                 650                 655

Glu Ser Gly Ser Asn His Val Tyr Thr Thr Pro Thr Asn Thr Thr Gly
            660                 665                 670

Lys Ile Ile Val Asp Trp Gln Asn
        675                 680

<210> SEQ ID NO 6
<211> LENGTH: 686
<212> TYPE: PRT
<213> ORGANISM: Bacillus macerans

<400> SEQUENCE: 6

Ser Pro Asp Thr Ser Val Asn Asn Lys Leu Asn Phe Ser Thr Asp Thr
1               5                   10                  15

Val Tyr Gln Ile Val Thr Asp Arg Phe Val Asp Gly Asn Ser Ala Asn
                20                  25                  30

His Pro Thr Gly Ala Ala Phe Ser Asp His Ser Asn Leu Lys Leu
            35                  40                  45

Tyr Phe Gly Gly Asp Trp Gln Gly Ile Thr Asn Lys Ile Asn Asp Gly
        50                  55                  60

Tyr Leu Thr Gly Met Gly Ile Thr Ala Leu Trp Ile Ser Gln Pro Val
```

```
                65                  70                  75                  80
        Glu Asn Ile Thr Ala Val Ile Lys Tyr Ser Gly Val Asn Asn Thr Ala
                        85                  90                  95

Tyr His Gly Tyr Trp Pro Arg Asp Phe Lys Lys Thr Asn Ala Ala Phe
                        100                 105                 110

Gly Ser Phe Thr Asp Phe Ser Asn Leu Ile Ala Ala His Ser His
                        115                 120                 125

Asn Ile Lys Val Val Met Asp Phe Ala Pro Asn His Thr Asn Pro Ala
                130                 135                 140

Ser Ser Thr Asp Pro Ser Phe Ala Glu Asn Gly Ala Leu Tyr Asn Asn
        145                 150                 155                 160

Gly Thr Leu Leu Gly Lys Tyr Ser Asn Asp Thr Ala Gly Leu Phe His
                        165                 170                 175

His Asn Gly Gly Thr Asp Phe Ser Thr Thr Glu Ser Gly Ile Tyr Lys
                        180                 185                 190

Asn Leu Tyr Asp Leu Ala Asp Ile Asn Gln Asn Asn Asn Thr Ile Asp
                        195                 200                 205

Ser Tyr Leu Lys Glu Ser Ile Gln Leu Trp Leu Asn Leu Gly Val Asp
        210                 215                 220

Gly Ile Arg Phe Asp Ala Val Lys His Met Pro Gln Gly Trp Gln Lys
        225                 230                 235                 240

Ser Tyr Val Ser Ser Ile Tyr Ser Ser Ala Asn Pro Val Phe Thr Phe
                        245                 250                 255

Gly Glu Trp Phe Leu Gly Pro Asp Glu Met Thr Gln Asp Asn Ile Asn
                        260                 265                 270

Phe Ala Asn Gln Ser Gly Met His Leu Leu Asp Phe Ala Phe Ala Gln
                        275                 280                 285

Glu Ile Arg Glu Val Phe Arg Asp Lys Ser Glu Thr Met Thr Asp Leu
                        290                 295                 300

Asn Ser Val Ile Ser Ser Thr Gly Ser Ser Tyr Asn Tyr Ile Asn Asn
        305                 310                 315                 320

Met Val Thr Phe Ile Asp Asn His Asp Met Asp Arg Phe Gln Gln Ala
                        325                 330                 335

Gly Ala Ser Thr Arg Pro Thr Glu Gln Ala Leu Ala Val Thr Leu Thr
                        340                 345                 350

Ser Arg Gly Val Pro Ala Ile Tyr Tyr Gly Thr Glu Gln Tyr Met Thr
                        355                 360                 365

Gly Asn Gly Asp Pro Asn Asn Arg Gly Met Met Thr Gly Phe Asp Thr
                        370                 375                 380

Asn Lys Thr Ala Tyr Lys Val Ile Lys Ala Leu Ala Pro Leu Arg Lys
        385                 390                 395                 400

Ser Asn Pro Ala Leu Ala Tyr Gly Ser Thr Thr Gln Arg Trp Val Asn
                        405                 410                 415

Ser Asp Val Tyr Val Tyr Glu Arg Lys Phe Gly Ser Asn Val Ala Leu
                        420                 425                 430

Val Ala Val Asn Arg Ser Ser Thr Thr Ala Tyr Pro Ile Ser Gly Ala
                        435                 440                 445

Leu Thr Ala Leu Pro Asn Gly Ser Tyr Thr Asp Val Leu Gly Gly Leu
                        450                 455                 460

Leu Asn Gly Asn Ser Ile Thr Val Asn Gly Gly Thr Val Ser Asn Phe
        465                 470                 475                 480

Thr Leu Ala Ala Gly Gly Thr Ala Val Trp Gln Tyr Thr Thr Thr Glu
                        485                 490                 495
```

-continued

```
Ser Ser Pro Ile Ile Gly Asn Val Gly Pro Thr Met Gly Lys Pro Gly
            500                 505                 510

Asn Thr Ile Thr Ile Asp Gly Arg Gly Phe Gly Thr Thr Lys Asn Lys
            515                 520                 525

Val Thr Phe Gly Thr Thr Ala Val Thr Gly Ala Asn Ile Val Ser Trp
            530                 535                 540

Glu Asp Thr Glu Ile Lys Val Lys Val Pro Asn Val Ala Ala Gly Asn
545                 550                 555                 560

Thr Ala Val Thr Val Thr Asn Ala Ala Gly Thr Thr Ser Ala Ala Phe
            565                 570                 575

Asn Asn Phe Asn Val Leu Thr Ala Asp Gln Val Thr Val Arg Phe Lys
            580                 585                 590

Val Asn Asn Ala Thr Thr Ala Leu Gly Gln Asn Val Tyr Leu Thr Gly
            595                 600                 605

Asn Val Ala Glu Leu Gly Asn Trp Thr Ala Ala Asn Ala Ile Gly Pro
            610                 615                 620

Met Tyr Asn Gln Val Glu Ala Ser Tyr Pro Thr Trp Tyr Phe Asp Val
625                 630                 635                 640

Ser Val Pro Ala Asn Thr Ala Leu Gln Phe Lys Phe Ile Lys Val Asn
            645                 650                 655

Gly Ser Thr Val Thr Trp Glu Gly Gly Asn Asn His Thr Phe Thr Ser
            660                 665                 670

Pro Ser Ser Gly Val Ala Thr Val Thr Val Asp Trp Gln Asn
            675                 680                 685

<210> SEQ ID NO 7
<211> LENGTH: 682
<212> TYPE: PRT
<213> ORGANISM: Paenibacillus illinoisensis

<400> SEQUENCE: 7

Asp Thr Ala Val Thr Asn Lys Gln Asn Phe Ser Thr Asp Val Ile Tyr
1               5                   10                  15

Gln Val Phe Thr Asp Arg Phe Leu Asp Gly Asn Pro Ser Asn Asn Pro
            20                  25                  30

Thr Gly Ala Ala Phe Asp Gly Thr Cys Ser Asn Leu Lys Leu Tyr Cys
            35                  40                  45

Gly Gly Asp Trp Gln Gly Leu Ile Asn Lys Ile Asn Asp Asn Tyr Phe
        50                  55                  60

Ser Asp Leu Gly Val Thr Ala Leu Trp Ile Ser Gln Pro Val Glu Asn
65                  70                  75                  80

Ile Phe Ala Thr Ile Asn Tyr Ser Gly Val Thr Asn Thr Ala Tyr His
            85                  90                  95

Gly Tyr Trp Ala Arg Asp Phe Lys Lys Thr Asn Pro Tyr Phe Gly Thr
            100                 105                 110

Met Thr Asp Phe Gln Asn Leu Val Thr Ser Ala His Ala Lys Gly Ile
            115                 120                 125

Lys Ile Ile Ile Asp Phe Ala Pro Asn His Thr Phe Pro Ala Met Glu
        130                 135                 140

Thr Asp Thr Ser Phe Ala Glu Asn Gly Lys Leu Tyr Asp Asn Gly Ser
145                 150                 155                 160

Leu Val Gly Gly Tyr Thr Asn Asp Thr Asn Gly Tyr Phe His His Asn
            165                 170                 175

Gly Gly Ser Asp Phe Ser Thr Leu Glu Asn Gly Ile Tyr Lys Asn Leu
```

-continued

```
            180                 185                 190
Tyr Asp Leu Ala Asp Leu Asn His Asn Asn Ser Thr Ile Asp Thr Tyr
            195                 200                 205
Phe Lys Asp Ala Ile Lys Leu Trp Leu Asp Met Gly Val Asp Gly Ile
            210                 215                 220
Arg Val Asp Ala Val Lys His Met Pro Gln Gly Trp Gln Lys Asn Trp
225                 230                 235                 240
Met Ser Ser Ile Tyr Ala His Lys Pro Val Phe Thr Phe Gly Glu Trp
                245                 250                 255
Phe Leu Gly Ser Ala Ala Ser Asp Ala Asp Asn Thr Asp Phe Ala Asn
            260                 265                 270
Glu Ser Gly Met Ser Leu Leu Asp Phe Arg Phe Asn Ser Ala Val Arg
            275                 280                 285
Asn Val Phe Arg Asp Asn Thr Ser Asn Met Tyr Ala Leu Asp Ser Met
            290                 295                 300
Leu Thr Ala Thr Ala Ala Asp Tyr Asn Gln Val Asn Asp Gln Val Thr
305                 310                 315                 320
Phe Ile Asp Asn His Asp Met Asp Arg Phe Lys Thr Ser Ala Val Asn
                325                 330                 335
Asn Arg Arg Leu Glu Gln Ala Leu Ala Phe Thr Leu Thr Ser Arg Gly
            340                 345                 350
Val Pro Ala Ile Tyr Tyr Gly Thr Glu Gln Tyr Leu Thr Gly Asn Gly
            355                 360                 365
Asp Pro Asp Asn Arg Gly Lys Met Pro Ser Phe Ser Lys Ser Thr Thr
            370                 375                 380
Ala Phe Ser Val Ile Ser Lys Leu Ala Pro Leu Arg Lys Ser Asn Pro
385                 390                 395                 400
Ala Ile Ala Tyr Gly Ser Thr Gln Gln Arg Trp Ile Asn Asn Asp Val
                405                 410                 415
Tyr Ile Tyr Glu Arg Lys Phe Gly Lys Ser Val Ala Val Val Ala Val
            420                 425                 430
Asn Arg Asn Leu Thr Thr Pro Thr Ser Ile Thr Asn Leu Asn Thr Ser
            435                 440                 445
Leu Pro Ser Gly Thr Tyr Thr Asp Val Leu Gly Gly Val Leu Asn Gly
            450                 455                 460
Asn Asn Ile Thr Ser Ser Gly Gly Asn Ile Ser Ser Phe Thr Leu Ala
465                 470                 475                 480
Ala Gly Ala Thr Ala Val Trp Gln Tyr Thr Ala Ser Glu Thr Thr Pro
                485                 490                 495
Thr Ile Gly His Val Gly Pro Val Met Gly Lys Pro Gly Asn Val Val
            500                 505                 510
Thr Ile Asp Gly Arg Gly Phe Gly Ser Thr Lys Gly Thr Val Tyr Phe
            515                 520                 525
Gly Thr Thr Ala Val Thr Gly Ser Ala Ile Thr Ser Trp Glu Asp Thr
            530                 535                 540
Gln Ile Lys Val Thr Ile Pro Pro Val Ala Gly Gly Asp Tyr Ala Val
545                 550                 555                 560
Lys Val Ala Ala Asn Gly Val Asn Ser Asn Ala Tyr Asn Asp Phe Thr
                565                 570                 575
Ile Leu Ser Gly Asp Gln Val Ser Val Arg Phe Val Ile Asn Asn Ala
            580                 585                 590
Thr Thr Ala Leu Gly Glu Asn Ile Tyr Leu Thr Gly Asn Val Ser Glu
            595                 600                 605
```

```
Leu Gly Asn Trp Thr Thr Gly Ala Ala Ser Ile Gly Pro Ala Phe Asn
        610                 615                 620

Gln Val Ile His Ala Tyr Pro Thr Trp Tyr Tyr Asp Val Ser Val Pro
625                 630                 635                 640

Ala Gly Lys Gln Leu Glu Phe Lys Phe Phe Lys Lys Asn Gly Ala Thr
                645                 650                 655

Ile Thr Trp Glu Gly Gly Ser Asn His Thr Phe Thr Thr Pro Thr Ser
            660                 665                 670

Gly Thr Ala Thr Val Thr Val Asn Trp Gln
            675             680
```